US012779021B2

(12) United States Patent
He et al.

(10) Patent No.: US 12,779,021 B2

(45) **Date of Patent: *Nov. 3, 2026**

(54) INTERLEUKIN-2 MUTANT AND FUSION PROTEIN THEREOF

(71) Applicant: Fortvita Biologics (Singapore) Pte. Ltd., Singapore (SG)

(72) Inventors: Kaijie He, Suzhou (CN); Fenggen Fu, Suzhou (CN); Weiwei Wu, Suzhou (CN); Shuaixiang Zhou, Suzhou (CN); Jian Guan, Suzhou (CN)

(73) Assignee: Fortvita Biologics (Singapore) Pte. Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 19/376,374

(22) Filed: Oct. 31, 2025

(65) Prior Publication Data

US 2026/0053898 A1 Feb. 26, 2026

Related U.S. Application Data

(63) Continuation of application No. 18/693,453, filed as application No. PCT/CN2022/120265 on Sep. 21, 2022.

(30) Foreign Application Priority Data

Sep. 22, 2021 (CN) .......................... 202111110032.3

(51) Int. Cl.

*A61K 39/00* (2006.01)
*A61K 45/06* (2006.01)
*A61P 35/00* (2006.01)
*C07K 14/55* (2006.01)
*C07K 16/28* (2006.01)

(52) U.S. Cl.

CPC .............. *A61K 39/00* (2013.01); *A61K 45/06* (2013.01); *A61P 35/00* (2018.01); *C07K 14/55* (2013.01); *C07K 16/2818* (2013.01); *A61K 2039/505* (2013.01); *C07K 2317/14* (2013.01); *C07K 2317/52* (2013.01); *C07K 2317/565* (2013.01); *C07K 2319/30* (2013.01)

(58) Field of Classification Search

None

See application file for complete search history.

(56) References Cited

U.S. PATENT DOCUMENTS

| | | | |
|---|---|---|---|
| 4,518,584 A | 5/1985 | Mark et al. | |
| 5,153,310 A | 10/1992 | Mitchell et al. | |
| 6,171,586 B1 | 1/2001 | Lam et al. | |
| 6,207,156 B1 | 3/2001 | Kuchroo et al. | |
| 6,267,958 B1 | 7/2001 | Andya et al. | |
| 9,244,059 B2 | 1/2016 | Triebel et al. | |
| 9,447,159 B2 | 9/2016 | Ast et al. | |
| 10,316,089 B2 | 6/2019 | Baruah et al. | |
| 10,875,901 B2 | 12/2020 | Greve | |
| 11,111,312 B2 | 9/2021 | Ast et al. | |
| 12,269,855 B2 | 4/2025 | Kang et al. | |
| 2004/0175357 A1 | 9/2004 | Shanafelt et al. | |
| 2006/0160187 A1 | 7/2006 | Denis-Mize et al. | |
| 2006/0269515 A1 | 11/2006 | Denis-Mize et al. | |
| 2011/0070238 A1 | 3/2011 | Triebel et al. | |
| 2011/0150892 A1 | 6/2011 | Thudium et al. | |
| 2012/0244112 A1 | 9/2012 | Ast et al. | |
| 2017/0044229 A1 | 2/2017 | Garcia et al. | |
| 2017/0044260 A1* | 2/2017 | Baruah | A61P 35/00 |
| 2018/0142037 A1 | 5/2018 | Ast et al. | |
| 2018/0326010 A1 | 11/2018 | Codarri et al. | |
| 2021/0213102 A1 | 7/2021 | Kang et al. | |
| 2021/0221863 A1 | 7/2021 | Kang et al. | |
| 2021/0269497 A1 | 9/2021 | Li et al. | |
| 2022/0112260 A1 | 4/2022 | Greve | |
| 2023/0145766 A1 | 5/2023 | He et al. | |
| 2023/0174604 A1 | 6/2023 | Fu et al. | |

(Continued)

FOREIGN PATENT DOCUMENTS

| | | |
|---|---|---|
| CA | 3040313 A | 5/2018 |
| CN | 1309705 A | 8/2001 |
| CN | 1723032 A | 1/2006 |

(Continued)

OTHER PUBLICATIONS

Mohammad et al (Cytokines as potential combination agents with PD-1/PD-L1 blockade for cancer treatment J Cell Physiol. Jul. 2020;235(7-8):5449-5460). (Year: 2020).*
Dehghan et al (Efficacy and antitumor activity of a mutant type of interleukin 2. Sci Rep. Mar. 30, 2022;12(1):5376) (Year: 2022).*
International Preliminary Report on Patentability for Application No. PCT/CN2024/083130, mailed Oct. 2, 2025.
International Preliminary Report on Patentability for Application No. PCT/CN2019/107054, mailed Apr. 1, 2021.
International Preliminary Report on Patentability for Application No. PCT/CN2019/107055, mailed Apr. 1, 2021.
International Preliminary Report on Patentability for Application No. PCT/CN2021/081840, mailed Sep. 29, 2022.
International Preliminary Report on Patentability for Application No. PCT/CN2021/081841, mailed Sep. 29, 2022.

(Continued)

*Primary Examiner* — Zachariah Lucas
*Assistant Examiner* — Sarah A Alsomairy
(74) *Attorney, Agent, or Firm* — Wolf, Greenfield & Sacks, P.C.

(57) ABSTRACT

Disclosed are a new interleukin-2 (IL-2) mutant protein and the use thereof. Compared with wild-type IL-2, the IL-2 mutant protein has improved properties, such as an improved IL-2 receptor binding property and improved druggability. Also provided are a fusion protein, dimer and immunoconjugate comprising the IL-2 mutant protein, nucleic acids encoding the IL-2 mutant protein, the dimer and the immunoconjugate, and a vector and host cell comprising the nucleic acid. Further provided are methods for preparing the IL-2 mutant protein, the fusion protein, the dimer and the immunoconjugate, a pharmaceutical composition containing same, and the therapeutic use thereof.

24 Claims, 24 Drawing Sheets

Specification includes a Sequence Listing.

(56) References Cited

U.S. PATENT DOCUMENTS

| | | | |
|---|---|---|---|
| 2024/0391973 | A1 | 11/2024 | He et al. |

FOREIGN PATENT DOCUMENTS

| | | | |
|---|---|---|---|
| CN | 101426916 | A | 5/2009 |
| CN | 102101885 | A1 | 6/2011 |
| CN | 103492411 | A | 1/2014 |
| CN | 104231068 | A | 12/2014 |
| CN | 105980410 | A | 9/2016 |
| CN | 110003339 | A | 7/2019 |
| CN | 110382525 | A | 10/2019 |
| CN | 110392692 | A | 10/2019 |
| CN | 111655718 | A | 9/2020 |
| CN | 111868079 | A | 10/2020 |
| CN | 112105634 | A | 12/2020 |
| CN | 112638406 | A | 4/2021 |
| CN | 114786708 | A | 7/2022 |
| CN | 115315437 | A | 11/2022 |
| CN | 115362168 | A | 11/2022 |
| CN | 115698052 | A | 2/2023 |
| CN | 116370641 | A | 7/2023 |
| EA | 201591766 | A1 | 2/2016 |
| EP | 2970486 | B2 | 5/2018 |
| EP | 4273161 | A1 | 5/2018 |
| JP | H04507250 | A | 12/1992 |
| JP | 2007527242 | A | 9/2007 |
| JP | 2007528728 | A | 10/2007 |
| JP | 2007535919 | A | 12/2007 |
| JP | 2008509651 | A | 4/2008 |
| JP | 2014506793 | A | 3/2014 |
| JP | 2017500040 | A | 1/2017 |
| JP | 2017518361 | A | 7/2017 |
| JP | 2018531986 | A | 11/2018 |
| JP | 2020515275 | A | 5/2020 |
| JP | 2020529977 | A | 10/2020 |
| JP | 2021531013 | A | 11/2021 |
| JP | H04503604 | A | 11/2023 |
| TW | 201237165 | A1 | 9/2012 |
| TW | 201831688 | A | 9/2018 |
| TW | 201900220 | A | 1/2019 |
| TW | 202014432 | A | 4/2020 |
| TW | 202144391 | A | 12/2021 |
| TW | 202144392 | A | 12/2021 |
| TW | 202227123 | A | 7/2022 |
| TW | 202444747 | A | 11/2024 |
| WO | 1986000334 | A1 | 1/1986 |
| WO | 1990010070 | A1 | 9/1990 |
| WO | 9102000 | A1 | 2/1991 |
| WO | 9842752 | A1 | 10/1998 |
| WO | 0037504 | A2 | 6/2000 |
| WO | 0114424 | A2 | 3/2001 |
| WO | 2005086751 | A2 | 9/2005 |
| WO | 2005086798 | A2 | 9/2005 |
| WO | 2005100395 | A2 | 10/2005 |
| WO | 2006044908 | A2 | 4/2006 |
| WO | WO 2008/112407 | A1 | 9/2008 |
| WO | 2010021961 | A2 | 2/2010 |
| WO | 2010087994 | A2 | 8/2010 |
| WO | 2012119093 | A1 | 9/2012 |
| WO | 2014008218 | A1 | 1/2014 |
| WO | 2014153111 | A2 | 9/2014 |
| WO | 2017024465 | A1 | 2/2017 |
| WO | 2017025016 | A1 | 2/2017 |
| WO | WO 2018/184964 | A1 | 10/2018 |
| WO | 2018223923 | A1 | 12/2018 |
| WO | 2019028419 | A1 | 2/2019 |
| WO | 2019096194 | A1 | 5/2019 |
| WO | WO 2019/125732 | A1 | 6/2019 |
| WO | 2019173832 | A1 | 9/2019 |
| WO | 2019246404 | A1 | 12/2019 |
| WO | 2020020783 | A1 | 1/2020 |
| WO | 2020057645 | A1 | 3/2020 |
| WO | 2020057646 | A1 | 3/2020 |
| WO | 2020247843 | A1 | 12/2020 |
| WO | 2020252418 | A1 | 12/2020 |
| WO | 2020252421 | A1 | 12/2020 |
| WO | 2021185361 | A1 | 9/2021 |
| WO | 2021185362 | A1 | 9/2021 |
| WO | 2023023070 | A1 | 2/2023 |
| WO | 2023045977 | A1 | 3/2023 |
| WO | 2024193670 | A1 | 9/2024 |

OTHER PUBLICATIONS

International Preliminary Report on Patentability for Application No. PCT/CN2022/120265, mailed Apr. 4, 2024.

International Search Report and Written Opinion for PCT/CN2019/107055, mailed on Dec. 12, 2019.

Wang et al., In vitro characterization of the anti-PD-1 antibody nivolumab, BMS-936558, and in vivo toxicology in non-human primates. Cancer Immunol Res. Sep. 2014;2(9):846-56. doi: 10.1158/2326-6066.CIR-14-0040. Epub May 28, 2014.

Bazan et al.: "Unraveling the structure of IL-2", Science 257, 410-413 (1992). [5 pages].

Benatuil et al.: "An improved yeast transformation method for the generation of very large human antibody libraries", Protein Engineering, Design & Selection, vol. 23, No. 4, pp. 155-159, 2010. [5 pages].

Boyman et al.: "Selective Stimulation of T Cell Subsets with Antibody-Cytokine Immune Complexes", Science 311 (5769): 1924-1927 (2006). [4 pages].

Boyman et al.: "The role of interleukin-2 during homeostasis and activation of the immune system", J. Nat. Rev. Immunol. 12, 180-190 (2012). [11 pages].

Camacho et al.: "Phase 1 clinical trial of anti-CTLA4 human monoclonal antibody CP-675,206 in patients (pts) with advanced solid malignancies", J. Clin. Oncology 22(145): Abstract No. 2505 (2004). [2 pages].

Carmenate et al.: "Human IL-2 mutein with higher antitumor efficacy than wild type IL-2". The Journal of Immunology. 2013, 190(12): 6230-6238. [9 pages].

Chen et al.: "A novel human IL 2 mutein with minimal systemic toxicity exerts greater antitumor efficacy than wild-type IL 2", Cell Death and Disease, 2018, 9:989, pp. 1-12. [12 pages].

D'Cruz et al.: "Development and function of agonist-induced CD25+ Foxp3+ regulatory T cells in the absence of interleukin 2 signaling", Nature Immunol. 6, 1152-59 (2005). [8 pages].

Denesyuk et al.: "Molecular models of two competitive inhibitors, IL-202 and IL-203, generated by alternative splicing of human interleukin-2", Immunology Letters, 60 (1998) 61-66. [6 pages].

Estep et al.: "High throughput solution based measurement of antibody-antigen affinity and epitope binning". MAbs, 2013, 5(2): pp. 270-278. [9 pages].

Fontenot et al.: "A function for interleukin 2 in Foxp3-expressing regulatory T cells", Nature Immunol. 6, 1142-51 (2005). [11 pages].

Gerngross: "Advances in the production of human therapeutic proteins in yeasts and filamentous fungi", Nat Biotech 22, 1409-1414 (2004). [6 pages].

Graham et al.: "Characteristics of a human cell line transformed by DNA from human adenovirus type 5", J Gen Virol 36, 59-72 (1977). [14 pages].

Holcomb. "A forced marriage of IL-2 and PD-1 antibody nurtures tumorinfiltrating T cells", The Journal of Clinical Investigation, 2022, 132(3):e156628. [3 pages].

Hadash-Bengad et al., "Immunotherapy Potentiates the Effect of Chemotherapy in Metastatic Melanonma—A Retrospective Study", Frontiers in Oncology, 2020, vol. 10, Article 70, 8 pages.

Hurwitz et al.: "CTLA-4 blockade synergizes with tumor-derived granulocyte-macrophage colony-stimulating factor for treatment of an experimental mammary carcinoma", Proc. Natl. Acad. Sci. USA (1998) 95(17):10067-10071. [5 pages].

International Search Report and Written Opinion of PCT/CN2019/107055, mailed on Dec. 12, 2019, including translations. [24 pages].

International Search Report and Written Opinion of PCT/CN2019/107054, mailed on Dec. 20, 2019, including translations. [23 pages].

International Search Report and Written Opinion of PCT/CN2021/081841, mailed Jun. 18, 2021, including translations. [24 pages].

International Search Report and Written Opinion of PCT/CN2021/

(56) References Cited

OTHER PUBLICATIONS 081840, mailed Jul. 1, 2021, including translations. [21 pages].
International Search Report and Written Opinion of PCT/CN2022/120265, mailed Nov. 25, 2022, including translations. [28 pages].
International Search Report of PCT/CN2024/083130, mailed Jun. 19, 2024, including translation. [18 pages].
International Search Report and Written Opinion of PCT/CN2024/143132, mailed Mar. 25, 2025, including translation. 13 pages.
Kamimura et al. "IL-2 In Vivo Activities and Antitumor Efficacy Enhanced by an Anti-IL-2 mAb1", J Immunol 177, 306-14(2006). [9 pages].
Krieg et al.: "Improved IL-2 immunotherapy by selective stimulation of IL-2 receptors on lymphocytes and endothelial cells", Proc Natl Acad Sci 107, 11906-11 (2010). [6 pages].
Lenardo et al.: "Interleukin-2 programs mouse αβ T lymphocytes for apoptosis", Nature 353: 858 (1991). [4 pages].
Levin et al.: "Exploiting a natural conformational switch to engineer an interleukin-2 'superkine' ", Nature, vol. 484, p. 529-533, 2012. [7 pages].
Li et al: "Optimization of humanized IgGs in glycoengineered Pichia pastoris", Nat Biotech 24, 210-215 (2006). [6 pages].
Lopes et al.: "ALKS 4230: a novel engineered IL-2 fusion protein with an improved cellular selectivity profile for cancer immunotherapy", Journal for Immunotherapy of Cancer, vol. 8, No. 1, 2020:e000673. [13 pages].
Maloy et al.: "Fueling regulation: IL-2 keeps CD4+ Treg cells fit", Nature Immunol. 6, 1071-72 (2005). [2 pages].
Mather: "Establishment and Characterization of Two Distinct Mouse Testicular Epithelial Cell Lines", Biol Reprod 23, 243-252 (1980). [10 pages].
Mather et al.: "Culture of Testicular Cells in Hormone-supplemented serum-free medium", Annals N. Y. Acad Sci. 383, 44-68 (1982). [25 pages].
Mokyr et al.: "Realization of the Therapeutic Potential of CTLA-4 Blockade in Low-Dose Chemotherapy-treated Tumor-bearing Mice", (1998) Cancer Res. 58:5301-5304. [5 pages].
Ren et al. "Selective delivery of low-affinity IL-2 to PD-1 + T cells rejuvenates antitumor immunity with reduced toxicity" The Journal of Clinical Investigation, vol. 132, No. 3, 2022, e153604. [13 pages].
Smith: "Interleukin-2, Inception, Impact and Implications", Science 240, 1169-76 (1988). [8 pages].
Smith et al.: "A novel, native-format bispecific antibody triggering T-cell killing of B-cells is robustly active in mouse tumor models and cynomolgus monkeys", Scientific Reports, 2015, 5:17943 [12 pages].
Tilly et al., Identification of a Small Molecule Inhibitor of the IL-2/IL-2Ra Receptor Interaction Which Binds to IL-2. Journal of the American Chemical Society, 119 (32): 7589-7590, 1997. [2 pages].
Urlaub et al.: "Isolation of Chinese hamster cell mutants deficient in dihydrofolate reductase activity", Proc Natl Acad Sci USA 77, 4216 (1980). [5 pages].
Vazquez-Lombardi et al.: "Potent antitumour activity of interleukin-2-Fc fusion proteins requires Fc-mediated depletion of regulatory T-cells", Nature Communications, 8:15373, 2017. [12 pages].
Vidarsson et al.: "IgG subclasses and allotypes: from structure to effector functions", 2014, vol. 5, Article 520: 1-17. [17 pages].
Wu et al: "IL-2R[alpha]-biased agonist enhances antitumor immunity by invigorating tumor-infiltrating CD25+CD8+ T cells", Nature Cancer, vol. 4, No. 9, Aug. 7, 2023 (Aug. 7, 2023). [35 pages].
Xu et al.: "Structure-Function Studies of the C-terminal α-Helix of Human Iterleukin-2 by site-directed mutagenesis", Chinese Journal of Biotechnology, 9(4):298-302, 1993. [5 pages].
Zhang et al.: "Comparative analysis of bat genomes provides insight into the evolution of flight and immunity", Science. Jan. 25, 2013; 339(6118). [10 pages].
Jones, Andrew J.S., "Analysis of polypeptides and proteins", Advanced Drug Delivery Reviews, 1993, vol. 10, pp. 29-90.
Peptide and Protein Drug Delivery. Edited by Vincent H. L. Lee. Advances in Parenteral Sciences/4, Marcel Dekker Inc., New York. 1991, pp. v-xvi and 247-301. [77 pages].
Peterson et al. "A long lived IL-2 mutein that selectively activates and expands regulatory T cells as a therapy for autoimmune disease", J. Autolmmun. 2018, 95, pp. 1-14. [14 pages].
Rao et al., "Interleukin-2 mutants with enhanced a-receptor subunit binding affinity", Protein Engineering, 2003, vol. 16. No. 12, pp. 1081-1087. [7 pages].
Sheridan, C., "Cautious optimism surrounds early clinical data for PD-1 blocker", Nature Biotechnology, 2012, vol. 30, No. 8, pp. 729-730.
U.S. Appl. No. 19/166,754, filed Sep. 18, 2025. [62 pages].
Written Opinion of PCT/CN2024/083130, mailed Jun. 19, 2024, including translation. [10 pages].
Chirifu et al., "Crystal structure of the IL-15-IL-15Rα complex, a cytokine-receptor unit presented in trans", Nature Immunology, vol. 8, No. 9, 2007, pp. 1001-1007.
Berry et al., Substitution of cysteine for selenocysteine in type I iodothyronine deiodinase reduces the catalytic efficiency of the protein but enhances its translation. Endocrinology. Oct. 1992;131(4):1848-52. doi: 10.1210/endo.131.4.1396330.
Gasser et al., Antibody production with yeasts and filamentous fungi: on the road to large scale? Biotechnol Lett. Feb. 2007;29(2):201-12. doi: 10.1007/s10529-006-9237-x. Epub Nov. 22, 2006.
Keskin et al., A new, structurally nonredundant, diverse data set of protein-protein interfaces and its implications. Protein Sci. Apr. 2004;13(4):1043-55. doi: 10.1110/ps.03484604.
Kontermann et al., Bispecific antibodies. Drug Discov Today. Jul. 2015;20(7):838-47. doi: 10.1016/j.drudis.2015.02.008. Epub Feb. 26, 2015.
Nelson et al., The "Trojan Horse" Approach to Tumor Immunotherapy: Targeting the Tumor Microenvironment. J Immunol Res. 2014:2014:789069. doi: 10.1155/2014/789069. Epub May 18, 2014.
Pakula et al., Genetic analysis of protein stability and function. Annu Rev Genet. 1989:23:289-310. doi: 10.1146/annurev.ge.23.120189.001445.
Prokofieva et al., Lecture course on General pharmacology: a teaching aid. Ulyanovsk: Ulyanovsk State University. 2017. 310 pages.
Rudikoff et al., Single amino acid substitution altering antigen-binding specificity. Proc Natl Acad Sci U S A. Mar. 1982;79(6):1979-83. doi: 10.1073/pnas.79.6.1979.
Singer et al., Genes and Genomes: in 2 volumes, vol. 1, Translation from English, Moscow: Mir, 1998, 373 pages, p. 63.
Su et al., The role of Antibody VK Framework 3 region towards Antigen binding: Effects on recombinant production and Protein L binding. Sci Rep. Jun. 19, 2017;7(1):3766. doi: 10.1038/s41598-017-02756-3.
Tokuriki et al., Stability effects of mutations and protein evolvability. Curr Opin Struct Biol. Oct. 2009;19(5):596-604. doi: 10.1016/j.sbi.2009.08.003. Epub Sep. 16, 2009.

* cited by examiner

| | CD8+PD1-T | CD8+PD1+T |
|---|---|---|
| EC50 | 0.5273 | 0.03037 |

| | CD8+PD1-T | CD8+PD1+T |
|---|---|---|
| EC50 | 0.6984 | 0.03465 |

| | CD8+PD1-T | CD8+PD1+T |
|---|---|---|
| EC50 | 1.515 | 0.009212 |

| | CD4+PD1-T | CD4+PD1+T |
|---|---|---|
| EC50 | 4.142 | 0.01879 |

| | CD8+PD1-T | CD8+PD1+T |
|---|---|---|
| EC50 | 42.78 | 0.03057 |

| | CD4+PD1-T | CD4+PD1+T |
|---|---|---|
| EC50 | 44.43 | 0.08780 |

| | CD8+PD1-T | CD8+PD1+T |
|---|---|---|
| EC50 | 180.9 | 0.08282 |

| | CD4+PD1-T | CD4+PD1+T |
|---|---|---|
| EC50 | 84.30 | 0.04347 |

| | CD8+PD1-T | CD8+PD1+T |
|---|---|---|
| EC50 | 29.88 | 1.130 |

| | CD4+PD1-T | CD4+PD1+T |
|---|---|---|
| EC50 | 3.915 | 0.3267 |

| | CD4+PD1-T | CD4+PD1+T |
|---|---|---|
| EC50 | 82.31 | 0.2057 |

| | CD4+PD1-T | CD4+PD1+T |
|---|---|---|
| EC50 | 1239 | 0.3267 |

| | huPD1- | huPD1+ |
|---|---|---|
| EC50 | 0.007573 | 0.008225 |

| | hPD1- | hPD1+ |
|---|---|---|
| EC50 | 0.02378 | 0.006749 |

| | huPD1- | huPD1+ |
|---|---|---|
| EC50 | 0.5372 | 0.01005 |

| | huPD1- | huPD+ |
|---|---|---|
| EC50 | 5.974 | 0.06220 |

| | huPD1- | huPD+ |
|---|---|---|
| EC50 | 265.0 | 0.05176 |

| | huPD1- | huPD+ |
|---|---|---|
| EC50 | ~ 1674744 | 0.1063 |

| | huPD1- | huPD1+ |
|---|---|---|
| EC50 | 83.28 | 0.1374 |

INTERLEUKIN-2 MUTANT AND FUSION PROTEIN THEREOF

CROSS-REFERENCE TO RELATED PATENT APPLICATIONS

This application is a continuation of U.S. patent application Ser. No. 18/693,453 filed Nov. 25, 2024, which is a U.S. National Stage Application under 35 U.S.C. § 371 of International Patent Application No. PCT/CN2022/120265 filed Sep. 21, 2022, which claims priority to Chinese Patent Application number 202111110032.3 filed Sep. 22, 2021, all of which are incorporated by reference in their entireties.

INCORPORATION-BY-REFERENCE OF SEQUENCE LISTING

The application contains a sequence listing which has been submitted electronically in XML format and is hereby incorporated by reference in its entirety. Said XML copy, created on Oct. 21, 2025, is named 11275-012477-US1_SL.xml and is 48,798 bytes in size.

TECHNICAL FIELD

The present invention relates to a novel interleukin-2 (IL-2) mutant protein and use thereof. In particular, the present invention relates to an IL-2 mutant protein that has improved properties, such as an improved binding property to an IL-2 receptor and improved druggability, compared to a wild-type IL-2. The present invention further provides a fusion protein, a dimer and an immunoconjugate comprising the IL-2 mutant protein, a nucleic acid encoding the IL-2 mutant protein, the dimer and the immunoconjugate, and a vector and a host cell comprising the nucleic acid. More specifically, the present invention provides an immunoconjugate comprising the IL-2 mutant protein and an anti-PD-1 antibody. The present invention further provides a method for preparing the IL-2 mutant protein, the fusion protein, the dimer and the immunoconjugate, a pharmaceutical composition comprising same, and therapeutic use.

BACKGROUND

Interleukin-2 (IL-2), also known as T-cell growth factor (TCGF), is a multifunctional cytokine produced mainly by activated T cells, particularly by $CD4^+$ T helper cells. In eukaryotic cells, human IL-2 (uniprot: P60568) is synthesized as a precursor polypeptide of 153 amino acids, and mature secretory IL-2 is produced after removal of 20 N-terminus amino acids. The sequences of IL-2 from other species have also been disclosed. See NCBI Ref Seq No. NP032392 (mice), NP446288 (rats) or NP517425 (chimpanzees).

Interleukin-2 has 4 antiparallel and amphipathic a helices, which form a quaternary structure essential for its function (Smith, *Science* 240, 1169-76 (1988); Bazan, *Science* 257, 410-413 (1992)). In most cases, IL-2 acts through three different receptors: interleukin-2 receptor α (IL-2Rα; CD25), interleukin-2 receptor β (IL-2Rβ; CD122), and interleukin-2 receptor γ (IL-2Rγ; CD132). IL-2Rβ and IL-2Rγ are critical for IL-2 signaling, while IL-2Rα (CD25) is not essential for signaling but can enable IL-2 to bind to a receptor with high affinity (Krieg et al., *Proc Natl Acad Sci* 107,11906-11 (2010)). The trimeric receptor (IL-2Rαβγ) formed by the combination of IL-2Rα, IL-2Rβ, and IL-2Rγ is an IL-2 high-affinity receptor (with a $K_D$ of about 10 pM), the dimeric receptor (IL-2Rβγ) consisting of IL-2Rβ and IL-2Rγ is an intermediate-affinity receptor (with a $K_D$ of about 1 nM), and the IL-2 receptor formed solely by subunit α is a low-affinity receptor.

Immune cells express dimeric ortrimeric IL-2 receptors. The dimeric receptor is expressed on cytotoxic $CD8^+$ T cells and natural killer cells (NK), whereas the trimeric receptor is expressed predominantly on activated lymphocytes and $CD4^+$ $CD25^+$ $FoxP3^+$ suppressive regulatory T cells (Treg) (Byman, O. and Sprent. J. *Nat. Rev. Immunol.* 12, 180-190 (2012)). Effector T cells and NK cells in a resting state are relatively insensitive to IL-2 because they do not have CD25 on the cell surface. However, Treg cells consistently express the highest level of CD25 in vivo, and therefore normally IL-2 would preferentially stimulate Treg cell proliferation.

IL-2 mediates multiple actions in an immune response by binding to IL-2 receptors on different cells. In one aspect, IL-2 has a stimulatory effect on the immune system, stimulating the proliferation and differentiation of T cells and natural killer (NK) cells. Therefore, IL-2 has been approved as an immunotherapeutic agent for the treatment of cancer and chronic viral infections. In another aspect, IL-2 also contributes to the maintenance of immunosuppressive $CD4^+$ $CD25^+$ regulatory T cells (i.e., Treg cells) (Fontenot et al., *Nature Immunol* 6, 1142-51 (2005); D'Cruz and Klein, *Nature Immunol* 6, 1152-59 (2005); Maloy and Powrie, *Nature Immunol* 6, 1171-72 (2005)), causing immunosuppression due to activated Treg cells in patients.

In addition, from years of clinical practical experience, it has been found that although high doses of IL-2 can provide significant clinical efficacy in the treatment of cancer such as melanoma and kidney cancer, they can also cause drug-related serious toxic side effects including cardiovascular toxicities such as vascular leak syndrome and hypotension. Studies have shown that these toxicities most likely result from the over-activation of lymphocytes (especially T cells and NK cells) by IL-2, which stimulates the release of inflammatory factors. For example, this can cause vascular endothelial cells to contract, increasing intercellular gaps, causing the extravasation of tissue fluid and thus causing the vascular leak side effect.

Another limiting problem with the clinical use of IL-2 is that it is difficult to administer drugs due to its extremely short half-life. As an IL-2 molecule weighs only 15 KDa, it will be eliminated primarily by glomerular filtration, having a half-life of only about 1 hour in the human body. In order to achieve a sufficiently high exposure in the human body, a large dose of IL-2 is clinically required to be infused every 8 hours. However, frequent dosing places a heavy burden on patients, and more importantly, infusion of large doses of IL-2 can cause high peak plasma concentrations ($C_{max}$), which is probably another critical factor contributing to drug toxicity.

Several approaches have been adopted to overcome these problems associated with IL-2 immunotherapy. For example, a combination of IL-2 with certain anti-IL-2 monoclonal antibodies has been found to enhance the therapeutic effect of IL-2 in vivo (Kamimura et al., *J. Immunol.,* 177, 306-14 (2006); Boyman et al., *Science,* 311, 1924-27 (2006)). Some schemes for engineering IL-2 molecules have also been proposed. For example, Helen R. Mott et al. disclosed a mutant protein of human IL-2, F42A, which has an eliminated ability to bind to IL-2Rα. Rodrigo Vazquez-Lombardi et al. (*Nature Communications,* 8:15373, DOI: 10.1038/ncomms15373) have also proposed a triple mutant human IL-2 mutant protein $IL\text{-}2^{3X}$ with an eliminated ability to bind to IL-2Rα, which has residue mutations R38D+

K43E+E61R at amino acid residue positions 38, 43 and 61, respectively. CN1309705A discloses mutations at positions D20, N88 and Q126 that result in reduced binding of IL-2 to IL-2Rβγ. These mutant proteins are still deficient in their pharmacokinetic and/or pharmacodynamic properties and also confronted with low expression yields and/or poor molecular stability when expressed in mammalian cells.

Programmed cell death protein 1(PD-1 or CD279) is an inhibitory member of the CD28 receptor family, which further includes CD28, CTLA-4, ICOS and BTLA. PD-1 is a cell surface receptor and is expressed on activated B cells, T cells and myeloid cells. PD-1 is structurally a monomeric type 1 transmembrane protein, consisting of an immunoglobulin variable-like extracellular domain and a cytoplasmic domain comprising an immunoreceptor tyrosine-based inhibitory motif (ITIM) and an immunoreceptor tyrosine-based switch motif (ITSM). Two ligands for PD-1, PD-L1 and PD-L2, have been identified, which have been shown to down-regulate the activation of T cells after binding to PD-1. Both PD-L1 and PD-L2 are B7 homologs that bind to PD-1 but not to other members of the CD28 family. PD-L1, one ligand for PD-1, is abundant in various human cancers. The interaction between PD-1 and PD-L1 results in a decrease in tumor infiltrating lymphocytes, a decrease in T cell receptor-mediated proliferation, and immune escape of cancerous cells.

Various antibodies that bind to PD-1 are known in the art, such as PD-1 antibodies disclosed in WO2017024465A1.

Therefore, there is a need in the art to further develop new IL-2 molecules with improved properties (e.g., reduced binding to their receptors, improved druggability, and the like), particularly immunoconjugates with PD-1 antibodies.

SUMMARY

The present invention relates to the following embodiments:

1. An immunoconjugate, comprising (i) an antibody binding to PD-1 and (ii) an IL-2 mutant protein, wherein the mutant protein, compared to wild-type IL-2 (preferably human IL-2, and more preferably IL-2 comprising a sequence set forth in SEQ ID NO: 3), comprises mutations:

(i) a mutation that eliminates or reduces the binding affinity for an IL-2Rα receptor, at a binding interface of IL-2 to IL-2Rα, particularly at positions 35 and/or 42; and/or (ii) a mutation that weakens the binding to an IL-2Rβγ receptor, at a binding interface of IL-2 to IL-2Rβγ, particularly at at least one position selected from positions 88, 127 and/or 130; and (iii) a shortened B'C' loop region (i.e., a sequence linking amino acid residues aa72 and aa84), wherein preferably, the shortened loop region has less than 10, 9, 8, 7, 6 or 5 amino acids in length, and more preferably has 7 amino acids in length; preferably, the shortened B'C' loop region leads to an improved protein expression yield and/or purity; and optionally (iv) a mutation that removes an O-glycan modification at the N-terminus of IL2, particularly at position 3 of the N-terminus of IL-2, and the amino acid positions are numbered according to SEQ ID NO: 3.

2. The immunoconjugate according to embodiment 1, wherein the mutant protein, relative to the wild-type IL-2, comprises:

(i) N88D;
N88R;

$$N88R+S130R;$$

$$F42A+N88R+S127E;$$

$$F42A+N88R+S127E; \text{ or}$$

$$K35E+N88R+S127E;$$

and (ii) a B'C' loop region sequence AGDASIH or AQSKNFH;

and optionally (iii) T3A.

3. The immunoconjugate according to embodiment 1, wherein the IL-2 mutant protein comprises or consists of an amino acid sequence set forth in SEQ ID NO: 4, 23, 25, 27, 29 or 31 or an amino acid sequence having at least 90%, 91%, 92%, 93%, 94%, 95%, 96%, 97%, 98% or 99% identity thereto.

4. The immunoconjugate according to any one of embodiments 1-3, wherein the immunoconjugate comprises:

a first monomer comprising an IL-2 mutant protein fused to an Fc fragment; and a second monomer comprising an antibody or a fragment thereof that specifically binds to PD-1, wherein preferably, the fragment comprises one heavy chain and one light chain of the anti-PD-1 antibody.

5. The immunoconjugate according to embodiment 4, wherein the Fc fragment in the first monomer comprises a Knob mutation, and the antibody heavy chain in the second monomer comprises a hole mutation; or the Fc fragment in the first monomer comprises a hole mutation, and the antibody heavy chain in the second monomer comprises a Knob mutation.

6. The immunoconjugate according to embodiment 4 or 5, wherein the Fc fragment in the first monomer is an Fc fragment of IgG1, IgG2, IgG3 or IgG4, preferably comprising or consisting of an amino acid sequence set forth in SEQ ID NO: 6, 42 or 43.

7. The immunoconjugate according to any one of embodiments 4-6, wherein the IL-2 mutant protein fused to the Fc fragment comprises or consists of an amino acid sequence set forth in SEQ ID NO: 7, 24, 26, 28, 30 or 32 or an amino acid sequence having at least 90%, 91%, 92%, 93%, 94%, 95%, 96%, 97%, 98% or 99% identity thereto.

8. The immunoconjugate according to any one of embodiments 4-7, wherein the PD-1 antibody or the antigen-binding fragment thereof comprises a heavy chain comprising a heavy chain variable region, wherein the heavy chain variable region comprises HCDR1, HCDR2 and HCDR3 set forth in amino acid sequences of SEQ ID NOs: 9, 10 and 11, respectively.

9. The immunoconjugate according to any one of embodiments 4-8, wherein the PD-1 antibody or the antigen-binding fragment thereof comprises a light chain comprising a light chain variable region, wherein the light chain variable region comprises LCDR1, LCDR2 and LCDR3 set forth in amino acid sequences of SEQ ID NOs: 16, 17 and 18, respectively.

10. The immunoconjugate according to any one of embodiments 4-9, wherein the anti-PD-1 antibody or the antigen-binding fragment thereof comprises:

a heavy chain variable region comprising or consisting of an amino acid sequence set forth in SEQ ID NO: 8 or an amino acid sequence having at least 90%, 91%, 92%, 93%, 94%, 95%, 96%, 97%, 98% or 99% identity thereto; and a light chain variable region comprising or consisting of an amino acid sequence set forth in SEQ ID NO: 15 or an amino acid sequence having at least 90%, 91%, 92%, 93%, 94%, 95%, 96%, 97%, 98% or 99% identity thereto.

11. The immunoconjugate according to any one of embodiments 4-9, wherein the anti-PD-1 antibody or the antigen-binding fragment thereof comprises:

a heavy chain comprising or consisting of an amino acid sequence set forth in SEQ ID NO: 14 or 22 or an amino acid sequence having at least 85%, 90%, 91%, 92%, 93%, 94%, 95%, 96%, 97%, 98% or 99% identity thereto; and a light chain comprising or consisting of an amino acid sequence set forth in SEQ ID NO: 20 or an amino acid sequence having at least 85%, 90%, 91%, 92%, 93%, 94%, 95%, 96%, 97%, 98% or 99% identity thereto.

12. The immunoconjugate according to any one of embodiments 1-11, wherein the IL-2 mutant protein is linked to Fc via a linker, or the IL-2 mutant protein is linked to the anti-PD-1 antibody via a linker, and preferably, the linker is $(GGGGS)_n$, wherein n=1, 2, 3 or 4, for example, the linker is set forth in SEQ ID NO: 5.

13. An isolated polynucleotide, encoding one or more chains, or the first monomer and/or the second monomer in the immunoconjugate according to any one of embodiments 1-12.

14. An expression vector, comprising the polynucleotide according to embodiment 13.

15. A host cell, comprising the polynucleotide according to embodiment 13 or the vector according to embodiment 14, wherein preferably, the host cell is a yeast cell or a mammalian cell, particularly an HEK293 cell or a CHO cell.

16. A method for producing the immunoconjugate according to any one of embodiments 1-12, comprising culturing the host cell according to embodiment 15 under conditions suitable for expression of the immunoconjugate.

17. A pharmaceutical composition, comprising the immunoconjugate according to any one of embodiments 1-12, and optionally a pharmaceutical supplementary material.

18. Use of the immunoconjugate according to any one of embodiments 1-12 or the pharmaceutical composition according to embodiment 17 in the manufacture of a medicament for preventing and/or treating cancer, wherein preferably, the cancer is a solid tumor or a hematological tumor, e.g., a gastrointestinal tumor or melanoma, such as colorectal cancer or colon cancer; for example, the cancer is a PD-1 antibody treatment-resistant cancer.

19. The use according to embodiment 18, wherein the pharmaceutical composition further comprises a second therapeutic agent.

20. A method for preventing and/or treating cancer in a subject, comprising administering to the subject the immunoconjugate according to any one of embodiments 1-12 or the pharmaceutical composition according to embodiment 17, wherein preferably, the cancer is a solid tumor or a hematological tumor, e.g., a gastrointestinal tumor or melanoma, such as colorectal cancer or colon cancer; for example, the cancer is a PD-1 antibody treatment-resistant cancer.

21. The method according to embodiment 20, wherein the mutant protein, the fusion protein or the pharmaceutical composition is administered in a combination therapy with a second therapeutic agent.

SUMMARY

I. Definitions

Figure 1A:
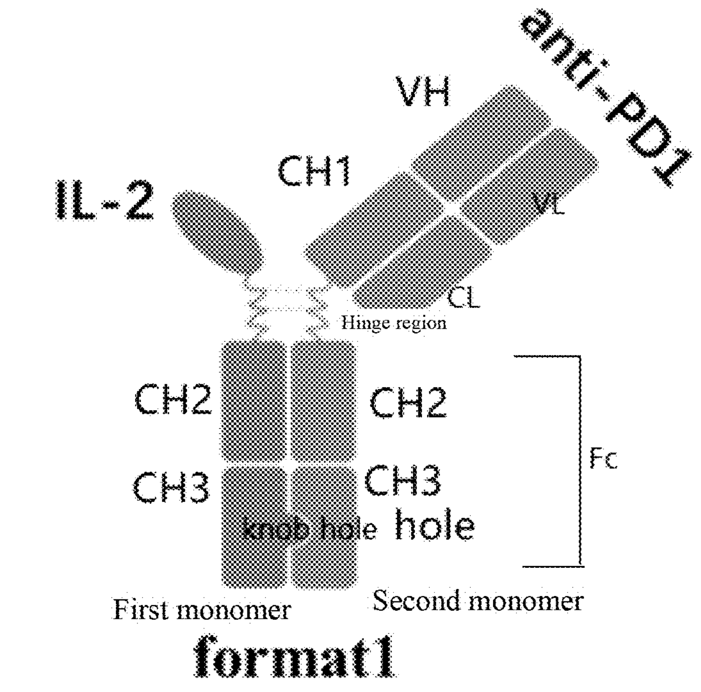
FIG. 1A shows the molecular structure of an immunoconjugate of anti-PD-1 and an IL-2 mutant of the present invention.

Before the present invention is described in detail below, it should be understood that the present invention is not limited to the particular methodology, protocols, and reagents described herein, as these may vary. It should also be understood that the terminology used herein is only intended to describe specific embodiments rather than limit the scope of the present invention, which will be limited only by the appended claims. Unless otherwise defined, any technical and scientific term used herein has the same meaning as commonly understood by those of ordinary skill in the art to which the present invention belongs.

For the purpose of explaining this specification, the following definitions will be used, and wherever appropriate, terms used in the singular form may also include the plural form, and vice versa. It should be understood that the terms used herein are for the purpose of describing specific embodiments only, and are not intended to be limiting.

The term "about" used in combination with a numerical value is intended to encompass the numerical values in a range from a lower limit less than the specified numerical value by 5% to an upper limit greater than the specified numerical value by 5%.

As used herein, the term "and/or" refers to any one of the options or any two or more of the options. As used herein, the term "comprise" or "include" is intended to mean that the elements, integers, or steps are included, but not to the exclusion of any other elements, integers, or steps. The term "comprise" or "include" used herein, unless indicated otherwise, also encompasses the situation where the entirety consists of the described elements, integers, or steps. For example, when referring to an IL-2 mutant protein "comprising" or "including" a mutation or a combination of mutations, it is also intended to encompass IL-2 mutant proteins having only the mutation or the combination of mutations. As used herein, wild-type "interleukin-2" or "IL-2" refers to a parent IL-2 protein, preferably a naturally occurring IL-2 protein, e.g., a native IL-2 protein derived from a human, mouse, rat, or non-human primate, serving as a template to which a mutation or a combination of mutations disclosed herein is introduced, including both unprocessed (e.g., without the removal of a signal peptide) and processed (e.g., with the removal of a signal peptide) forms. A full-length native human IL-2 sequence comprising a signal peptide is shown in SEQ ID NO: 1 and the sequence of its mature protein is shown in SEQ ID NO: 2. In addition, this term includes naturally occurring allelic and splice variants, isotypes, homologs, and species homologs of IL-2. This term also includes variants of native IL-2, which may, for example, have at least 95%-99% or more identity to the native IL-2 or have no more than 1-10 or 1-5 amino acid mutations (e.g., conservative substitutions) and preferably have substantially the same binding affinity for IL-2Rα and/or IL2Rβγ as the native IL-2 protein. Therefore, in some embodiments, compared to the native IL-2 protein, the wild-type IL-2 protein may comprise amino acid mutations that do not affect its binding to the IL-2 receptor. For example, a native human IL-2 protein (uniprot: P60568) with a mutation C125S introduced at position 125 is a wild-type IL-2 protein disclosed herein. An example of a wild-type human IL-2 protein comprising the C125S mutation is set forth in SEQ ID NO: 3. In some embodiments, the wild-type IL-2 sequence may have at least more than 85% or 95%, or even at least 96%, 97%, 98%, or 99% amino acid sequence identity to the amino acid sequence set forth in SEQ ID NOs: 1, 2, or 3.

As used herein, the amino acid mutation may be an amino acid substitution, deletion, insertion, and addition. Any combination of substitution, deletion, insertion and addition may be made to obtain a final mutant protein construct with the desired properties, such as reduced binding affinity for IL-2Rα and/or improved druggability and/or weakened IL-2Rβγ. Amino acid deletions and insertions include amino- and/or carboxyl-terminal deletions and insertions of a polypeptide sequence, as well as deletions and insertions within the polypeptide sequence. For example, an alanine residue can be deleted at position 1 of a full-length human IL-2, or one or more amino acids can be deleted from a B'C' loop region to shorten the length of the loop region. In some embodiments, the preferred amino acid mutations are amino acid substitutions, e.g., the combination of single amino acid substitutions or the replacement of segments of an amino acid sequence. For example, the entirety or a part of the B'C' loop region sequence of the wild-type IL-2 can be replaced with a different sequence (such as a B'C' loop of IL-15), preferably to obtain a shortened B'C' loop region sequence.

In the present invention, when an amino acid position in the IL-2 protein or IL-2 sequence segment is mentioned, it is determined by reference to an amino acid sequence set forth in SEQ ID NO: 3 of the wild-type human IL-2 protein (also referred to as IL-$2^{WT}$). The corresponding amino acid position in other IL-2 proteins or polypeptides (including full-length sequences or truncated fragments) can be identified by amino acid sequence alignment with SEQ ID NO: 3. Therefore, in the present invention, unless otherwise stated, an amino acid position in an IL-2 protein or polypeptide is an amino acid position numbered according to SEQ ID NO: 3. For example, when mentioning "F42", it refers to a phenylalanine residue F at position 42 of SEQ ID NO: 3, or an amino acid residue at corresponding positions of other IL-2 polypeptide sequences by alignment. In addition, for ease of understanding and comparison, when the mutations of the present invention involve site truncation or deletion of certain specific segments (e.g., the sequence of the B'C' loop region, i.e., 11 amino acid residues at positions 73-83 of SEQ ID NO: 3), the numbering of the amino acid residues outside this region remains unchanged given that a specific mutation region and a mode of the mutation have been determined. For example, after the sequence of the B'C' loop region, i.e., 11 amino acid residues at positions 73-83 of SEQ ID NO: 3, is truncated to 7 amino acid residues, numbers 80-83 are no longer assigned, and the position of the next amino acid residue immediately following the B'C' loop region is still 84. To perform a sequence alignment for determining an amino acid position, Basic Local Alignment Search Tool available at https://blast.ncbi.nlm.nih.gov/Blast.cgi can be used with default parameters.

When an IL-2 mutant protein is mentioned herein, a single amino acid substitution is described as [original amino acid residue/position/amino acid residue for substitution]. For example, the substitution of lysine at position 35 with glutamate can be indicated as K35E. When there are multiple optional amino acid substitutions (e.g., D and E) at a given position (e.g., K35), the amino acid substitutions can be indicated as K35D/E. Correspondingly, single amino acid substitutions can be linked together by "+" or "−" to indicate a combinatorial mutation at multiple given positions. For example, the combinatorial mutation at positions F42A, N88R and S127E can be denoted as: F42A+N88R+S127E or F42A-N88R-S127E.

As used herein, the "percent sequence identity" can be determined by comparing two optimally aligned sequences over a comparison window. Preferably, the sequence identity is determined over the full length of a reference sequence (e.g., SEQ ID NO: 3). Methods of sequence alignment for comparison are well known in the art. Algorithms suitable for determining the percent sequence identity include, for example, BLAST and BLAST 2.0 algorithms (see Altschul et al., *Nuc. Acids Res.* 25: 3389-402, 1977 and Altschul et al., *J. Mol. Biol.* 215: 403-10, 1990). Software for performing BLAST analysis is publicly available from the National Center for Biotechnology Information. For the purpose of the present application, the percent identity can be determined by using Basic Local Alignment Search Tool available at https://blast.ncbi.nlm.nih.gov/Blast.cgi with default parameters.

As used herein, the term "conservative substitution" refers to an amino acid substitution that does not adversely affect or alter the biological function of a protein/polypeptide comprising an amino acid sequence. For example, aaconservative substitution may be introduced by standardtechniques known in the art, such as site-directed mutagenesis and PCR-mediated mutagenesis. A typical conservative amino acid substitution refers to a substitution of an amino acid with another amino acid having similar chemical properties (e.g., charge or hydrophobicity). Conservative replacement tables of functionally similar amino acids are well known in the art. In the present invention, residues for conservative substitutions are from the conservative substitution table X below, particularly from the preferred residues for conservative amino acid substitutions in Table X.

TABLE X

| Original residue | Exemplary substitution | Preferred conservative amino acid substitution |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Nle | Leu |
| Leu (L) | Nle; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Nle | Leu |

For example, relative to one of SEQ ID NOs: 1-3, the wild-type IL-2 protein may have conservative amino acid substitutions, or only have conservative amino acid substitutions; and in one preferred embodiment, the conservative substitutions involve no more than 10 amino acid residues, e.g., 1, 2, 3, 4, 5, 6, 7, 8, 9 or 10 residues. For another example, relative to the IL-2 mutant protein sequences specifically given herein (e.g., any one of SEQ ID NOs: 4, 23, 25, 27, 29 and 31), the IL-2 mutant protein disclosed herein may have conservative amino acid substitutions, or only have conservative amino acid substitutions; and in one preferred embodiment, the conservative substitutions involve no more than 10 amino acid residues, e.g., 1, 2, 3, 4, 5, 6, 7, 8, 9 or 10 residues.

"Affinity" or "binding affinity" refers to the inherent binding ability that reflects the interaction between members of a binding pair. The affinity of a molecule X for its binding partner Y can be represented by an equilibrium dissociation constant ($K_D$), which is the ratio of a dissociation rate constant ($k_{dis}$) to an association rate constant ($k_{on}$). The binding affinity can be measured by common methods known in the art. One specific method for measuring the affinity is the SPR affinity assay technique or BLI assay technique described herein.

Herein, an antigen-binding molecule is a polypeptide molecule that can specifically bind to an antigen, e.g., an immunoglobulin molecule, an antibody, or an antibody fragment (e.g., a Fab fragment and an scFv fragment). In one embodiment, the antigen-binding molecule of the present invention is a binding molecule, such as an antibody, e.g., a monoclonal antibody, directed against an immune checkpoint molecule as an antigen. In one embodiment, the immune checkpoint molecule is PD-1, PD-L1 or PD-L2.

As used herein, an antibody Fc fragment refers to a C-terminus region of an immunoglobulin heavy chain that contains at least a portion of the constant region, and may include Fc fragments of native sequences and variant Fc fragments. Fc fragments of native sequences encompass various naturally occurring Fc sequences of immunoglobulins, such as the Fc regions of various Ig subclasses or allotypes thereof (Gestur Vidarsson et al., IgG subclasses and allotypes: from structure to effector functions, 20 Oct. 2014, doi: 10.3389/fimmu.2014.00520.). In one embodiment, the heavy chain Fc fragment of human IgG extends from Cys226 or Pro230 of the heavy chain to the carboxyl terminus. In another embodiment, the C-terminus lysine (Lys447) of the Fc fragment may or may not be present. In other embodiments, the Fc fragment is a variant Fc fragment comprising a mutation, for example, a L234A-L235A mutation. Unless otherwise indicated herein, amino acid residues in the Fc fragment are numbered according to the EU numbering system, also called the EU index, as described in Kabat, E. A. et al., *Sequences of Proteins of Immunological Interest,* $5^{th}$ Ed., Public Health Service, National Institutes of Health, Bethesda, MD (1991), NIH Publication 91-3242. In some embodiments, the antibody Fc fragment may carry an IgG1 hinge sequence or a portion of the IgG1 hinge sequence at the N-terminus, e.g., the sequence of E216 to T225 or the sequence of D221 to T225 according to the EU numbering. Mutations may be contained in the hinge sequence.

The IL-2 protein is a member of the short chain type I cytokine family with four α-helical bundles (A, B, C, and D). As used herein, the terms "B'C' loop", "B'C' loop region" and "B'C' loop sequence" are used interchangeably, referring to a linker sequence between the B and C helices of the IL-2 protein. The B'C' loop sequence of an IL-2 protein can be determined by performing analysis of the IL-2 crystal structure (e.g., PDB: 2ERJ). For the purpose of the present invention, according to the numbering of SEQ ID NO: 3, the B'C' loop sequence refers to a sequence linking the residue at position 72 to the residue at position 84 in the IL-2 polypeptide. In the wild-type IL-2 proteins set forth in SEQ ID NOs: 1, 2 and 3, the linker sequence comprises 11 amino acids, namely A73-R83. Accordingly, as used herein, the term "shortened loop region" or "shortened B'C' loop region" means that a mutant protein has a B'C' loop sequence with a reduced length relative to the wild-type IL-2 protein, i.e., the linker sequence between the amino acid residues aa72 and aa84 is shortened according to the numbering of SEQ ID NO: 3. "Shortened loop region" may be achieved by replacement or truncation of the loop sequence. The replacement or truncation may occur in any region or portion of the B'C' loop sequence. For example, the replacement or truncation may be the replacement of the sequence A73-R83 in the loop region (e.g., the replacement with a B'C loop region of IL-15) or the truncation of the sequence by one or more amino acid residues at the C-terminus. For another example, the replacement or truncation may be the replacement of the sequence Q74-R83 in the loop region or the truncation of the sequence by one or more amino acid residues at the C-terminus. After the replacement or truncation, if necessary, a single amino acid substitution, e.g., an amino acid substitution for eliminating glycosylation and/or a reverse mutation, can be further introduced into the loop region sequence to further improve the performance of the mutant protein, e.g., the druggability. Therefore, herein, the mutated shortened B'C' loop region can be described through a sequence linking the residue at position 72 to the residue at position 84 after a mutation is introduced.

As used herein, "IL-2Rα binding interface" mutation refers to a mutation that occurs at amino acid sites where IL-2 interacts with IL-2Rα (i.e., CD25). These interaction sites can be determined by analyzing the crystal structure of the complex of IL-2 and its receptor (e.g., PDB: 1Z92). In some embodiments, the mutation refers particularly to mutations in the region of amino acid residues 35-72 of IL-2, particularly to mutations at the following amino acid sites: 35, 37, 38, 41, 42, 43, 45, 61, 62, 68 and 72. Preferably, an IL-2 protein comprising the mutation has reduced or eliminated binding to IL-2Rα compared to the corresponding protein before introduction of the mutation.

As used herein, an "IL-2βγ binding interface" mutation refers to a mutation that occurs at amino acid sites where IL-2 interacts with IL-2Rβγ (i.e., CD122 and CD132). These interaction amino acid sites can be determined by analyzing the crystal structure of the complex of IL-2 and its receptor (e.g., PDB: 2ERJ). In some embodiments, the mutation refers particularly to mutations in the regions of amino acid residues 12-20, 84-95 and 126-130 of IL-2, particularly to mutations at the following amino acid sites: 12, 15, 16, 19, 20, 84, 87, 88, 91, 92, 95, 126, 127 and 130. Preferably, an IL-2 protein comprising the mutation has weakened binding to IL-2Rβγ compared to the corresponding protein before introduction of the mutation.

As used herein, with respect to binding to an IL-2Rβγ receptor, a "weakened" IL-2 protein molecule means introducing a mutation into a binding interface to IL-2Rβγ that leads to reduced binding affinity for the IL-2Rβγ receptor relative to the corresponding IL-2 protein before the introduction of the mutation. Further preferably, the weakened molecule has reduced activation activity for T cells (e.g., $CD8^+$ T cells or $CD4^+$ T cells) and/or NK cells relative to the corresponding protein. For example, by measuring the ratio of $EC_{50}$ values of activation of pSTAT5 signals in T cells by the weakened molecule and the corresponding protein, the activation activity may be reduced by 5 times or more, e.g., 10 times or more, or 50 times or more, or 100 times or more, or even 1000 times or more. For example, the activation activity ofthe weakened molecule for T cells can be reduced by 10-50 times, or 50-100 times, or 100-1000 times, or more, relative to the corresponding protein. Thus, in the present invention, in some embodiments, the weakened molecule of the present invention has "weakened" binding affinity for the IL-2Rβγ receptor and "weakened" activation activity for T cells.

"Antigen-binding fragment" refers to a molecule different from an intact antibody, which comprises a portion of the intact antibody and binds to an antigen to which the intact antibody binds. Examples of the antibody fragments include, but are not limited to, Fv, Fab, Fab', Fab'-SH, $F(ab')_2$, a domain antibody (dAb), a linear antibody, a single-chain antibody (e.g., scFv), a single-domain antibody (e.g., VHH), a bi-valent antibody or a fragment thereof, or a camelid antibody.

The term "antigen" refers to a molecule that induces an immune response. Such an immune response may involve antibody production or activation of specific immune cells, or both. Those skilled will understand that any macromolecules, including essentially all proteins or peptides, can be used as antigens. In addition, an antigen may be derived from recombinant or genomic DNA. In some embodiments, the antigen as described herein is a tumor-associated antigen, i.e., an antigen associated with the occurrence, development, or progression of a tumor, e.g., PD-1, PD-L1, or PD-L2.

"Complementarity determining region" or "CDR region" or "CDR" is a region in an antibody variable domain that is highly variable in sequence and forms a structurally defined loop ("hypervariable loop") and/or comprises antigen-contacting residues ("antigen contact sites"). CDRs are primarily responsible for binding to antigen epitopes. The CDRs of the heavy and light chains are generally referred to as CDR1, CDR2, and CDR3, and are numbered sequentially from the N-terminus. The CDRs located in the heavy chain variable domain of the antibody are referred to as HCDR1, HCDR2, and HCDR3, whereas the CDRs located in the light chain variable domain of the antibody are referred to as LCDR1, LCDR2, and LCDR3. In a given amino acid sequence of a light chain variable region or a heavy chain variable region, the exact amino acid sequence boundary of each CDR can be determined using any one or a combination of many well-known antibody CDR assignment systems including, e.g., Chothia based on the three-dimensional structure of antibodies and the topology of the CDR loops (Chothia et al. (1989) *Nature* 342: 877-883; Al-Lazikani et al., *Standard conformations for the canonical structures of immunoglobulins, Journal of Molecular Biology,* 273: 927-948 (1997)), Kabat based on antibody sequence variability (Kabat et al., *Sequences of Proteins of Immunological Interest,* $4^{th}$ Ed., U.S. Department of Health and Human Services, National Institutes of Health (1987)), AbM (University of Bath), Contact (University College London), International ImMunoGeneTics database (IMGT) (imgt.cines.fr/ on the World Wide Web), and North CDR definition based on the affinity propagation clustering using a large number of crystal structures.

For example, according to different CDR determination schemes, the residues of each CDR are described as follows.

| CDR | Kabat scheme | AbM scheme | Chothia scheme | Contact scheme |
|---|---|---|---|---|
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1 | H31-H35B | H26-H35B | H26-H32 | H30-H35B |

-continued

| CDR | Kabat scheme | AbM scheme | Chothia scheme | Contact scheme |
|---|---|---|---|---|
| (Kabat numbering system) | | | | |
| HCDR1 | H31-H35 | H26-H35 | H26-H32 | H30-H35 |
| (Chothia numbering system) | | | | |
| HCDR2 | H50-H65 | H50-H58 | H53-H55 | H47-H58 |
| HCDR3 | H95-H102 | H95-H102 | H96-H101 | H93-H101 |
| (Kabat numbering system) | | | | |

CDRs can also be determined based on having the same Kabat numbering positions as a reference CDR sequence (e.g., any of the exemplary CDRs of the present invention).

Unless otherwise stated, the term “CDR” or “CDR sequence” used herein encompasses CDR sequences determined by any one of the schemes described above.

Unless otherwise stated, residue positions of an antibody variable region (including heavy chain variable region residues and light chain variable region residues) are numbered according to the Kabat numbering system (Kabat et al., *Sequences of Proteins of Immunological Interest,* $5^{th}$ Ed. Public Health Service, National Institutes of Health, Bethesda, Md. (1991)).

In one embodiment, the CDRs in the heavy chain variable region and the light chain variable region of the antibody of the present invention are CDR sequences defined according to the North numbering scheme.

The term “linker” as used herein refers to any molecule that enables a direct linkage of different portions of a fusion protein. Examples of linkers to establish covalent linkages between different portions of a fusion protein include peptide linkers and non-proteinaceous polymers including, but not limited to, polyethylene glycol (PEG), polypropylene glycol, polyalkylene oxide and copolymers of polyethylene glycol and polypropylene glycol. The term “peptide linker” according to the present invention refers to an amino acid sequence that links the amino acid sequence of a first moiety of a fusion protein to a second moiety of the fusion protein. For example, a peptide linker may link an IL-2 moiety of a fusion protein to an Fc domain or a fragment thereof. For example, a peptide linker may also link an antibody to IL-2, such as linking the C-terminus of an antibody heavy chain to IL-2. Preferably, the peptide linker has a length sufficient to link two entities in a manner that maintains their conformation relative to each other without interference with the desired activities. The peptide linker may or may not predominantly comprise the following amino acid residues: Gly, Ser, Ala or Thr. Useful linkers include glycine-serine polymers including, for example, (GS)n, (GSGGS)n, (GGGGS)n, (GGGS)n and (GGGGS)nG, wherein n is an integer of at least 1 (and preferably 2, 3, 4, 5, 6, 7, 8, 9, or 10). Useful linkers also include glycine-alanine polymers, alanine-serine polymers, and other flexible linkers. Preferably, the linker of the present invention is (GGGGS)n, wherein n=1, 2, 3, 4 or 5, preferably 2. Preferably, the linker of the present invention is set forth in SEQ ID NO: 5.

“Antibody in the form of IgG” refers to the heavy chain constant region of the antibody belonging to the IgG form. Heavy chain constant regions of all antibodies of the same type are identical, and heavy chain constant regions of antibodies of different types are different. For example, an antibody in the form of IgG4 means that the heavy chain constant region of the antibody is from IgG4, or an antibody in the form of IgG1 means that the heavy chain constant region of the antibody is from IgG1.

“Humanized” antibody refers to an antibody comprising amino acid residues from non-human CDRs and amino acid residues from human FRs. In some embodiments, a humanized antibody will comprise at least one, or generally two of substantially all variable domains in which all or substantially all CDRs (e.g., CDRs) correspond to those of a non-human antibody, and all or substantially all FRs correspond to those of a human antibody. A humanized antibody may optionally comprise at least a portion of an antibody constant region derived from a human antibody. The “humanized form” of an antibody (such as a non-human antibody) refers to an antibody that has been humanized.

“Human antibody”, “fully human antibody” and “fully humanized antibody” are used interchangeably, and refer to an antibody having an amino acid sequence which corresponds to the amino acid sequence of an antibody generated by a human or human cell or derived from a non-human source that utilizes human antibody libraries or other human antibody encoding sequences. This definition of a human antibody explicitly excludes humanized antibodies comprising non-human antigen-binding residues. The antibody moiety in the immunoconjugate of the present invention can be a humanized antibody, a human antibody or a chimeric antibody.

The term “fusion” as used herein refers to a fusion formed by linking two or more initially separate proteins/genes/compounds. If the entity constituting the fusion is a protein, it is referred to as a fusion protein. The fusion protein is encompassed within the scope of the fusion of the present application. For example, IL-2 linked to an Fc dimer may constitute an IL-2 fusion protein. The linkage between the two entity molecules constituting the fusion may be achieved with or without a linker.

The term “immunoconjugate” as used herein refers to a polypeptide molecule comprising at least one IL-2 molecule and at least one antibody or antibody fragment. As described herein, the IL-2 molecule may be linked to an antibody through various interactions and in various configurations. For example, a fusion protein of IL-2 and Fc and a fragment of an antibody molecule comprising a heavy chain and a light chain may constitute an immunoconjugate by dimerization. Preferably, the immunoconjugate of the present invention has a structure shown in FIG. 1A, or a structure shown in FIG. 1A where the IL-2 moiety is exchanged with the PD-1 antibody moiety.

As used herein, the terms “first” and “second” are used with respect to an Fc domain, a monomer and the like, to facilitate differentiation when there is more than one of each type of module. Unless explicitly stated as such, use of these terms is not intended to confer a particular order or orientation to the immunoconjugate.

The term “therapeutic agent” as described herein encompasses any substance that is effective in preventing or treating a tumor, e.g., cancer, including a chemotherapeutic agent, a cytokine, an angiogenesis inhibitor, a cytotoxic agent, other antibodies, a small molecule drug, or an immunomodulatory agent (e.g., an immunosuppressant).

The term “effective amount” refers to an amount or dosage of the antibody, fragment, composition, or combination of the present invention which generates expected effects in a patient in need of treatment or prevention after administered to the patient in a single or multiple doses. An “effective amount” can encompass a “therapeutically effective amount” or a “prophylactically effective amount”.

"Therapeutically effective amount" refers to an amount effective to achieve a desired therapeutic result at a necessary dose for a necessary period of time. The therapeutically effective amount is also such an amount that any toxic or undesired effect of the antibody, fragment thereof, composition, or combination is inferior to the therapeutically beneficial effect. The "therapeutically effective amount" preferably inhibits a measurable parameter (e.g., tumor volume) by at least about 40%, and even more preferably by at least about 50%, 55%, 60%, 65%, 70%, 75%, 80%, 85%, 90%, or even 100%, relative to untreated subjects. "Prophylactically effective amount" refers to an amount effective to achieve a desired prophylactic result at a necessary dose for a necessary period of time. Generally, since a prophylactic dose is administered in a subject before or at an earlier stage of a disease, a prophylactically effective amount will be less than a therapeutically effective amount.

The terms "host cell", "host cell line" and "host cell culture" are used interchangeably and refer to cells into which exogenous nucleic acids are introduced, including progenies of such cells. Host cells include "transformants" and "transformed cells", which include primary transformed cells and progenies derived therefrom, regardless of the number of passages. Progeny may not be exactly the same as parent cells in terms of nucleic acid content, and may comprise mutations. Mutant progenies having the same function or biological activities that are screened or selected from the initially transformed cells are included herein.

The term "label" used herein refers to a compound or composition which is directly or indirectly conjugated or fused to an agent, such as a polynucleotide probe or an antibody, and facilitates the detection of the agent to which it is conjugated or fused. The label itself can be detectable (e.g., a radioisotope label or a fluorescent label) or can catalyze a chemical change to a detectable substrate compound or composition in the case of enzymatic labeling. The term is intended to encompass direct labeling of a probe or an antibody by coupling (i.e., physical linking) a detectable substance to the probe or an antibody and indirect labeling of a probe or antibody by reacting with another reagent which is directly labeled.

"Individual" or "subject" includes mammals. The mammals include, but are not limited to, domestic animals (e.g., cattle, goats, cats, dogs, and horses), primates (e.g., human and non-human primates such as monkeys), rabbits, and rodents (e.g., mice and rats). In some embodiments, the individual or subject is a human.

The term "anti-tumor effect" refers to a biological effect that can be demonstrated by a variety of means, including but not limited to, for example, decrease in tumor volume, decrease in number of tumor cells, decrease in tumor cell proliferation, or decrease in tumor cell viability. In some embodiments, the anti-tumor effect also relates to an anti-tumor effect without reducing the body weight of the subject. The terms "tumor" and "cancer" are used interchangeably herein and encompass solid and hematological tumors.

The term "cancer" refers to or describes a physiological condition in mammals characterized generally by unregulated cell growth. In certain embodiments, cancers suitable for treatment with the antibody of the present invention include solid tumors or hematological tumors, and the like, including metastatic forms of the cancers. The term "tumor" refers to all neoplastic cell growth and proliferation, whether malignant or benign, and all pre-cancerous and cancerous cells and tissues. The terms "cancer", "carcinoma", and "tumor" are not mutually exclusive when referred to herein.

The term "pharmaceutical supplementary material" refers to diluents, adjuvants (e.g., Freund's adjuvants (complete and incomplete)), excipients, carriers, stabilizers, or the like, that are administered with the active substance.

The term "pharmaceutical composition" refers to a composition that exists in a form allowing effective biological activity of the active ingredient contained therein and does not contain additional ingredients having unacceptable toxicity to a subject to which the composition is administered.

The term "pharmaceutical combination or combination product" refers to a non-fixed combination product or a fixed combination product, including but not limited to, a kit and a pharmaceutical composition. The term "non-fixed combination" means that the active ingredients (e.g., (i) the mutant protein or fusion of the present invention, and (ii) an additional therapeutic agent) are administered, either simultaneously or sequentially (without particular time limitation or at identical or different time intervals), to a patient as separate entities, wherein such administration provides two or more prophylactically or therapeutically effective active agents in the patient. The term "fixed combination" means that two or more active agents are administered to a patient simultaneously in the form of a single entity. The dose and/or time intervals of two or more active agents are preferably selected such that the combined use of the components can result in a therapeutic effect on the disease or disorder which is greater than that achieved by the use of either component alone. The ingredients may each take a separate formulation form and such separate formulation forms may be the same or different.

The term "combination therapy" refers to the administration of two or more therapeutic agents or modalities (e.g., radiotherapy or surgery) to treat the diseases as described herein. Such administration includes co-administration of these therapeutic agents in a substantially simultaneous manner, for example, in a single capsule with a fixed proportion of active ingredients. Alternatively, such administration includes co-administration of the active ingredients in a variety of or separate containers (such as tablets, capsules, powder and liquid). The powder and/or liquid can be reconstituted or diluted to a desired dose before administration. In addition, such administration also includes using each type of the therapeutic agents at approximately the same time or in a sequential manner at different times. In any case, the therapeutic regimen will provide the beneficial effect of the pharmaceutical combination in the treatment of disorders or symptoms described herein.

As used herein, "treatment" (or "treat" or "treating") refers to slowing, interrupting, arresting, alleviating, stopping, lowering, or reversing the progression or severity of an existing symptom, disorder, condition, or disease.

As used herein, "prevention" (or "prevent" or "preventing") includes the inhibition of the development or progression of symptoms of a disease or disorder, or a specific disease or disorder. In some embodiments, subjects with family history of cancer are candidates for preventive regimens. Generally, in the context of cancer, the term "prevention" (or "prevent" or "preventing") refers to the administration of a drug prior to the onset of signs or symptoms of cancer, particularly in subjects at risk of cancer.

The term "vector" used herein refers to a nucleic acid molecule capable of proliferating another nucleic acid to which it is linked. The term includes vectors that serve as self-replicating nucleic acid structures as well as vectors binding to the genome of a host cell into which they have been introduced. Some vectors are capable of directing the expression of a nucleic acid to which they are operably linked. Such vectors are referred to as "expression vectors" herein.

"Subject/patient/individual sample" refers to a collection of cells or fluids obtained from a patient or a subject. The source of tissue or cell samples can be solid tissues, e.g., from fresh, frozen and/or preserved organ or tissue samples or biopsy samples or puncture samples; blood or any blood component; body fluids such as cerebrospinal fluids, amniotic fluids, peritoneal fluids, or interstitial fluids; and cells from a subject at any time during pregnancy or development. Tissue samples may comprise compounds which are naturally not mixed with tissues, such as preservatives, anticoagulants, buffers, fixatives, nutrients, and antibiotics.

II. IL-2 Mutant Protein Disclosed Herein

Advantageous Biological Properties of the IL-2 Mutant Protein Disclosed Herein The inventors have found through long-term research that the following molecular mutations and engineering, or combinations of one or more of the molecular mutations and engineering, can be performed as follows to simultaneously improve the efficacy of IL-2, reduce toxic side effects of IL-2, and achieve good productivity:

(i) introducing a certain residue mutation into the binding interface of IL-2 to the IL-2Rβγ receptor to weaken the binding to the IL-2Rβγ receptor and to down-regulate the activity of IL-2 to some extent. By including such mutations that weaken the binding to the IL-2Rβγ receptor, the IL-2 mutant protein disclosed herein can activate lymphocytes to kill tumors, while avoiding the release of a large amount of inflammatory factors, and thus drug-related toxicity, caused by over-activation of lymphocytes. In addition, by reducing the binding affinity of the IL-2 mutant protein disclosed herein for the IL-2 receptors extensively occurred on lymphocytes, the weakening mutations can also reduce the clearance of the IL-2 mutant protein mediated by the IL-2 receptors and prolong the period of action of the IL-2 mutant protein;

(ii) constructing the IL-2 mutant protein disclosed herein into an IL-2-Fc dimer. The formation of this dimer can increase the molecular weight of the IL-2 mutant protein disclosed herein, greatly reducing renal clearance and further extending the half-life of the IL2-Fc fusion protein by FcRn-mediated in vivo recycling. Thus, the high peak plasma concentration problem caused by the short half-life and high-frequency large-dose administration of IL-2 is overcome;

(iii) engineering the B'C' loop structure of IL-2, for example, by replacing with the loop of the IL-15 molecule or by truncating the B'C' loop of the IL-2 molecule. The B'C' loop mutation can significantly enhance the stability of the B'C' loop structure in the IL-2 mutant protein disclosed herein, and significantly improve the production performance of the IL-2 mutant protein and the IL-2-Fc dimeric molecule constructed thereof, e.g., significantly improving the expression yield and purity;

(iv) maintaining substantially comparable binding activity to IL-2Rα as the wild-type IL-2; or capable of combining the following mutations: (v) one or more specific mutations at the binding interface of IL-2 to the IL-2Rα receptor, to change the binding performance of the IL-2 mutant protein to IL-2Rα. Furthermore, the inventors have found that in the mutant protein disclosed herein, the binding activity of the IL-2 mutant protein to IL-2Rα can be regulated as needed, while the excellent properties described above are kept, to meet different drug-forming requirements of IL-2 in multiple aspects such as in anti-tumor therapy or in the treatment of autoimmune diseases, and thus to further impart excellent pharmacodynamic properties to the mutant protein disclosed herein.

Thus, through the engineering of the sequence, the IL2-Fc molecules disclosed herein, in one aspect, have weakened binding affinity for the IL2Rβ/γ receptor and achieve more excellent pharmacokinetic experimental results and pharmacodynamic results, and, in another aspect, have significantly improved druggability such as the protein expression yield and purity.

Thus, the present invention provides an IL-2 mutant protein with improved druggability and improved IL-2 receptor binding properties. IL-2-Fc molecules comprising the IL-2 mutant protein disclosed herein can effectively avoid excessive release of inflammatory factors caused by strong agonizing of lymphocytes, and has more stable and long-acting pharmacokinetic properties. Thus, a sufficiently high drug exposure can be achieved in the human body with a lower single dose, which avoids drug-related toxicity resulting from high $C_{max}$. Furthermore, it is more significant that, although the long-acting IL-2-Fc molecule of the present invention has weakened immunostimulatory activity for lymphocytes relative to native IL-2, the in vivo effective drug concentration of the molecule of the present invention is more lasting due to the significant improvements to the pharmacokinetic properties and it can achieve a long period of constant stimulation to lymphocytes, a comparable pharmacodynamic effect to or even a better pharmacodynamic effect than native IL-2 molecules, and better anti-tumor efficacy and tolerance in animals.

In addition, the mutant IL-2 protein having advantageous biological properties of the present invention can also be formed into an immunoconjugate with an antigen-binding molecule (e.g., an antibody or a fragment thereof) to enhance an immune or immunotherapeutic effect of the antigen-binding molecule while activating and expanding T cells or NK cells.

Improved Druggability

In some embodiments, the IL-2 mutant protein disclosed herein has improved druggability. For example, when expressed in mammalian cells such as HEK293 cells or CHO cells, particularly in the form of an Fc fusion protein, the IL-2 mutant protein has one or more properties selected from the following: (i) a superior expression yield to the wild-type IL-2 protein; and (ii) ease of purification to a higher purity of the protein.

In some embodiments disclosed herein, the IL-2 mutant protein disclosed herein shows an increased expression level relative to the wild-type IL-2. In some embodiments disclosed herein, the increased expression occurs in a mammalian cell expression system. The expression level can be determined by any suitable method that allows for quantitative or semi-quantitative analysis of the amount of recombinant IL-2 protein in cell culture supernatant, preferably the supernatant purified by one-step affinity chromatography. For example, the amount of recombinant IL-2 protein in a sample can be assessed by Western blotting or ELISA. In some embodiments, the expression yield of the IL-2 mutant protein disclosed herein in mammalian cells is increased by at least 1.1 times, or at least 1.5 times, or at least 2 times, 3 times or 4 times or more, or at least 5, 6, 7, 8 or 9 times, or even 10 times or more, e.g., about 10, 15, 20, 25, 30 or 35 times, compared to that of the wild-type IL-2.

In some embodiments, as shown by determining the purity of the protein purified by protein A affinity chromatography, the IL-2 mutant protein-Fc fusion disclosed herein has higher purity, relative to the wild-type IL-2 protein fusion. In some embodiments, the purity of the protein is detected by a SEC-HPLC technique. In some preferred embodiments, the IL-2 mutant protein-Fc fusion disclosed herein can have a purity of up to 70%, or 80%, or 90% or higher, preferably 92%, 93%, 94%, 95%, 98% or 99% or higher, after being purified by one-step protein A affinity chromatography.

In some embodiments, as shown by determining the purity of the protein purified by protein A affinity chromatography, the IL-2-Fc dimer protein disclosed herein has higher purity, relative to the corresponding IL-2-Fc dimer protein formed from the wild-type IL-2 protein. In some embodiments, the purity of the protein is detected by a SEC-HPLC technique. In some preferred embodiments, the IL-2-Fc dimer protein disclosed herein can have a purity of up to 70%, or 80%, or 90% or higher, preferably 92%, 93%, 94%, 95%, 98% or 99% or higher, after being purified by one-step protein A affinity chromatography.

Weakened Binding to IL-2βγ Receptor

By introducing a mutation into the binding interface to IL-2Rβγ, in some embodiments, the IL-2 mutant protein disclosed herein has weakened binding affinity for IL-2βγ relative to the corresponding protein before the introduction of the mutation.

In some embodiments, the IL-2 mutant protein disclosed herein has reduced binding affinity for the IL-2Rβ and/or IL-2Rβγ receptor relative to that before weakening by introducing an IL-2Rβγ binding interface mutation. In some embodiments, the IL-2 mutant protein disclosed herein has reduced binding affinity for the IL-2Rβ receptor relative to that before weakening; for example, the binding affinity is reduced by 1-20 times or more. In some embodiments, binding to the IL-2Rβ receptor is eliminated. In some embodiments, the IL-2 mutant protein disclosed herein has reduced binding affinity for the IL-2Rβγ receptor relative to that before weakening; for example, the binding affinity is reduced by 1-100 times or more. In some embodiments, the IL-2 mutant protein disclosed herein does not bind to the IL-2Rβ receptor, but is still capable of binding to the IL-2Rβγ receptor. Preferably, the binding to the IL-2Rβγ receptor is reduced by 1-100 times, e.g., about 20-80 times, compared to that before weakening. The binding affinity can be determined by measuring the equilibrium dissociation constant ($K_D$) of the binding of the IL-2 mutant protein disclosed herein, such as the IL-2 mutant protein disclosed herein fused to an Fc fragment or the dimeric molecule thereof, to the IL-2Rβ or IL-2Rβγ receptor using the SPR affinity assay technique.

By introducing mutations into the binding interface to IL-2Rβγ, in some embodiments, the IL-2 mutant protein disclosed herein, relative to the corresponding protein before the introduction of the mutations, has weakened IL-2 activity, e.g., at least one IL-2 activity selected from the following:

- reduced activation of T cells (e.g., $CD4^+$ and $CD8^+$ T cells, e.g., $CD4^+/CD8^+$ $CD25^-$T cells, or $CD4^+$ $CD25^+$ T cells), compared to that before weakening;
- reduced activation of NK cells, compared to that before weakening; and
- reduced IL-2-stimulated release of inflammatory factors from T cells/NK cells, compared to that before weakening.

In one embodiment, the IL-2 mutant protein disclosed herein leads to reduced IL-2-mediated activation and/or proliferation of lymphocytes (e.g., T cells and/or NK cells) relative to that before weakening. In one embodiment, the lymphocytes are $CD4^+$ and $CD8^+$ T cells, such as $CD25^-$ T cells. In one embodiment, in the STAT5 phosphorylation assay, the ability of the IL-2 mutant protein to activate $CD4^+$ and $CD8^+$ T cells is identified by measuring the activation of STAT5 phosphorylation signals by the IL-2 mutant protein in lymphocytes such as T cells or NK cells. For example, as described in the examples of the present application, STAT5 phosphorylation in cells can be analyzed by flow cytometry to determine the half maximum effective concentration ($EC_{50}$). For example, by measuring the ratio of $EC_{50}$ values of activation of STAT5 phosphorylation signals by the IL-2 weakened molecule disclosed herein and the corresponding protein, the IL-2 mutant molecule disclosed herein has "weakened" activation activity for T cells. According to the ratio, the activation activity of the IL-2 mutant molecule disclosed herein for T cells can be reduced by, e.g., 5 times or more, e.g., 10 times or more, or 50 times or more, or 100 times or more, or even 1000 times or more. For example, the activation activity of the IL-2 mutant molecule disclosed herein for T cells can be reduced by 10-50 times, or 50-100 times, or 100-1000 times, or more, relative to the corresponding protein. In some preferred embodiments, the IL-2 mutant protein disclosed herein has reduced cell surface IL-2 receptor-mediated clearance of IL-2 and an increased in vivo half-life, relative to the wild-type IL-2.

In some preferred embodiments, the IL-2 mutant protein disclosed herein has reduced in vivo toxicity mediated by IL-2 and its receptors relative to the wild-type IL-2.

Maintained or Altered (Preferably Weakened) Binding to IL-2Rα Receptor

The IL-2 protein triggers signaling and functions by interacting with IL-2 receptors. Wild-type IL-2 exhibits different affinities for different IL-2 receptors. IL-2β and IL-2γ receptors having a low affinity for wild-type IL-2 are expressed on resting effector cells, including $CD8^+$ T cells and NK cells. IL-2Rα receptors with a high affinity for wild-type IL-2 are expressed on regulatory T cell (Treg) cells and activated effector cells. Due to high affinity, the wild-type IL-2 will preferentially bind to IL-2Rα on the cell surface and then recruit IL-2Rβγ. Treg cells and activated effector cells are stimulated by downstream p-STAT5 signals released through the IL-2Rβγ. Without being bound by theory, altering the affinity of IL-2 for the IL-2Rα receptor will alter the preference of IL-2 for preferentially activating $CD25^+$ cells and the IL-2-mediated immune downregulation effect of Treg cells.

In some embodiments, the IL-2 mutant protein disclosed herein has a maintained or an altered ability to bind to the IL-2Rα receptor relative to the wild-type IL-2.

In some embodiments, the IL-2 mutant protein disclosed herein maintains binding to the IL-2Rα receptor relative to the wild-type IL-2. As used herein, the expression "maintain binding to the IL-2Rα receptor" means that the IL-2 mutant protein has a comparable binding activity to the IL-2Rα receptor relative to the wild-type IL-2 protein. Preferably, "comparable binding activity" means that when measured in the same manner, the binding activity values (e.g., binding affinity $K_D$) of the IL-2 mutant protein and the wild-type IL-2 protein are in a ratio between 1:20 and 20:1, preferably between 1:10 and 10:1. Preferably, the IL-2 mutant protein does not have an IL-2Rα binding interface mutation relative to the wild-type IL-2.

In some embodiments, the IL-2 mutant protein disclosed herein is a weakened IL-2 mutant molecule which maintains binding to the IL-2Rα receptor. In still other embodiments, the weakened IL-2 mutant protein disclosed herein does not have an IL-2Rα binding interface mutation relative to the wild-type IL-2. Preferably, the weakened IL-2 mutant molecule has improved selectivity for Treg and/or improved selectivity for NK cells (e.g., $CD3^-$ $CD56^+$ NK cells). In one embodiment, in the STAT5 phosphorylation assay, the selectivity of the IL-2 mutant protein for lymphocytes is identified by measuring the activation of STAT5 phosphorylation signals by the IL-2 mutant protein in different lymphocytes such as Treg cells, NK cells and $CD4^+$ and $CD8^+$ effector T cells. In one embodiment, in the STAT5 phosphorylation assay, the selectivity of the IL-2 mutant protein can be reflected by a dose window of the IL-2 mutant protein that selectively activates specific (one or more types of) lymphocytes without substantially activating other lymphocytes. For example, in some embodiments, the weakened IL-2 mutant protein disclosed herein may exhibit improved selectivity for Treg and/or improved selectivity for NK cells ($CD3^-$ $CD56^+$ NK cells) relative to that for effector T cells, such as $CD25^{-/low}$ $CD4^+$ and/or $CD8^+$ effector T lymphocytes. In still other embodiments, the improved selectivity may be reflected by low drug-related toxicity of the IL-2 mutant protein.

In other embodiments, the IL-2 mutant protein disclosed herein has a mutation introduced into the binding interface to IL-2Rα relative to the wild-type IL-2, the mutation causing the IL-2 mutant protein to have reduced or eliminated binding to the IL-2Rα receptor.

In still other embodiments, the IL-2 mutant protein disclosed herein reduces the preference of IL-2 for preferentially activating $CD25^+$ cells relative to the wild-type IL-2. In still other embodiments, the IL-2 mutant protein disclosed herein reduces IL-2-mediated immune downregulation effect of Treg cells relative to the wild-type IL-2.

In other embodiments, the IL-2 mutant protein disclosed herein has an immune downregulation effect. In still other embodiments, the IL-2 mutant protein disclosed herein can be used to treat autoimmune diseases.

Therefore, in some embodiments, the IL-2 mutant protein disclosed herein has one or more improved properties selected from the following:

- maintained or altered (e.g., reduced or increased, preferably reduced) binding affinity for an IL-2R receptor (IL-2Rαβγ, IL-2Rα and/or IL2Rαβγ), compared to the wild-type IL-2;
- maintained or altered (e.g., reduced or increased) activation of $CD25^+$ cells (e.g., $CD8^+$ T cells and Treg cells), compared to the wild-type IL-2;
- maintained or altered (e.g., eliminated or reduced, or increased) preference of IL-2 for preferentially activating $CD25^+$ cells (e.g., Treg cells), compared to the wild-type IL-2; and
- maintained or altered (e.g., reduced or increased) IL-2-induced downregulation effect of the immune response by Treg cells, compared to the wild-type IL-2.

In some embodiments, the binding affinity of the IL-2 mutant protein disclosed herein for the IL-2Rα receptor is reduced by at least 5 times, at least 10 times, or at least 25 times, particularly at least 30 times, 50 times or 100 times or more, relative to the wild-type IL-2 (e.g., $IL\text{-}2^{WT}$ set forth in SEQ ID NO: 1 or SEQ ID NO: 3). In a preferred embodiment, the mutant protein disclosed herein does not bind to the IL-2Rα receptor. The binding affinity can be determined by measuring the equilibrium dissociation constant ($K_D$) of the binding of the IL-2 mutant protein disclosed herein, such as the IL-2 mutant protein disclosed herein fused to an Fc fragment or the dimeric molecule thereof, to the IL-2Rα receptor using the SPR affinity assay technique.

In one embodiment, the IL-2 mutant protein disclosed herein reduces IL-2-mediated activation and/or proliferation of $CD25^+$ cells relative to the wild-type IL-2. In one embodiment, the $CD25^+$ cells are $CD25^+$ $CD8^+$ T cells. In another embodiment, the $CD25^+$ cells are Treg cells. In one embodiment, in the STAT5 phosphorylation assay, the ability of the IL-2 mutant protein to activate $CD25^+$ cells is identified by measuring the activation of STAT5 phosphorylation signals by the IL-2 mutant protein in $CD25^+$ cells. For example, as described in the examples of the present application, STAT5 phosphorylation in cells can be analyzed by flow cytometry to determine the half maximum effective concentration ($EC_{50}$). In one embodiment, the IL-2 mutant protein disclosed herein eliminates or reduces the preference of IL-2 for preferentially activating $CD25^+$ cells relative to the wild-type IL-2. In one embodiment, the $CD25^+$ cells are $CD25^+$ $CD8^+$ T cells. In another embodiment, the $CD25^+$ cells are Treg cells. In one embodiment, in the STAT5 phosphorylation assay, the ability of the IL-2 mutant protein to activate $CD25^-$ cells is identified by measuring the $EC_{50}$ values of the IL-2 mutant protein in activating STAT5 phosphorylation signals in $CD25^-$ cells and in $CD25^+$ cells respectively. For example, the activation preference of the IL-2 mutant protein for $CD25^+$ cells was determined by calculating the ratio of $EC_{50}$ values of the IL-2 mutant protein in activating STAT5 phosphorylation signals in $CD25^-$ and in $CD25^+$ T cells. Preferably, the preference of the mutant protein for $CD25^+$ cells is reduced by at least 10 times, preferably at least 100 times, 150 times, 200 times, or 300 times or more, relative to the wild-type protein.

In some embodiments, the IL-2 mutant protein disclosed herein has the properties of the mutant proteins shown in PCT/CN2021/081840, which is incorporated herein in its entirety.

Mutant Protein Disclosed Herein

In one aspect, the present invention provides an IL-2 mutant protein, which, compared to a wild-type IL-2 (preferably a human IL-2, and more preferably an IL-2 comprising the sequence of SEQ ID NO: 3), comprises mutations:

(i) a mutation that eliminates or reduces the binding affinity for an IL-2Rα receptor, at a binding interface of IL-2 to IL-2Rα, particularly at positions 35 and/or 42;

and/or (ii) a mutation that weakens/reduces the binding to an IL-2Rβγ receptor, at a binding interface of IL-2 to IL-2Rβγ, particularly at at least one position selected from positions 88, 127 and/or 130;

and (iii) a shortened B'C' loop region (i.e., a sequence linking amino acid residues aa72 and aa84), wherein preferably, the shortened loop region has less than 10, 9, 8, 7, 6 or 5 amino acids in length, and more preferably has 7 amino acids in length; preferably, the shortened B'C' loop region leads to an improved protein expression yield and/or purity;

and the amino acid positions are numbered according to SEQ ID NO: 3.

In one embodiment, the mutant protein comprises the mutations (i) and (iii), or comprises the mutations (ii) and (iii), or comprises the mutations (i), (ii) and (iiii).

IL-2Rβγ Binding Interface Mutation

An IL-2Rβγ binding interface mutation suitable for the mutant protein disclosed herein may be any mutation that can be combined with the other mutations of the present invention and leads to weakened or reduced binding affinity for IL-2Rβγ and/or weakened activation activity for lymphocytes (e.g., T cells/NK cells).

Examples of such mutations include, but are not limited to: mutations that leads to weakened or reduced binding to the IL-2Rβγ receptor, at the binding interface of IL-2 to IL-2Rβγ, particularly at at least one position selected from positions 88, 127 and 130.

In some embodiments, the IL-2Rβγ binding interface mutation includes one or more of the following mutations or a combination of the following mutations selected from:

N88D, N88R, S127E, S130R, N88R+S130R, and N88R+S127E.

In other embodiments, the IL-2 mutant protein disclosed herein comprising the IL-2Rβγ binding interface mutation of the present invention has weakened or reduced binding to IL-2Rβγ, e.g., weakened or reduced binding affinity for IL-2Rβγ as determined by an SPR affinity assay.

B'C' Loop Region Mutations

In one aspect, the IL-2 mutant protein disclosed herein, relative to the wild-type IL-2, comprises a B'C' loop region mutation; preferably, the mutation leads to a B'C' loop region with increased stability; more preferably, the mutation leads to improved druggability of the IL-2 mutant protein disclosed herein, e.g., an increased expression yield and/or purity.

In some embodiments, due to the mutation introduced, the mutant protein comprises a shortened B'C' loop region (i.e., a shortened linker sequence between the amino acid residues aa72 and aa84) compared to the wild-type IL-2 (preferably the human IL-2, and more preferably the IL-2 comprising the sequence of SEQ ID NO: 3).

Preferably, the shortened loop region has less than 10, 9, 8, 7, 6 or 5 amino acids in length, and more preferably has 7 amino acids in length, wherein the amino acid residues are numbered according to SEQ ID NO: 3.

Herein, B'C' loop region mutations suitable for the present invention include truncations and replacements of the B'C' loop region. In one embodiment, the mutations include truncations (e.g., a truncation of 1, 2, 3 or 4 amino acids in the B'C' loop region) or replacements of the amino acid residues aa73 to aa83 in the B'C' loop region, e.g., a truncation to form A(Q/G)SKN(F/I)H, preferably AQSKNFH, or a replacement with SGDASIH. In another embodiment, the mutations include truncations or replacements of the amino acid residues aa74 to aa83 in the B'C' loop region, e.g., a truncation to form (Q/G)SKN(F/I)H, or a replacement with GDASIH or AGDASIH.

In some embodiments, the IL-2 mutant protein disclosed herein comprises a B'C' loop chimeric mutation. The mutant protein, relative to the wild-type IL-2, comprises a substitution of the entirety or a part of the sequence linking aa72 to aa84, for example, with a short B'C' loop sequence from other four-helical short-chain cytokine family members. The short B'C' loop suitable for the substitution of the wild-type IL-2 can be identified from other four-helical short-chain cytokine IL family members, such as IL-15, IL-4, IL-21, or IL family members from non-human species such as mice, by the superpose of a crystal structure. In one embodiment, the sequence used for substitution is a B'C' loop sequence from interleukin IL-15, particularly human IL-15. In one embodiment, the substitution includes substitutions of the amino acid residues aa73 to aa83 in the B'C' loop region. In another embodiment, the substitution includes substitutions of the amino acid residues aa74 to aa83 in the B'C' loop region. Preferably, the IL-2 mutant protein disclosed herein, after the substitutions, has a B'C' loop sequence (i.e., a sequence linking aa72 to aa84) selected from the following: SGDASIH or AGDASIH, preferably AGDASIH.

In some embodiments, the IL-2 mutant protein disclosed herein comprises a B'C' loop truncation mutation. The mutant protein, relative to the wild-type IL-2, comprises a truncation of the sequence linking aa72 to aa84. In one embodiment, the truncation includes truncations of the amino acid residues aa73 to aa83 in the B'C' loop region. In another embodiment, the truncation includes truncations of the amino acid residues aa74 to aa83 in the B'C' loop region. For example, the sequence may be truncated by 1, 2, 3 or 4 amino acids at the C-terminus. Preferably, after the truncation, the IL-2 mutant protein disclosed herein has a B'C' loop region having a sequence of A(Q/G)SKN(F/I)H, preferably AQSKNFH. Preferably, after the truncation, the IL-2 mutant protein disclosed herein has a B'C' loop sequence (i.e., a sequence linking aa72 to aa84) selected from the following:

| Sequences of B'C' loop |
|---|
| AQSKNFH |
| AGSKNFH |
| AQSANFH |
| AQSANIH |

In one preferred embodiment, the IL-2 mutant protein disclosed herein comprises a B'C' loop region sequence (i.e., a sequence linking aa72 to aa84) selected from the following: AQSKNFH or AGDASIH.

IL-2Rα Binding Interface Mutation

In one aspect, the IL-2 mutant protein disclosed herein, relative to the wild-type IL-2, comprises one or more mutations at the binding interface to IL-2Rα, preferably at positions 35 and/or 42. Preferably, the mutation eliminates or reduces binding affinity for the IL-2Rα receptor.

In some preferred embodiments, the IL-2Rα binding interface mutation disclosed herein includes mutations K35E and/or F42A.

In other embodiments, the IL-2 mutant protein disclosed herein comprising the IL-2Rα binding interface mutation of the present invention has altered (preferably reduced or eliminated) binding to IL-2Rα, as determined, e.g., by an SPR affinity assay.

Other Mutations

In addition to the "IL-2Rβγ binding interface mutations", "B'C' loop region mutations" and "IL-2Rα binding interface mutations" described above, the IL-2 mutant protein disclosed herein can also have one or more mutations in other regions or positions, as long as it retains one or more beneficial properties described above. For example, the IL-2 mutant protein disclosed herein may further comprise a substitution at position 125, such as C125S, C125A, C125T, or C125V, so as to provide additional advantages, such as improved expression or homogeneity or stability (see, e.g., U.S. Pat. No. 4,518,584). For another example, the IL-2 mutant protein disclosed herein can further comprise a substitution at position 3, e.g., T3A, to remove the O-glycan modification at the N-terminus of IL2. Those skilled in the art know how to determine additional mutations that can be incorporated into the IL-2 mutant protein disclosed herein.

Preferred Exemplary Combinations of Mutations

In some preferred embodiments, the IL-2 mutant protein disclosed herein has weakened binding to IL-2Rβγ and has improved properties selected from one or both of: (i) reduced (or eliminated) binding to IL-2Rα; and (ii) improved expression level and purity. In some embodiments, the IL-2 mutant protein maintains binding to the IL-2Rα receptor relative to the wild-type IL-2.

In some embodiments, the present invention provides an IL-2 mutant protein, which comprises, relative to the wild-type IL-2:

(i) N88D;

N88R;

$$N88R+S130R;$$

$$F42A+N88R+S127E;\text{ or}$$

$$K35E+N88R+S127E;$$

and (ii) a B'C' loop region sequence AGDASIH or AQSKNFH;

and optionally (iii) T3A.

In some embodiments, the present invention provides an IL-2 mutant protein, which comprises, relative to the wild-type IL-2:

(i) N88D;

N88R;

$$N88R+S130R;$$

$$F42A+N88R+S127E;\text{ or}$$

$$K35E+N88R+S127E;$$

and (ii) a B'C' loop region sequence AGDASIH orAQSKNFH;

and (iii) T3A.

In some embodiments, the IL-2 mutant protein disclosed herein (i) comprises or consists of an amino acid sequence having at least 90%, 91%, 92%, 93%, 94%, 95%, 96%, 97%, 98%, or 99% identity to an amino acid sequence set forth in SEQ ID NO: 4; or (ii) comprises or consists of an amino acid sequence set forth in SEQ ID NO: 4; or (iii) comprises or consists of an amino acid sequence having one or more (preferably no more than 10, and more preferably no more than 5, 4, 3, 2 or 1) amino acid changes compared to an amino acid sequence set forth in SEQ ID NO: 4, wherein preferably, the mutant protein comprises an N88D substitution and a B'C' loop region sequence AGDASIH, and optionally T3A.

In some embodiments, the IL-2 mutant protein disclosed herein (i) comprises or consists of an amino acid sequence having at least 90%, 91%, 92%, 93%, 94%, 95%, 96%, 97%, 98%, or 99% identity to an amino acid sequence set forth in SEQ ID NO: 23; or (ii) comprises or consists of an amino acid sequence set forth in SEQ ID NO: 23; or (iii) comprises or consists of an amino acid sequence having one or more (preferably no more than 10, and more preferably no more than 5, 4, 3, 2 or 1) amino acid changes compared to an amino acid sequence set forth in SEQ ID NO: 23, wherein preferably, the mutant protein comprises an N88R substitution and a B'C' loop region sequence AGDASIH, and optionally T3A.

In some embodiments, the IL-2 mutant protein disclosed herein (i) comprises or consists of an amino acid sequence having at least 90%, 91%, 92%, 93%, 94%, 95%, 96%, 97%, 98%, or 99% identity to an amino acid sequence set forth in SEQ ID NO: 25; or (ii) comprises or consists of an amino acid sequence set forth in SEQ ID NO: 25; or (iii) comprises or consists of an amino acid sequence having one or more (preferably no more than 10, and more preferably no more than 5, 4, 3, 2 or 1) amino acid changes compared to an amino acid sequence set forth in SEQ ID NO: 25, wherein preferably, the mutant protein comprises N88R+S130R substitutions and a B'C' loop region sequence AGDASIH, and optionally T3A.

In some embodiments, the IL-2 mutant protein disclosed herein (i) comprises or consists of an amino acid sequence having at least 90%, 91%, 92%, 93%, 94%, 95%, 96%, 97%, 98%, or 99% identity to an amino acid sequence set forth in SEQ ID NO: 27; or (ii) comprises or consists of an amino acid sequence set forth in SEQ ID NO: 27; or (iii) comprises or consists of an amino acid sequence having one or more (preferably no more than 10, and more preferably no more than 5, 4, 3, 2 or 1) amino acid changes compared to an amino acid sequence set forth in SEQ ID NO: 27, wherein preferably, the mutant protein comprises F42A+N88R+S127E substitutions and a B'C' loop region sequence AQSKNFH, and optionally T3A.

In some embodiments, the IL-2 mutant protein disclosed herein (i) comprises or consists of an amino acid sequence having at least 90%, 91%, 92%, 93%, 94%, 95%, 96%, 97%, 98%, or 99% identity to an amino acid sequence set forth in SEQ ID NO: 29; or (ii) comprises or consists of an amino acid sequence set forth in SEQ ID NO: 29; or (iii) comprises or consists of an amino acid sequence having one or more (preferably no more than 10, and more preferably no more than 5, 4, 3, 2 or 1) amino acid changes compared to an amino acid sequence set forth in SEQ ID NO: 29, wherein preferably, the mutant protein comprises F42A+N88R+S127E substitutions and a B'C' loop region sequence AGDASIH, and optionally T3A.

In some embodiments, the IL-2 mutant protein disclosed herein (i) comprises or consists of an amino acid sequence having at least 90%, 91%, 92%, 93%, 94%, 95%, 96%, 97%, 98%, or 99% identity to an amino acid sequence set forth in SEQ ID NO: 31; or (ii) comprises or consists of an amino acid sequence set forth in SEQ ID NO: 31; or (iii) comprises or consists of an amino acid sequence having one or more (preferably no more than 10, and more preferably no more than 5, 4, 3, 2 or 1) amino acid changes compared to an amino acid sequence set forth in SEQ ID NO: 31, wherein preferably, the mutant protein comprises K35E+N88R+S127E substitutions and a B'C' loop region sequence AQSKNFH, and optionally T3A.

For mutations and combinatorial mutations suitable for the present invention, see also the applicant's co-pending application PCT/CN2021/081840, which is incorporated herein by reference in its entirety. The sequence difference between the IL-2 mutant protein and the wild-type protein can be expressed in terms of sequence identity or in terms of the difference in the number of amino acids between the two. In one embodiment, the IL-2 mutant protein has at least 85%, 86%, 87%, 88%, or 89% identity, preferably more than 90% (preferably 95%) but preferably no more than 97% and more preferably no more than 96% identity to the wild-type protein. In another embodiment, in addition to the mutations described above in the present invention, the IL-2 mutant protein may also have no more than 15, e.g., 1-10, or 1-5, e.g., 0, 1, 2, 3 or 4, mutations relative to the wild-type protein. In one embodiment, the other mutations may be conservative substitutions.

III. Fusion Protein and IL-2-Fc Dimer Protein

In one aspect, the present invention also provides a fusion protein comprising the IL-2 mutant protein disclosed herein. In one preferred embodiment, the IL-2 mutant protein disclosed herein is fused to another polypeptide, such as albumin, and preferably an antibody Fc fragment, which can provide improved pharmacokinetic properties.

In one embodiment, the present invention provides an IL-2 mutant protein fusion protein, which comprises the IL-2 mutant protein disclosed herein fused to an antibody Fc fragment.

The Fc fragment for use in the present invention may comprise a mutation that reduces or eliminates effector functions. In one preferred embodiment, the Fc fragment has reduced Fc-mediated effector functions, e.g., reduced or eliminated ADCC and/or ADCP and/or CDC effector functions. For example, in some particular embodiments, the Fc fragment for use in the present invention has mutations L234A/L235A or L234A/L235E/G237A that reduce binding to the Fcγ receptor.

In yet another preferred embodiment, the Fc fragment may have a mutation that leads to an increased serum half-life, e.g., a mutation that improves binding of the Fc fragment to FcRn.

In some embodiments, the Fc fragment fused to the IL-2 mutant protein is a human IgG Fc, e.g., human IgG1 Fc, human IgG2 Fc or human IgG4 Fc. In one embodiment, the Fc fragment comprises or consists of an amino acid sequence set forth in SEQ ID NO: 6, 12, 42 or 43, or an amino acid sequence having at least 90% identity, e.g., 95%, 96%, 97%, 99% or more identity thereto.

In some embodiments, the IL-2 mutant protein is fused, either directly or via a linker, to the Fc. In some embodiments, the linker may be selected to enhance the activation of the Fc fusion protein on $CD25^-$ T cells. In one embodiment, the linker is $(GGGGS)_n$ or GSGS, preferably $(GGGGS)_2$.

In a further aspect, the present invention also provides a dimeric molecule comprising the IL-2 mutant protein disclosed herein fused to an Fc fragment. With such a dimeric molecule, the molecular weight can be increased to 60-80 KDa, and the renal clearance is greatly reduced. In addition, the half-life of the IL2-Fc fusion protein can be further extended by FcRn-mediated in vivo recycling.

In some embodiments, the present invention provides an IL-2-Fc dimer protein, which is a homodimer, wherein a first monomer and a second monomer comprise, from N-terminus to C-terminus, i) an IL-2 mutant protein; ii) a linker; and iii) an Fc fragment.

In other embodiments, the present invention provides an IL-2-Fc dimer protein, which is a heterodimer and comprises:

a) a first monomer, comprising, from N-terminus to C-terminus, i) the IL-2 mutant protein; ii) the linker; and iii) a first Fc fragment; and b) a second monomer, comprising a second Fc fragment.

In some embodiments, the first Fc fragment and the second Fc fragment comprise a first heterodimerization mutation and a second heterodimerization mutation that promote the formation of the heterodimer from the first monomer and the second monomer, respectively. In some preferred embodiments, the first and second heterodimerization mutations comprise a combination of Knob:Hole mutations, such as the combination of mutations T366W/S354C: Y349C/T366S/L368A/Y407V.

In some preferred embodiments, the first heterodimerization mutation in the first Fc fragment includes a Knob mutation and the second heterodimerization mutation in the second Fc fragment includes a Hole mutation; alternatively, the first heterodimerization mutation in the first Fc fragment includes a Hole mutation and the second heterodimerization mutation in the second Fc fragment includes a Knob mutation.

As understood by those skilled in the art, Fc fragments suitable for the fusion protein and the dimeric molecule disclosed herein may be any antibody Fc fragment. In one embodiment, the Fc fragment of the present invention is effector function-silenced.

In one embodiment, the Fc fragment is modified in one or more properties selected from: the effector function of the Fc region and the complement activation function of the Fc region. In one embodiment, the effector function or complement activation function has been reduced or eliminated relative to a wild-type Fc region of the same isotype. In one embodiment, the effector function is reduced or eliminated by using a method selected from: reducing glycosylation of the Fc region, using an Fc isotype that naturally has a reduced or an eliminated effector function, and Fc region modification.

In one embodiment, the effector function is reduced or eliminated by reducing glycosylation of the Fc region. In one embodiment, the glycosylation of the Fc region is reduced by using a method selected from: producing the fusion protein or the dimeric molecule disclosed herein in an environment that does not allow wild-type glycosylation; removing carbohydrate groups already present in the Fc region; and modifying the Fc region so that wild-type glycosylation does not occur. In one embodiment, the glycosylation of the Fc region is reduced by using the method of modifying the Fc region so that wild-type glycosylation does not occur, e.g., including a mutation at position 297 in the Fc region so that the wild-type asparagine residue at that position is replaced with another amino acid that interferes with glycosylation at that position, e.g., an N297A mutation.

In one embodiment, the effector function is reduced or eliminated by at least one Fc region modification. In one embodiment, the at least one Fc region modification is selected from: an Fc region point mutation that impairs binding to one or more Fc receptors, selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438 and 439; an Fc region point mutation that impairs binding to C1q, selected from the following positions: 270, 322, 329 and 321; and an Fc region point mutation at position 132 of a CH1 domain. In one embodiment, the effector function is reduced or eliminated by point mutations L234A & L235A (i.e., LALA mutations) of the Fc region. In one embodiment, the modification is an Fc region point mutation that impairs binding to C1q selected from the following positions: 270, 322, 329 and 321. In another embodiment, the modification is the elimination of some Fc regions.

As understood by those skilled in the art, to facilitate the formation of the heterodimer of the present invention, the Fc fragment of the dimeric molecule disclosed herein may comprise mutations that favor the dimerization of the first monomer and the second monomer. Preferably, corresponding Knob and Hole mutations are introduced into the first and second monomers based on the Knob-in-Hole technique.

Thus, in one embodiment, the dimeric molecule disclosed herein comprises:

i) a homodimeric Fc-region of the human IgG1 subtype, optionally with mutations P329G, L234A and L235A, or mutations L234A and L235A, or
ii) a homodimeric Fc-region of the human IgG4 subtype, optionally with mutations P329G, S228P, and L235E, or
iii) a heterodimeric Fc-region, wherein
a) one Fc-region polypeptide comprises a mutation T366W, and the other Fc-region polypeptide comprises mutations T366S, L368A and Y407V, or
b) one Fc-region polypeptide comprises mutations T366W and Y349C, and the other Fc-region polypeptide comprises mutations T366S, L368A, Y407V and S354C, or
c) one Fc-region polypeptide comprises mutations T366W and S354C, and the other Fc-region polypeptide comprises mutations T366S, L368A, Y407V and Y349C, or
iv) a heterodimeric Fc-region of the human IgG4 subtype, wherein both Fc-region polypeptides comprise mutations P329G, L234A and L235A, and
a) one Fc-region polypeptide comprises a mutation T366W, and the other Fc-region polypeptide comprises mutations T366S, L368A and Y407V, or
b) one Fc-region polypeptide comprises mutations T366W and Y349C, and the other Fc-region polypeptide comprises mutations T366S, L368A, Y407V and S354C, or
c) one Fc-region polypeptide comprises mutations T366W and S354C, and the other Fc-region polypeptide comprises mutations T366S, L368A, Y407V and Y349C, or
v) a heterodimeric Fc-region of the human IgG4 subtype, wherein the two Fc-region polypeptides both comprise mutations P329G, S228P and L235E, and
a) one Fc-region polypeptide comprises a mutation T366W, and the other Fc-region polypeptide comprises mutations T366S, L368A and Y407V, or
b) one Fc-region polypeptide comprises mutations T366W and Y349C, and the other Fc-region polypeptide comprises mutations T366S, L368A, Y407V and S354C, or
c) one Fc-region polypeptide comprises mutations T366W and S354C, and the other Fc-region polypeptide comprises mutations T366S, L368A, Y407V and Y349C.

In some embodiments, the Fc region further comprises additional mutations that favor the purification of the heterodimer. For example, an H435R mutation (Eric J. Smith, *Scientific Reports*|5:17943|DOI: 10.1038/srep17943) can be introduced into one of the Fc regions of the heterodimer (e.g., an Fc region with Hole mutations) to facilitate the purification of the heterodimer using protein A. In other embodiments, for heterodimeric monomers comprising a hinge region, mutations such as C220S may also be introduced into the hinge region to facilitate the formation of the heterodimer.

The Fc region suitable for use in the fusion protein of the present invention may also be used in the Fc portion of the immunoconjugate of the present invention.

In some embodiments, the IL-2 mutant protein fused to the Fc region (i) comprises or consists of an amino acid sequence having at least 90%, 91%, 92%, 93%, 94%, 95%, 96%, 97%, 98%, or 99% identity to an amino acid sequence set forth in SEQ ID NO: 7, 24, 26, 28, 30 or 32; or
(ii) comprises or consists of an amino acid sequence set forth in SEQ ID NO: 7, 24, 26, 28, 30 or 32; or
(iii) comprises or consists of an amino acid sequence having one or more (preferably no more than 10, and more preferably no more than 5, 4, 3, 2 or 1) amino acid changes compared to an amino acid sequence set forth in SEQ ID NO: 7, 24, 26, 28, 30 or 32, wherein the IL-2 mutant protein comprises the mutation described herein.

In some embodiments, the IL-2 mutant protein fused to the Fc of the present invention (i) comprises or consists of an amino acid sequence having at least 90%, 91%, 92%, 93%, 94%, 95%, 96%, 97%, 98%, or 99% identity to an amino acid sequence set forth in SEQ ID NO: 7; or
(ii) comprises or consists of an amino acid sequence set forth in SEQ ID NO: 7; or
(iii) comprises or consists of an amino acid sequence having one or more (preferably no more than 10, and more preferably no more than 5, 4, 3, 2 or 1) amino acid changes compared to an amino acid sequence set forth in SEQ ID NO: 7, wherein preferably, the mutant protein comprises an N88D substitution and a B'C' loop region sequence AGDASIH, and optionally T3A.

In some embodiments, the IL-2 mutant protein fused to the Fc of the present invention (i) comprises or consists of an amino acid sequence having at least 90%, 91%, 92%, 93%, 94%, 95%, 96%, 97%, 98%, or 99% identity to an amino acid sequence set forth in SEQ ID NO: 24; or
(ii) comprises or consists of an amino acid sequence set forth in SEQ ID NO: 24; or
(iii) comprises or consists of an amino acid sequence having one or more (preferably no more than 10, and more preferably no more than 5, 4, 3, 2 or 1) amino acid changes compared to an amino acid sequence set forth in SEQ ID NO: 24, wherein preferably, the mutant protein comprises an N88R substitution and a B'C' loop region sequence AGDASIH, and optionally T3A.

In some embodiments, the IL-2 mutant protein fused to the Fc of the present invention (i) comprises or consists of an amino acid sequence having at least 90%, 91%, 92%, 93%, 94%, 95%, 96%, 97%, 98%, or 99% identity to an amino acid sequence set forth in SEQ ID NO: 26; or
(ii) comprises or consists of an amino acid sequence set forth in SEQ ID NO: 26; or
(iii) comprises or consists of an amino acid sequence having one or more (preferably no more than 10, and more preferably no more than 5, 4, 3, 2 or 1) amino acid changes compared to an amino acid sequence set forth in SEQ ID NO: 26, wherein preferably, the mutant protein comprises N88R+S130R substitutions and a B'C' loop region sequence AGDASIH, and optionally T3A.

In some embodiments, the IL-2 mutant protein fused to the Fc of the present invention (i) comprises or consists of an amino acid sequence having at least 90%, 91%, 92%, 93%, 94%, 95%, 96%, 97%, 98%, or 99% identity to an amino acid sequence set forth in SEQ ID NO: 28; or
(ii) comprises or consists of an amino acid sequence set forth in SEQ ID NO: 28; or
(iii) comprises or consists of an amino acid sequence having one or more (preferably no more than 10, and more preferably no more than 5, 4, 3, 2 or 1) amino acid changes compared to an amino acid sequence set forth in SEQ ID NO: 28, wherein preferably, the mutant protein comprises F42A+N88R+S127E substitutions and a B'C' loop region sequence AQSKNFH, and optionally T3A.

In some embodiments, the IL-2 mutant protein fused to the Fc of the present invention (i) comprises or consists of an amino acid sequence having at least 90%, 91%, 92%, 93%, 94%, 95%, 96%, 97%, 98%, or 99% identity to an amino acid sequence set forth in SEQ ID NO: 30; or
(ii) comprises or consists of an amino acid sequence set forth in SEQ ID NO: 30; or
(iii) comprises or consists of an amino acid sequence having one or more (preferably no more than 10, and more preferably no more than 5, 4, 3, 2 or 1) amino acid changes compared to an amino acid sequence set forth in SEQ ID NO: 30, wherein preferably, the mutant protein comprises F42A+N88R+S127E substitutions and a B'C' loop region sequence AGDASIH, and optionally T3A.

In some embodiments, the IL-2 mutant protein fused to the Fc of the present invention (i) comprises or consists of an amino acid sequence having at least 90%, 91%, 92%, 93%, 94%, 95%, 96%, 97%, 98%, or 99% identity to an amino acid sequence set forth in SEQ ID NO: 32; or
(ii) comprises or consists of an amino acid sequence set forth in SEQ ID NO: 32; or
(iii) comprises or consists of an amino acid sequence having one or more (preferably no more than 10, and more preferably no more than 5, 4, 3, 2 or 1) amino acid changes compared to an amino acid sequence set forth in SEQ ID NO: 32, wherein preferably, the mutant protein comprises K35E+N88R+S127E substitutions and a B'C' loop region sequence AQSKNFH, and optionally T3A.

As will be appreciated by those skilled in the art, linkers suitable for linking the IL-2 mutant protein and the Fc fragment in the fusion protein and dimeric molecule disclosed herein may be any linker known in the art. In some embodiments, the linker may comprise an IgG1 hinge, or may comprise a linker sequence selected from the following: (GS)n, (GSGGS)n, (GGGGS)n and (GGGS)n, wherein n is an integer of at least 1. Preferably, the linker includes $(G4S)_2$, i.e., GGGGSGGGGS (SEQ ID NO: 5).

IV. Immunoconjugates

The present invention further provides an immunoconjugate comprising the IL2 mutant protein or the IL-2 mutant protein fusion protein (e.g., a fusion protein fused to an Fc fragment) of the present invention and an antigen-binding molecule. Preferably, the antigen-binding molecule is an immunoglobulin molecule, particularly an IgG molecule, an antibody, or an antibody fragment, and more particularly a Fab molecule, an scFv molecule or a half antibody (comprising or consisting of one heavy chain and one light chain).

In some embodiments, the antigen-binding molecule specifically binds to an antigen present on a tumor cell or in the tumor environment, particularly and preferably PD-1, PD-L1 and/or PD-L2. Thus, the immunoconjugate of the present invention can target the tumor cell or the tumor environment after being administrated to a subject, thereby providing further therapeutic benefits, such as the feasibility of treatment at lower doses and the consequent low side effects, and enhanced immunotherapeutic effects or anti-tumor effects, etc.

In the immunoconjugate disclosed herein, the IL-2 mutant protein disclosed herein can be linked, either directly or via a linker, to another molecule or antigen-binding molecule, and in some embodiments, a proteolytic cleavage site is provided therebetween. In the immunoconjugate of the present invention, the IL-2 mutant protein or the fusion protein thereof of the present invention may also be linked to another molecule or antigen-binding molecule by dimerization.

In some embodiments, the antibody is an antibody directed against a tumor-associated antigen, e.g., PD-1, PD-L1, or PD-L2.

The antibody suitable for linking to the IL-2 mutant protein may be an intact antibody or an antigen-binding fragment thereof. In some embodiments, the antibody of the present invention is an antibody in the form of IgG1, IgG2, IgG3, or IgG4, preferably an antibody in the form of IgG1. In some embodiments, the antibody of the present invention is a monoclonal antibody. In some embodiments, the antibody of the present invention is humanized. In some embodiments, the antibody of the present invention is a human antibody. In some embodiments, the antibody of the present invention is a chimeric antibody. In one embodiment, the antigen-binding fragment of the antibody of the present invention is selected from the following antibody fragments: Fab, Fab', Fab'-SH, Fv, a single-chain antibody (e.g., scFv), $(Fab')_2$, a single-domain antibody (e.g., VHH), a domain antibody (dAb), a linear antibody or a half antibody.

In one embodiment of the present invention, the immunoconjugate of the present invention comprises an IL-2 mutant protein or a fusion protein thereof and an anti-PD-1 antibody or an antigen-binding fragment thereof.

In one embodiment of the present invention, the immunoconjugate of the present invention comprises: a first monomer comprising an IL-2 mutant protein fused to an Fc fragment; and a second monomer comprising an antibody or a fragment thereof that specifically binds to PD-1, preferably a fragment comprising one heavy chain and one light chain of the anti-PD-1 antibody.

In some embodiments, the Fc fragment in the first monomer comprises a Knob mutation, and the antibody heavy chain in the second monomer comprises a hole mutation, or vice versa. In some embodiments, the Knob mutation is a Knob: S354C & T366W, and/or the Hole mutation is Y349C & T366S & L368A & Y407V.

In one specific embodiment, the IL-2 mutant protein fusion protein of the present invention has a form of Format 1 as shown in FIG. 1A.

In one embodiment of the present invention, the antibody or the antigen-binding fragment thereof directed against PD-1 is an anti-PD-1 antibody or an antigen-binding fragment thereof disclosed in WO2017024465A1. In one embodiment, the anti-PD-1 antibody or the antigen-binding fragment thereof comprises one or more CDRs (preferably 3 CDRs, i.e., HCDR1, HCDR2H, and HCDR3, or LCDR1, LCDR2, and LCDR3; and more preferably 6 CDRs, i.e., HCDR1, HCDR2, HCDR3, LCDR1, LCDR2, and LCDR3) of the anti-PD-1 antibody or the antigen-binding fragment thereof disclosed in WO2017024465A1, or comprises a VH and/or a VL of the anti-PD-1 antibody or the antigen-binding fragment thereof disclosed in WO2017024465A1, or comprises a heavy chain and/or a light chain of the antibody.

In some embodiments, the anti-PD-1 antibody or the antigen-binding fragment thereof comprises 3 complementarity determining regions from a heavy chain variable region (HCDRs): HCDR1, HCDR2, and HCDR3. In some embodiments, the anti-PD-1 antibody or the antigen-binding fragment thereof comprises 3 complementarity determining regions from a light chain variable region (LCDRs): LCDR1, LCDR2, and LCDR3. In some embodiments, the anti-PD-1 antibody or the antigen-binding fragment thereof comprises 3 complementarity determining regions from a heavy chain variable region (HCDRs) and 3 complementarity determining regions from a light chain variable region (LCDRs).

In some aspects, the anti-PD-1 antibody or the antigen-binding fragment thereof comprises a heavy chain variable region (VH). In some aspects, the anti-PD-1 antibody or the antigen-binding fragment thereof comprises a light chain variable region (VH). In some aspects, the anti-PD-1 antibody or the antigen-binding fragment thereof comprises a heavy chain variable region (VH) and a light chain variable region (VL). In some embodiments, the heavy chain variable region comprises 3 complementarity determining regions (CDRs) from the heavy chain variable region: HCDR1, HCDR2 and HCDR3. In some embodiments, the light chain variable region comprises 3 complementarity determining regions (CDRs) from the light chain variable region: LCDR1, LCDR2 and LCDR3.

In some embodiments, the anti-PD-1 antibody or the antigen-binding fragment thereof comprises an antibody heavy chain. In some embodiments, the anti-PD-1 antibody heavy chain comprises a heavy chain variable region and a heavy chain constant region. In some embodiments, the anti-PD-1 antibody or the antigen-binding fragment thereof of the present invention comprises an antibody light chain. In some embodiments, the anti-PD-1 antibody light chain of the present invention comprises a light chain variable region and a light chain constant region. In some embodiments, the anti-PD-1 antibody or the antigen-binding fragment thereof of the present invention further comprises a heavy chain and a light chain.

In some embodiments, the heavy chain variable region (VH)

(i) comprises or consists of an amino acid sequence having at least 90%, 91%, 92%, 93%, 94%, 95%, 96%, 97%, 98%, or 99% identity to an amino acid sequence set forth in SEQ ID NO: 8; or (ii) comprises or consists of an amino acid sequence set forth in SEQ ID NO: 8; or (iii) comprises or consists of an amino acid sequence having one or more (preferably no more than 10, and more preferably no more than 5, 4, 3, 2, or 1) amino acid changes (preferably amino acid replacements, and more preferably conservative amino acid replacements) compared to an amino acid sequence set forth in SEQ ID NO: 8, wherein preferably, the amino acid changes do not occur in the CDRs.

In some embodiments, the light chain variable region (VL)

(i) comprises or consists of an amino acid sequence having at least 90%, 91%, 92%, 93%, 94%, 95%, 96%, 97%, 98%, or 99% identity to an amino acid sequence set forth in SEQ ID NO: 15; or (ii) comprises or consists of an amino acid sequence set forth in SEQ ID NO: 15; or (iii) comprises or consists of an amino acid sequence having one or more (preferably no more than 10, and more preferably no more than 5, 4, 3, 2, or 1) amino acid changes (preferably amino acid replacements, and more preferably conservative amino acid replacements) compared to an amino acid sequence set forth in SEQ ID NO: 15, wherein preferably, the amino acid changes do not occur in the CDRs.

In some embodiments, the 3 complementarity determining regions from the heavy chain variable region (HCDRs), HCDR1, HCDR2 and HCDR3, are selected from (i) three complementarity determining regions HCDR1, HCDR2, and HCDR3 comprised in a VH set forth in SEQ ID NO: 8, or (ii) relative to the sequence in (i), a sequence comprising a total of at least one and no more than 5, 4, 3, 2, or 1 amino acid change (preferably amino acid replacement, and more preferably conservative replacement) in the three HCDRs.

In some embodiments, the 3 complementarity determining regions from the light chain variable region (LCDRs), LCDR1, LCDR2, and LCDR3, are selected from (i) three complementarity determining regions LCDR1, LCDR2, and LCDR3 comprised in a VL set forth in SEQ ID NO: 15, or (ii) relative to the sequence in (i), a sequence comprising a total of at least one and no more than 5, 4, 3, 2, or 1 amino acid change (preferably amino acid replacement, and more preferably conservative replacement) in the three LCDRs.

In some embodiments, the HCDR1 comprises or consists of an amino acid sequence set forth in SEQ ID NO: 9, or the HCDR1 comprises an amino acid sequence having one, two, or three changes (preferably amino acid replacements, and more preferably conservative replacements) compared to the amino acid sequence set forth in SEQ ID NO: 9.

In some embodiments, the HCDR2 comprises or consists of an amino acid sequence set forth in SEQ ID NO: 10, or the HCDR2 comprises an amino acid sequence having one, two, or three changes (preferably amino acid replacements, and more preferably conservative replacements) compared to the amino acid sequence set forth in SEQ ID NO: 10.

In some embodiments, the HCDR3 comprises or consists of an amino acid sequence set forth in SEQ ID NO: 11, or the HCDR3 comprises an amino acid sequence having one, two, or three changes (preferably amino acid replacements, and more preferably conservative replacements) compared to the amino acid sequence set forth in SEQ ID NO: 11.

In some embodiments, the LCDR1 comprises or consists of an amino acid sequence set forth in SEQ ID NO: 16, or the LCDR1 comprises an amino acid sequence having one, two, or three changes (preferably amino acid replacements, and more preferably conservative replacements) compared to the amino acid sequence set forth in SEQ ID NO: 16.

In some embodiments, the LCDR2 comprises or consists of an amino acid sequence set forth in SEQ ID NO: 17, or the LCDR2 comprises an amino acid sequence having one, two, or three changes (preferably amino acid replacements, and more preferably conservative replacements) compared to the amino acid sequence set forth in SEQ ID NO: 17.

In some embodiments, the LCDR3 comprises or consists of an amino acid sequence set forth in SEQ ID NO: 18, or the LCDR3 comprises an amino acid sequence having one, two, or three changes (preferably amino acid replacements, and more preferably conservative replacements) compared to the amino acid sequence set forth in SEQ ID NO: 18.

In some embodiments, the heavy chain constant region (HC) of the anti-PD-1 antibody or the antigen-binding fragment thereof is a heavy chain constant region of IgG1, IgG2, IgG3, or IgG4, preferably a heavy chain constant region of IgG1, e.g., a heavy chain constant region of IgG1 with L234A & L235A (LALA) mutations. In some embodiments, a knob-into-hole mutation is introduced into the heavy chain constant region. For example, mutations S354C and T366W are introduced to obtain an antibody heavy chain comprising a knob mutation, and/or mutations Y349C & T366S & L368A & Y407V are introduced to obtain an antibody heavy chain comprising a hole mutation. In some embodiments, the light chain constant region of the anti-PD-1 antibody or the antigen-binding fragment thereof is a lambda or Kappa light chain constant region.

In some embodiments, the heavy chain constant region of the antibody or the antigen-binding fragment thereof (i) comprises or consists of an amino acid sequence having at least 85%, 90%, 91%, 92%, 93%, 94%, 95%, 96%, 97%, 98% or 99% identity to an amino acid sequence selected from SEQ ID NO: 21;

(ii) comprises or consists of an amino acid sequence selected from SEQ ID NO: 21; or (iii) comprises or consists of an amino acid sequence having one or more (preferably no more than 20 or 10, and more preferably no more than 5, 4, 3, 2, or 1) amino acid changes (preferably amino acid replacements, and more preferably conservative amino acid replacements) compared to an amino acid sequence selected from SEQ ID NO: 21.

In some embodiments, the heavy chain constant region of the antibody or the antigen-binding fragment thereof comprising a hole mutation (i) comprises or consists of an amino acid sequence having at least 85%, 90%, 91%, 92%, 93%, 94%, 95%, 96%, 97%, 98% or 99% identity to an amino acid sequence selected from SEQ ID NO: 13;

(ii) comprises or consists of an amino acid sequence selected from SEQ ID NO: 13; or (iii) comprises or consists of an amino acid sequence having one or more (preferably no more than 20 or 10, and more preferably no more than 5, 4, 3, 2, or 1) amino acid changes (preferably amino acid replacements, and more preferably conservative amino acid replacements) compared to an amino acid sequence selected from SEQ ID NO: 13.

In some embodiments, the heavy chain of the antibody or the antigen-binding fragment thereof comprising a hole mutation (i) comprises or consists of an amino acid sequence having at least 85%, 90%, 91%, 92%, 93%, 94%, 95%, 96%, 97%, 98% or 99% identity to an amino acid sequence selected from SEQ ID NO: 14;

(ii) comprises or consists of an amino acid sequence selected from SEQ ID NO: 14; or (iii) comprises or consists of an amino acid sequence having one or more (preferably no more than 20 or 10, and more preferably no more than 5, 4, 3, 2, or 1) amino acid changes (preferably amino acid replacements, and more preferably conservative amino acid replacements) compared to an amino acid sequence selected from SEQ ID NO: 14.

In some embodiments, the heavy chain of the antibody or the antigen-binding fragment thereof (i) comprises or consists of an amino acid sequence having at least 85%, 90%, 91%, 92%, 93%, 94%, 95%, 96%, 97%, 98% or 99% identity to an amino acid sequence selected from SEQ ID NO: 22;

(ii) comprises or consists of an amino acid sequence selected from SEQ ID NO: 22; or (iii) comprises or consists of an amino acid sequence having one or more (preferably no more than 20 or 10, and more preferably no more than 5, 4, 3, 2, or 1) amino acid changes (preferably amino acid replacements, and more preferably conservative amino acid replacements) compared to an amino acid sequence selected from SEQ ID NO: 22.

In some embodiments, the light chain constant region of the antibody or the antigen-binding fragment thereof (i) comprises or consists of an amino acid sequence having at least 85%, 90%, 91%, 92%, 93%, 94%, 95%, 96%, 97%, 98% or 99% identity to an amino acid sequence selected from SEQ ID NO: 19;

(ii) comprises or consists of an amino acid sequence selected from SEQ ID NO: 19; or (iii) comprises or consists of an amino acid sequence having one or more (preferably no more than 20 or 10, and more preferably no more than 5, 4, 3, 2, or 1) amino acid changes (preferably amino acid replacements, and more preferably conservative amino acid replacements) compared to an amino acid sequence selected from SEQ ID NO: 19.

In some embodiments, the light chain of the antibody or the antigen-binding fragment thereof (i) comprises or consists of an amino acid sequence having at least 85%, 90%, 91%, 92%, 93%, 94%, 95%, 96%, 97%, 98% or 99% identity to an amino acid sequence selected from SEQ ID NO: 20;

(ii) comprises or consists of an amino acid sequence selected from SEQ ID NO: 20; or (iii) comprises or consists of an amino acid sequence having one or more (preferably no more than 20 or 10, and more preferably no more than 5, 4, 3, 2, or 1) amino acid changes (preferably amino acid replacements, and more preferably conservative amino acid replacements) compared to an amino acid sequence selected from SEQ ID NO: 20.

In some specific embodiments of the present invention, the anti-PD-1 antibody or the antigen-binding fragment thereof comprises:

three complementarity determining regions HCDR1, HCDR2, and HCDR3 comprised in a VH set forth in SEQ ID NO: 8, and three complementarity determining regions LCDR1, LCDR2, and LCDR3 comprised in a VL set forth in SEQ ID NO: 15.

In some specific embodiments of the present invention, the anti-PD-1 antibody or the antigen-binding fragment thereof comprises:

HCDR1, HCDR2, and HCDR3 set forth in amino acid sequences of SEQ ID NOs: 9, 10, and 11, respectively, and LCDR1, LCDR2, and LCDR3 set forth in amino acid sequences of SEQ ID NOs: 16, 17, and 18, respectively.

In some specific embodiments of the present invention, the anti-PD-1 antibody or the antigen-binding fragment thereof comprises:

a VH comprising or consisting of an amino acid sequence set forth in SEQ ID NO: 8 or an amino acid sequence having at least 90%, 91%, 92%, 93%, 94%, 95%, 96%, 97%, 98% or 99% identity thereto, and a VL comprising or consisting of an amino acid sequence set forth in SEQ ID NO: 15 or an amino acid sequence having at least 90%, 91%, 92%, 93%, 94%, 95%, 96%, 97%, 98% or 99% identity thereto.

In some specific embodiments of the present invention, the anti-PD-1 antibody or the antigen-binding fragment thereof comprises:

a heavy chain comprising or consisting of an amino acid sequence set forth in SEQ ID NO: 14 or 22 or an amino acid sequence having at least 85%, 90%, 91%, 92%, 93%, 94%, 95%, 96%, 97%, 98% or 99% identity thereto; and a light chain comprising or consisting of an amino acid sequence set forth in SEQ ID NO: 20 or an amino acid sequence having at least 85%, 90%, 91%, 92%, 93%, 94%, 95%, 96%, 97%, 98% or 99% identity thereto.

In some preferred embodiments, the anti-PD-1 antibody fragment in the immunoconjugate comprises or consists of one heavy chain and one light chain.

In some specific embodiments of the present invention, the anti-PD-1 antibody fragment comprises:

a heavy chain with a hole mutation comprising or consisting of an amino acid sequence set forth in SEQ ID NO: 14 or an amino acid sequence having at least 85%, 90%, 91%, 92%, 93%, 94%, 95%, 96%, 97%, 98%, or 99% identity thereto; and a light chain comprising or consisting of an amino acid sequence set forth in SEQ ID NO: 20 or an amino acid sequence having at least 85%, 90%, 91%, 92%, 93%, 94%, 95%, 96%, 97%, 98%, or 99% identity thereto.

The immunoconjugate of the present invention, preferably compared to the anti-PD-1 antibody, to the IL-2 mutant protein or the fusion protein thereof to Fc, and/or to the known immunoconjugates comprising the anti-PD-1 antibody and the IL-2 mutant protein, has one or more or all of the following properties:

(1) reduced or eliminated binding affinity for IL-2Rα, particularly as compared to the wild-type IL-2 or the fusion protein thereof, (2) reduced binding affinity for IL-2Rβγ, particularly as compared to the IL-2 mutant protein or the fusion protein thereof to Fc, and/or to the known immunoconjugates comprising the anti-PD-1 antibody and the IL-2 mutant protein;

(3) capable of selectively activating cells expressing PD-1, i.e., having high selectivity for PD-1;

(4) lower activity in T cells not expressing PD-1 (e.g., $CD8^+$ or $CD4^+$ T cells) and higher activity in T cells expressing PD-1 (e.g., $CD8^+$ or $CD4^+$ T cells), indicating high selectivity for PD-1, particularly as compared to the known immunoconjugates comprising the anti-PD-1 antibody and the IL-2 mutant protein;

(5) weaker IL-2 activity in cells expressing (e.g., overexpressing) an IL-2 receptor, particularly as compared to the known immunoconjugates comprising the anti-PD-1 antibody and the IL-2 mutant protein;

(6) stronger IL-2 activity in cells expressing an IL-2 receptor and PD-1 than as compared to cells expressing the IL-2 receptor but not expressing PD-1, indicating selectivity for PD-1 positive cells; and (7) a stronger anti-tumor effect and/or lower toxicity (e.g., without or with a lower effect on the body weight of the treated subject), preferably as compared to the anti-PD-1 antibody, to the IL-2 mutant protein or the fusion protein thereof to Fc, to a combination of the anti-PD-1 antibody with the IL-2 mutant protein or the fusion protein thereof, and/or to the known immunoconjugates comprising the anti-PD-1 antibody and the IL-2 mutant protein.

V. Polynucleotide, Vector and Host

The present invention provides a nucleic acid encoding any of the strands or any of the monomers or domains in any of the IL-2 mutant proteins or fusion proteins or dimeric molecules or conjugates above. The polynucleotide sequence encoding the mutant protein disclosed herein can be generated by de novo solid phase DNA synthesis or by PCR mutagenesis of an existing sequence encoding the wild-type IL-2 using methods well known in the art. In addition, the polynucleotide and the nucleic acid disclosed herein may comprise a segment encoding a secretion signal peptide and are operably linked to a segment encoding the mutant protein disclosed herein so that secretory expression of the mutant protein disclosed herein can be directed.

The present invention also provides a vector comprising the nucleic acid disclosed herein. In one embodiment, the vector is an expression vector, e.g., a eukaryotic expression vector. The vector includes, but is not limited to, a virus, a plasmid, a cosmid, a a phage, or a yeast artificial chromosome (YAC). In a preferred embodiment, the expression vector disclosed herein is a pYDO_017 expression vector.

In addition, the present invention also provides a host cell comprising the nucleic acid or the vector. Host cells suitable for replicating and supporting the expression of the IL-2 mutant protein, the fusion, the dimer or the immunoconjugate are well known in the art. Such cells can be transfected or transduced with a particular expression vector, and a large number of cells comprising vectors can be cultivated for inoculation in large-scale fermenters, so as to obtain sufficient IL-2 mutants, fusions, dimers or immunoconjugates for clinical application. In one embodiment, the host cell is eukaryotic. In another embodiment, the host cell is selected from a yeast cell and a mammalian cell (e.g., a CHO cell or a 293 cell). Examples of available mammalian host cell lines include SV40 transformed monkey kidney CV1 lines (COS-7), human embryonic kidney lines (293 or 293T cells, as described, for example, in Graham et al., *J Gen Virol* 36,59 (1977)), baby hamster kidney cells (BHK), mouse Sertoli cells (TM4 cells, as described, for example, in Mather, *Biol Reprod* 23,243-251 (1980)), monkey kidney cells (CV1), African green monkey kidney cells (VERO-76), human cervical cancer cells (HELA), canine kidney cells (MDCK), buffalo rat liver cells (BRL3A), human lung cells (W138), human liver cells (HepG2), mouse mammary tumor cells (MMT060562), TRI cells (as described, for example, in Mather et al., *Annals N.Y. Acad Sci* 383,44-68 (1982)), MRC5 cells, and FS4 cells. Other available mammalian host cell lines include Chinese hamster ovary (CHO) cells, including dhfr-CHO cells (Urlaub et al., *Proc Natl Acad Sci USA* 77,4216 (1980)), and myeloma cell lines such as Y0, NS0, P3X63, and Sp2/0. In one embodiment, the host cell is a eukaryotic cell, preferably a mammalian cell such as a Chinese hamster ovary (CHO) cell, a human embryonic kidney (HEK) cell, or a lymphocyte (e.g., Y0, NS0, and Sp20 cells).

VI. Preparation Method

In a further aspect, the present invention provides a method for preparing the IL-2 mutant protein, the fusion, the dimer or the conjugate disclosed herein, wherein the method comprises culturing a host cell comprising a nucleic acid encoding the protein, the fusion, the dimer or the conjugate under conditions suitable for expression of the IL-2 mutant protein, the fusion, the dimer or the conjugate, as provided above, and optionally isolating the protein, the fusion, the dimer or the conjugate from the host cell (or the host cell culture medium).

In one embodiment, a vector comprising a nucleic acid encoding an IL-2 mutant protein is transferred into cells and expressed, and then the cells (or the cell culture supernatant) are collected. The IL-2 mutant protein is extracted and purified to obtain the IL-2 mutant protein. In one specific embodiment, the purification method is an affinity purification method. In another specific embodiment, the purification method is ion exchange purification.

In one embodiment, a vector comprising a nucleic acid encoding an IL-2 mutant protein fused to Fc is transferred into cells and expressed, and then the cells (or the cell culture supernatant) are collected. The IL-2 mutant protein fused to Fc is extracted and purified to obtain the IL-2 mutant protein fused to Fc. In one specific embodiment, the purification method is an affinity purification method. In another specific embodiment, the purification method is ion exchange purification.

In one embodiment, a vector comprising a nucleic acid encoding an IL-2 mutant protein fused to Fc, a nucleic acid encoding a heavy chain of a PD-1 antibody, and a nucleic acid encoding a light chain of a PD-1 antibody is transferred into cells, expressed and assembled into an immunoconjugate, and then the cells (or the cell culture supernatant) were collected. The immunoconjugate was extracted and purified to obtain the immunoconjugate. In one specific embodiment, the purification method is an affinity purification method. In another specific embodiment, the purification method is ion exchange purification.

VII. Assays

The IL-2 mutant protein provided herein can be identified, screened, or characterized for its physical/chemical properties and/or biological activities through a variety of assays known in the art. In one aspect, the IL-2 mutant protein disclosed herein can be tested for its binding activity to an IL-2 receptor. For example, the binding to a human IL-2Rα or β protein, IL-2Rβγ or IL-2Rαβγ can be determined by methods known in the art, such as ELISA and Western blotting, or by the exemplary methods disclosed in the examples herein. For example, the flow cytometry can be used, wherein cells such as yeast display cells that are transfected to express the mutant protein on the cell surface react with a labeled (e.g., biotin-labeled) IL-2Rα or β protein, IL-2Rβγ or IL-2Rαβγ complex. Alternatively, the binding of the mutant protein to the receptor, including the binding kinetics (e.g., the $K_D$ value), can be determined by an SPR assay in IL-2-Fc fusion or dimeric molecule form.

In a further aspect, the ability of the IL-2 mutant protein to bind to the IL-2 receptor can be measured indirectly by measuring the signaling and/or immune activation at the downstream of receptor binding. Thus, in some embodiments, an assay for identifying the IL-2 mutant protein having a biological activity is provided. The biological activities may include, for example, the ability to induce proliferation of T cells and/or NK cells and/or Treg cells with IL-2 receptors, the ability to induce IL-2 signaling in T cells and/or NK cells and/or Treg cells with IL-2 receptors, reduced ability to induce apoptosis in T cells, the ability to induce tumor regression and/or to improve survival, and reduced in vivo toxicity properties, such as reduced vascular permeability. The present invention also provides an IL-2 mutant protein having such biological activities in vivo and/or in vitro, an Fc fusion thereof and a dimeric molecule comprising same.

Various methods known in the art can be used for determining the biological activities of the IL-2. For example, an assay suitable for testing the ability of the IL-2 mutant protein disclosed herein (e.g., in dimeric molecule form) to stimulate IFN-γ production by NK cells may comprise the steps of: incubating the cultured NK cells with the IL-2 mutant protein disclosed herein, and measuring the IFN-γ concentration in the culture medium by ELISA. IL-2 signaling induces several signaling pathways and involves JAK (Janus kinase) and STAT (signal transducers and activators of transcription) signaling molecules.

The interaction of the IL-2 with the β and γ subunits of the receptor results in phosphorylation of the receptor and JAK1 and JAK3 (which bind to the β and γ subunits, respectively). STAT5 then binds to the phosphorylated receptor and is phosphorylated on a very important tyrosine residue. This results in dissociation of STAT5 from the receptor, dimerization of STAT5, and translocation of STAT5 dimers to the nucleus where they facilitate the transcription of target genes. Thus, the ability of the mutant IL-2 polypeptide to induce signaling via the IL-2 receptor can be assessed, for example, by measuring the phosphorylation of STAT5. Details of this method have been disclosed in the examples. For example, PBMCs can be treated with the mutant IL-2 polypeptide, the fusion, the dimer or the immunoconjugate disclosed herein, and the level of phosphorylated STAT5 is determined by flow cytometry.

In the case of the immunoconjugate of the present invention with an antibody directed against an antigen, the activity or level of IL-2 described above can be determined in cells expressing the antigen. Furthermore, the effect of mutated IL-2 or a fusion, a dimer or an immunoconjugate thereof on tumor growth and survival can be assessed in a variety of animal tumor models known in the art. For example, heterografts of cancer cell lines can be implanted into immunodeficient mice and treated with the mutant IL-2 polypeptide, the fusion, the dimer or the immunoconjugate disclosed herein. The in vivo anti-tumor effects of the mutant IL-2 polypeptide, the fusion, the dimeric molecule and the immunoconjugate disclosed herein can be determined based on tumor growth inhibition (e.g., calculated relative to an isotype control antibody). In addition, the in vivo toxicity of the mutant IL-2 polypeptide, the fusion, the dimeric molecule and the immunoconjugate disclosed herein can be determined based on changes in the body weight of animals (e.g., changes in the absolute body weight or percent changes in the body weight relative to the body weight before administration). The in vivo toxicity can also be determined based on mortality, life-time observations (visible symptoms of adverse effects, e.g., behavior, body weight, and body temperature), and clinical and anatomical pathology (e.g., measurement of blood chemistry values and/or histopathological analysis).

In a further aspect, the druggability (e.g., expression yield and product purity) of the mutant protein disclosed herein can be characterized by using methods known in the art. For the determination of the expression yield, when the mutant protein is secreted from the cultured cells and expressed in the culture supernatant, the cell culture fluid collected by centrifugation can be assayed for the protein content. Alternatively, the assay may be performed after one-step purification of the collected cell culture fluid, for example, after one-step affinity chromatography purification. For the determination of the purity of the product, the purity can be determined after one-step affinity chromatography purification of the collected culture supernatant of the production cells to determine the purification performance of the mutant protein. Preferably, the mutant protein disclosed herein, after being purified by this one-step affinity chromatography, has significantly higher purity than the wild-type protein, indicating that the mutant protein disclosed herein has a better purification performance. The purity determination method can be any conventional method known in the art, including but not limited to, the SEC-HPLC method.

In a further aspect, the pharmacokinetic properties, e.g., half-life, of the mutant IL-2 polypeptide, the fusion, the dimeric molecule or the immunoconjugate disclosed herein can be characterized by using methods known in the art.

VIII. Pharmaceutical Composition and Pharmaceutical Formulation

The present invention further comprises a composition (including a pharmaceutical composition or a pharmaceutical formulation) comprising the mutant IL-2 polypeptide, the fusion, the dimer or the immunoconjugate, and a composition comprising the polynucleotide encoding the mutant IL-2 polypeptide, the fusion, the dimer or the immunoconjugate. Such compositions can further optionally comprise suitable pharmaceutical supplementary materials, such as a pharmaceutical carrier and a pharmaceutical excipient known in the art, including buffers.

The pharmaceutical composition comprising the mutant IL-2 polypeptide, the fusion, the dimer or the immunoconjugate disclosed herein may be prepared by conventional mixing, dissolving, emulsifying, encapsulating, entrapping or lyophilizing processes. The pharmaceutical composition may be formulated in a conventional manner using one or more physiologically acceptable carriers, diluents, excipients or auxiliaries which facilitate processing of the proteins into formulations that can be used pharmaceutically. Suitable formulations depend on the route of administration selected.

The immunoconjugate may be formulated into a composition in a free acid or base, neutral or salt form. Pharmaceutically acceptable salts are salts that substantially retain the biological activity of the free acid or base. These salts include acid addition salts, e.g., those formed with free amino groups of the protein composition, or with inorganic acids such as hydrochloric acid or phosphoric acid, or with organic acids such as acetic acid, oxalic acid, tartaric acid or mandelic acid. Salts formed with free carboxyl groups can also be derived from inorganic bases such as sodium hydroxide, potassium hydroxide, ammonium hydroxide, calcium hydroxide or ferric hydroxide; or derived from organic bases such as isopropylamine, trimethylamine, histidine or procaine. Pharmaceutically acceptable salts tend to be more soluble in aqueous solvents and other protic solvents than the corresponding free base forms.

IX. Combination Product

In one aspect, the present invention further provides a combination product comprising the mutant IL-2 polypeptide, the fusion, the dimer or the immunoconjugate disclosed herein, and one or more other therapeutic agents (e.g., a chemotherapeutic agent, other antibodies, a cytotoxic agent, a vaccine, an anti-infective active agent, and the like). The combination product of the present invention can be used in the treatment method of the present invention.

In some embodiments, the combination product is used for preventing or treating cancer.

X. Therapeutic Method and Use

In one aspect, the present invention relates to a method for preventing or treating a disease, such as cancer, in a subject, wherein the method comprises administering to the subject an effective amount of any of the mutant IL-2 polypeptides, the fusions, the dimers or the immunoconjugates described herein. The cancer may be at an early, intermediate, or advanced stage, or may be a metastatic cancer. In some embodiments, the cancer may be a solid tumor or a hematological tumor. In some embodiments, the cancer is a gastrointestinal tumor or melanoma, such as colon cancer or colorectal cancer. In some embodiments, the tumor is a tumor or cancer that is resistant to a known drug such as a known anti-PD-1 antibody, e.g., a refractory tumor or cancer.

In some embodiments, the cancer is a cancer characterized by elevated protein levels and/or nucleic acid levels (e.g., elevated expression) of PD-1, PD-L1 and/or PD-L2. In some embodiments, the mutant IL-2 polypeptide, the fusion, the dimer or the immunoconjugate disclosed herein can be used to stimulate the immune system of a host, e.g., to enhance the immune response of cells. "Stimulating the immune system" according to any of the embodiments described above may include any one or more of an overall increase in immune functions, an increase in T cell functions, an increase in B cell functions, a restoration of lymphocyte functions, an increase in IL-2 receptor expression, an increase in T cell responsiveness, an increase in natural killer cell activity or lymphokine-activated killer (LAK) cell activity, and the like.

The mutant IL-2 polypeptide, the fusion, the dimer or the immunoconjugate disclosed herein (and the pharmaceutical composition comprising same, and optionally an additional therapeutic agent) can be administered by any suitable method, including parenteral administration, intrapulmonary administration, intranasal administration, and, if required by locoregional treatment, intralesional administration. Parenteral infusion includes intramuscular, intravenous, intra-arterial, intraperitoneal, or subcutaneous administration. The administration may be performed by any suitable route, such as injection, e.g., intravenous or subcutaneous injection, to some extent depending on short-term or long-term administration. Various administration schedules are encompassed herein, including, but not limited to, single administration or multiple administrations at multiple time points, bolus injection, and pulse infusion.

In order to prevent or treat a disease, the appropriate dosage of the mutant IL-2 polypeptide, the fusion, the dimer or the immunoconjugate disclosed herein (used alone or in combination with one or more additional therapeutic agents) will depend on the type of the disease to be treated, the type of the antibody, severity and progression of the disease, the purpose for which the antibody is administered (prevention or treatment), previous treatments, clinical history of a patient, responses to the antibody, and the discretion of an attending physician. The antibody is suitably administered to a patient through a single treatment or through a series of treatments. In some embodiments, the mutant IL-2 polypeptide, the fusion protein, the dimer or the immunoconjugate disclosed herein can be administered to a patient at higher doses without toxicity.

In a further aspect, the present invention further provides use of the mutant IL-2 polypeptide, the fusion, the dimer or the immunoconjugate disclosed herein in the manufacture of a medicament for use in the aforementioned methods (e.g., for treatment).

The following examples are described to assist in understanding the present invention. The examples are not intended to be and should not be interpreted in any way as limiting the protection scope of the present invention.

These and other aspects and embodiments of the present invention are illustrated in the drawings (brief description of the drawings follows) and in the following detailed description of the present invention and are described in the following examples. Any or all of the features described above and throughout the present invention may be combined in various embodiments of the present invention. The following examples further illustrate the present invention. However, it should be understood that the examples are described by way of illustration rather than limitation, and various modifications may be made by those skilled in the art.

Example 1. Design of Immunoconjugates of Anti-hPD-1 and IL-2 Mutant

The present invention designs an immunoconjugate molecule (aPD-1/IL-2m immunoconjugate) that can specifically bind to human PD-1 to block the binding of PD-1 to PD-L1 so as to relieve an immune brake mechanism and can also specifically bind to an IL-2 receptor on a T cell or an NK cell so as to activate and amplify the T cell or the NK cell, wherein the immunoconjugate molecule comprises an anti-PD-1 antibody and an IL-2 mutant, and is capable of enhancing an immunotherapeutic effect of the PD-1 antibody.

Figure 2:
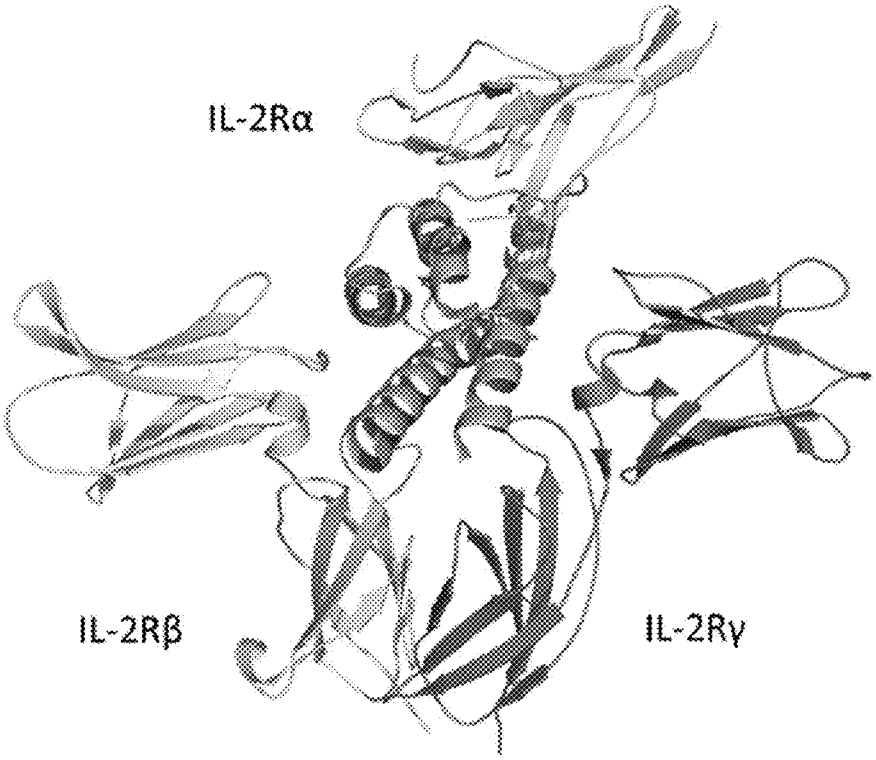
FIG. 2 shows the crystal structure of IL-2 binding to a receptor (PDB: 2ERJ).

The molecular form of the immunoconjugate molecule of the present invention is shown in FIG. 1A, and the immunoconjugate comprises two parts: 1) a second monomer, derived from an antibody binding to PD-1, wherein the sequence of the antibody binding to PD-1 is derived from WO2017024465A1; and 2) a first monomer, i.e., an IL-2 mutant (IL-2 mutant protein or IL-2m) engineered as follows: according to a crystal structure 2ERJ of a complex of IL-2 and a receptor (FIG. 2), selecting a mutation site at a binding interface of the receptor to reduce the binding of IL-2 to the receptor; and optimizing a B'C' loop region sequence (A73-R83, a wild type set forth in SEQ ID NO: 40) of IL-2 to improve the druggability of IL-2, wherein the optimization of the loop region is the replacement of the B'C' loop region of IL-2 with a human IL-15 B'C' loop region (AGDASIH, SEQ ID NO: 39), orthe deletion ofthe last 4 amino acids of the IL-2 B'C' loop region to obtain a truncated IL-2 B'C' loop region (AQSKNFH, SEQ ID NO: 41).

Sequence information about a control molecule, an IL-2-Fc fusion protein and IL-2 mutant-anti-PD-1 antibody immunoconjugates used in the examples is shown in the sequence listing, and IL-2 mutation information is shown in the table below.

TABLE 1

IL-2 mutant-anti-PD-1 antibody immunoconjugates and control molecules

| Molecule | Mutation site | B'C' loop region |
|---|---|---|
| 2061 | A control molecule in this study, derived from US20180326010A1 and designed to eliminate or reduce the affinity of a mutant IL-2 polypeptide for an IL-2Rα subunit | WT |
| 3010 | C125S | WT |
| 2063 | T3A + N88D | Replacement with IL15 B'C' loop region |
| 2132 | T3A + N88R | Replacement with IL15 B'C' loop region |
| 2149 | T3A + N88R + S130R | Replacement with IL15 B'C' loop region |
| 2213 | T3A + F42A + N88R + S127E | Truncation of IL-2 B'C' loop region |
| 2214 | T3A + F42A + N88R + S127E | Replacement with IL15 B'C' loop region |
| 2219 | T3A + K35E + N88R + S127E | Truncation of IL-2 B'C' loop region |

Example 2. Preparation of IL-2 Receptors and Immunoconjugates

Expression and Purification of IL-2 Receptors

Vector Construction

An avi tag (GLNDIFEAQKIEWHE, the tag peptide can be biotinylated under BirA enzyme catalysis) and 6 histidine tags (HHHHHH) were linked to the C-terminus of the sequence of an IL-2 receptor IL-2Rα (UniProt: P01589, aa22-217), which was constructed into a pTT5 vector (Addgene), transfected into HEK293 cells for expression, and subjected to affinity purification using a nickel column (Histrap excel, GE, 17-3712-06) to obtain IL-2 Rα.

The IL-2Rβγ complex was an Fc heterodimer based on Knobs in holes. The sequence of IL-2Rβ was constructed into the N-terminus of Fc-Knob (SEQ ID NO: 37), and the sequence of IL-2Rγ was constructed into the N-terminus of Fc-Hole (SEQ ID NO: 38). They were constructed separately into pcDNA3.1 vectors, then co-transfected into the cells and expressed. The vector containing IL-2Rβ and the vector containing IL-2Rγ were co-transferred into HEK293 cells and expressed using a transient transfection method. First, the plasmid DNA and the transfection reagent PEI (Polysciences, 23966) were prepared in a superclean bench.

3 mL of Opti-MEM medium (Gibco, Catalog No. 31985-070) was added to a 50-mL centrifuge tube, followed by the addition of 30 μg of the corresponding plasmid DNA. The Opti-MEM medium containing the plasmid was filtered with a 0.22 μm filter, 90 μg of PEI (1 g/L) was then added, and the mixture was left to stand for 20 min. The DNA/PEI mixture was gently poured into 27 mL of HEK293 cells, mixed well, and cultured at 37° C. with 8% $CO_2$ for another 6 days. The cell supernatant was obtained and purified to obtain the IL-2Rβγ complex. Nickel column affinity purification: the nickel column (5 mL Histrap excel, GE, 17-3712-06) used for purification was soaked with 0.1 M NaOH for 2 h, and then washed with 5- to 10-fold column volume of ultra-pure water to remove alkali liquor. The purification column was equilibrated with 5-fold column volume of binding buffer (20 mM Tris pH7.4, 300 mM NaCl) prior to purification. The cell supernatant was passed through the equilibrated column and then 10-fold column volume of wash buffer (20 mM Tris 7.4, 300 mM NaCl, 10 mM imidazole) was passed through the column to remove non-specific binding heteroproteins. The target protein was then eluted with 3-5-fold column volume of eluent (20 mM Tris 7.4, 300 mM NaCl, 100 mM imidazole). The collected protein was buffer-exchanged into PBS (Gibco, 70011-044) by ultrafiltration concentration, and further separated and purified using superdex200 increase (GE, 10/300GL, 10245605). The elution peak of the monomer was collected, and the equilibration buffer and elution buffer for the column were PBS.

Mabselect affinity purification: cells were centrifuged at 13000 rpm for 20 min, and the supernatant was collected and purified by pre-packed column Hitrap Mabselect Sure. The procedures were as follows: the packing column was equilibrated with 5-fold column volume of equilibration buffer (0.2 M Tris, 0.15 M NaCl, pH 7.2) before purification; the collected supernatant was passed through the column, and then the column was washed with 10-fold column volume of equilibration buffer to remove non-specific binding proteins; the packing was washed with 5-fold column volume of elution buffer (0.1 M sodium citrate, pH 3.5), and the eluate was collected; 80 μL of Tris (2 M Tris) was added per 1 mL of eluate, the mixture was buffer-exchanged into PBS buffer using an ultrafiltration concentration tube, and then the concentration and purity were determined.

Ion exchange purification: heterodimer molecules in bispecific molecules were separated by ion exchange chromatography, and homodimer impurities were removed.

Preparation of Immunoconjugates

A heavy chain Hole and a light chain of the anti-PD-1 antibody were constructed separately into pcDNA3.1 vectors, and an IL-2 protein was linked to the N-terminus of IgG1 Fc Knob via a linker and constructed into pcDNA3.1 vectors. The above three plasmids and 3-fold mass of PEI (for example, 1 μg ofheavy chain Hole+1 μg of light chain+1 μg of IL-2m-linker-Fc-Knob+9 μg of PEI were needed for the transfection of 3 mL of HEK293 cells) were co-transfected into HEK293 cells, and each immunoconjugate molecule used in this example was expressed and prepared.

The preparation of cells and collection and purification of samples were the same as the preparation method for receptors described above.

Example 3. Affinity Assay of IL-2 for Receptors

The equilibrium dissociation constant ($K_D$) for the binding of immunoconjugates of the present invention to a human IL-2 receptor (IL2Rα or IL-2Rβγ) was determined using surface plasmon resonance (SPR). Based on the principle of SPR, when a beam of polarized light entered the end face of a prism at a certain angle, surface plasma waves were generated at the interface between the prism and a gold film, causing free electrons in a metal film to generate resonance, namely surface plasmon resonance. When in analysis, a layer of protein was fixed on the surface of a sensing chip, and then a sample to be detected flowed on the surface of the chip. If there were molecules capable of interacting with the protein on the surface of the chip in the sample, the refractive index of the gold film surface was changed, finally causing changes in the SPR angle. The information such as the affinity and the kinetic constant of an analyte could be obtained by detecting the SPR angle changes.

In this example, the $K_D$ of the immunoconjugates for the IL-2 receptors was determined by Biacore T200 (Cytiva). The specific procedures were as follows: IL2Rα and IL2Rβγ proteins containing biotin tags were separately captured to the chip surface to which SA (streptavidin) was coupled, and then the binding and dissociation between the proteins on the chip surface and the studied immunoconjugates and control molecule in the mobile phase were detected to obtain affinity and kinetic constants.

The method comprises chip preparation and affinity detection. The assay procedure used 10×HBS-EP+ (BR-1006-69, Cytiva) diluted 10 times as an experimental buffer. During the chip preparation, SA was coupled on the surface of a CM5 chip (29-1496-03, Cytiva) using an amino coupling kit (BR-1006-33, Cytiva), and the remaining activation sites were blocked by injection of 1 M ethanolamine after coupling. Each cycle for the affinity assay included capture of the receptor, binding of one concentration of the molecule to be studied, and chip regeneration. The molecules after gradient dilution (the molecular concentration gradient was 0-400 nM) flowed over the chip surface in an order from low to high concentrations at a flow rate of 30 μL/min, with the binding time of 180 s and the dissociation time of 300 s. Finally, the chip was regenerated using 5 mM NaOH (BR-1003-58, Cytiva). Data results were analyzed using Biacore T200 analysis software (version No. 3.1) and using an analysis 1:1 binding or homeostasis analysis model.

The affinity of the immunoconjugates to be studied or control molecule for human PD1 (Catalog No. PD1-H5221, ACRO Biosystem) was determined using Biacore T200 (Cytiva, T200). The specific procedures were as follows: the molecules to be studied were captured to the chip surface to which Protein A was coupled (29127555, Cytiva), and then the binding and dissociation between the molecules on the chip surface and the antigens in the mobile phase were detected to obtain affinity and kinetic constants. The assay procedure used 10×HBS-EP+(BR-1006-69, Cytiva) diluted 10 times as an experimental buffer. Each cycle for the affinity assay included capture of the molecule to be studied, binding of one concentration of the antigen, and chip regeneration. The antigen after gradient dilution (when the antigen bound to the molecule to be studied, the antigen concentration gradient was 0-40 nM) flowed over the chip surface in an order from low to high concentrations at a flow rate of 30 μL/min, with the binding time of 180 s and the dissociation time of 600 s. Finally, the chip was regenerated using 10 mM Glycine-HCl, pH 1.5 (BR-1003-54, Cytiva). Data results were analyzed using Biacore T200 analysis software (version No. 3.1) using a 1:1 binding model.

Figure 3:
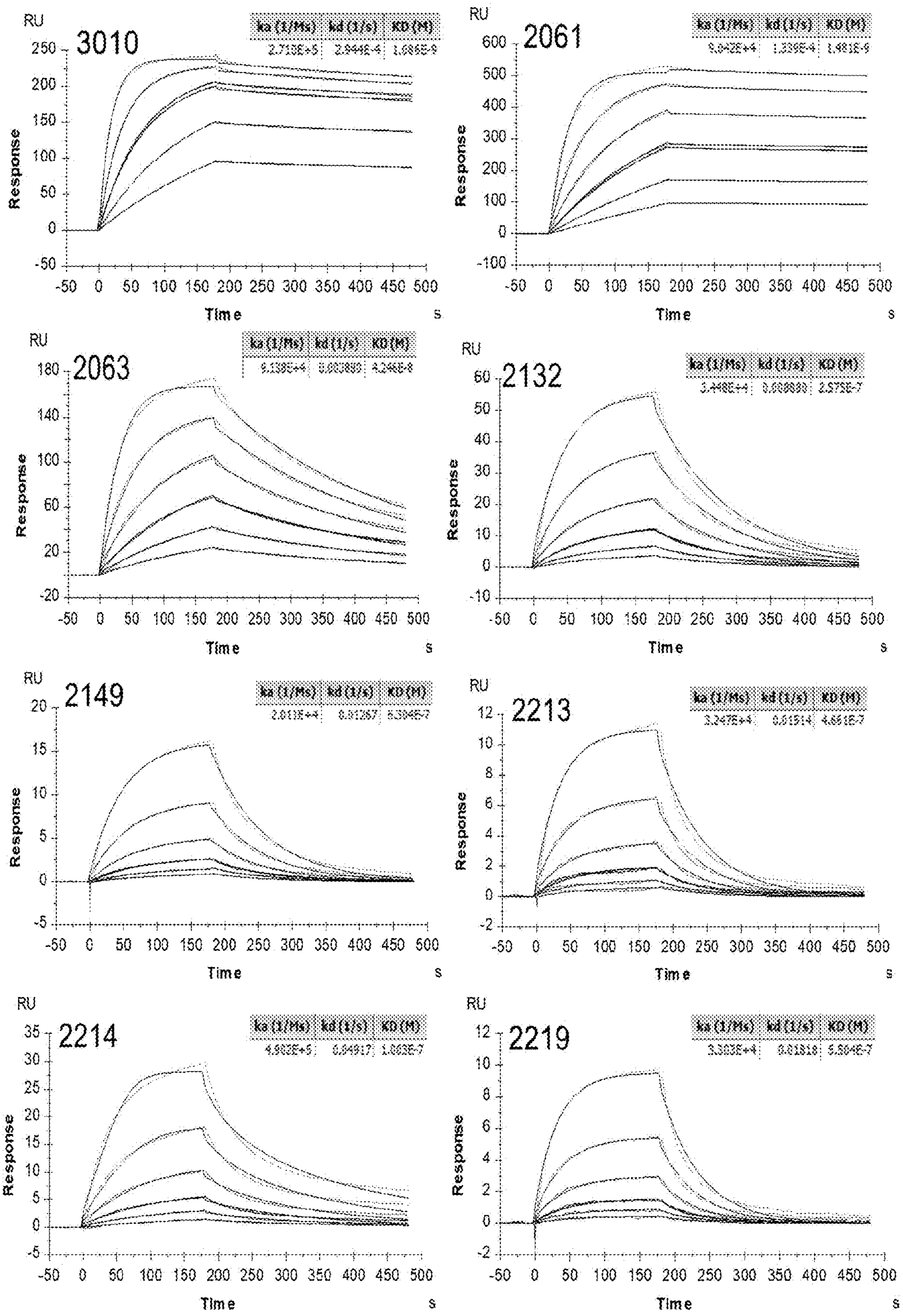
FIG. 3 shows binding curves of immunoconjugates and a control molecule to IL-2Rβγ.

Table 2 and FIG. 3 show the binding constants and binding curves for the immunoconjugates or control molecule to IL-2Rβγ, respectively, wherein 3010 was the wild-type IL-2 sequence fused to Fc (see sequence listing) with the affinity of 1.09 nM; 2061 (derived from US20180326010A1) was the control molecule, and 2061 had the affinity of 1.48 nM for IL-2Rβγ; the IL-2 immunoconjugates of this study had weaker affinities than that of 3010 and 2061.

Figure 4:
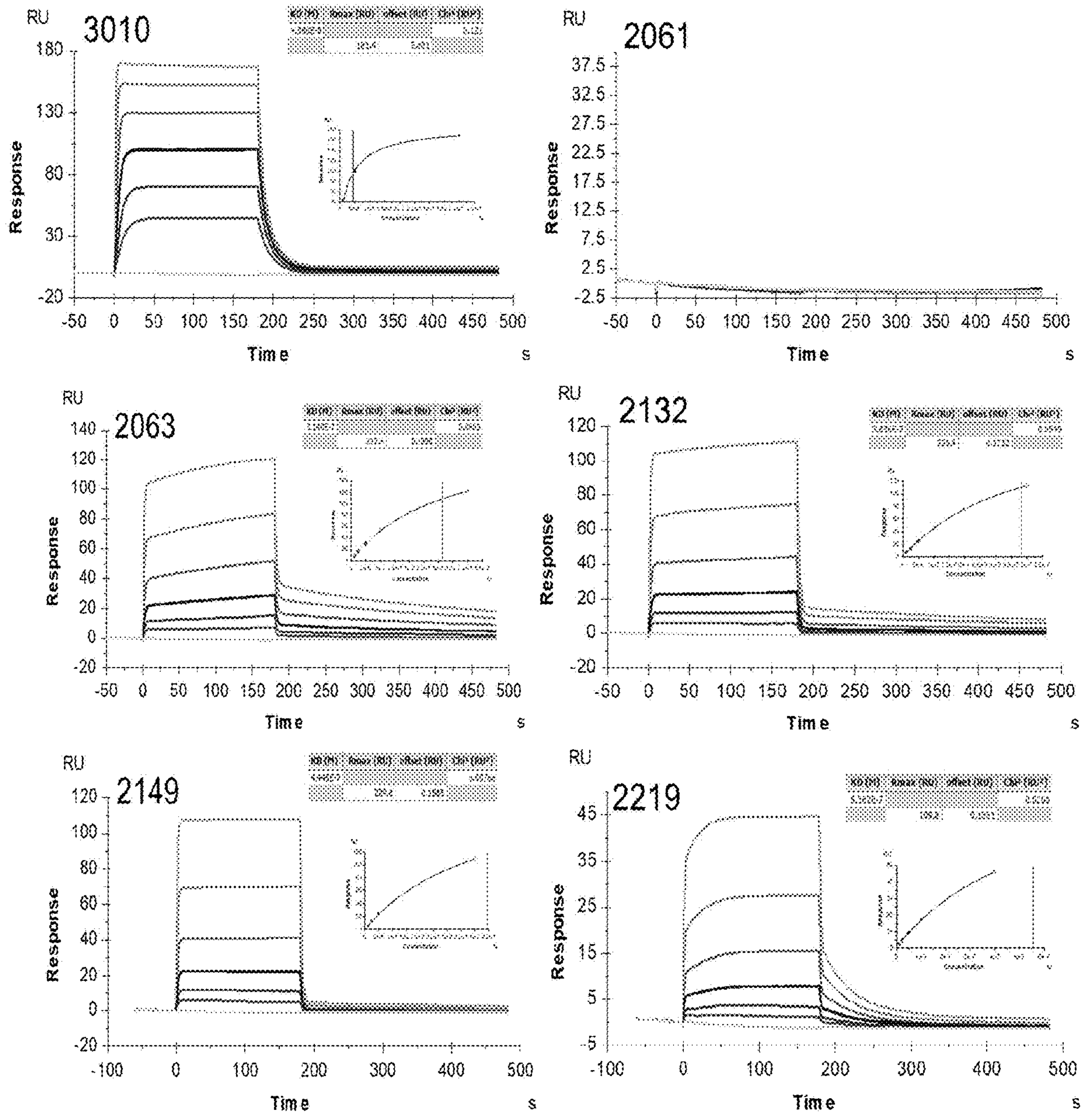
FIG. 4 shows binding curves of the immunoconjugates or the control molecule to IL-2Rα.
Figure 4:
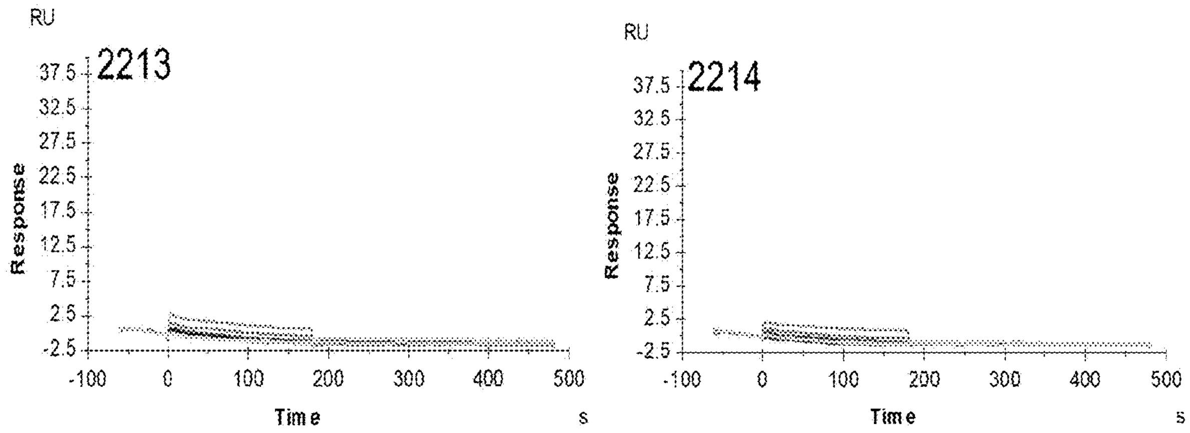

Table 3 and FIG. 4 show the affinity and binding curves for the immunoconjugates or control molecule to IL-2Rα, respectively, wherein 3010 had the affinity of 4.38E-08 M for IL-2Rα; there was no binding in 2061; the binding of the bispecific molecules of this study to IL-2Rα was weaker than that of the wild-type IL-2 but stronger than that of the control molecule 2061.

Figure 5:
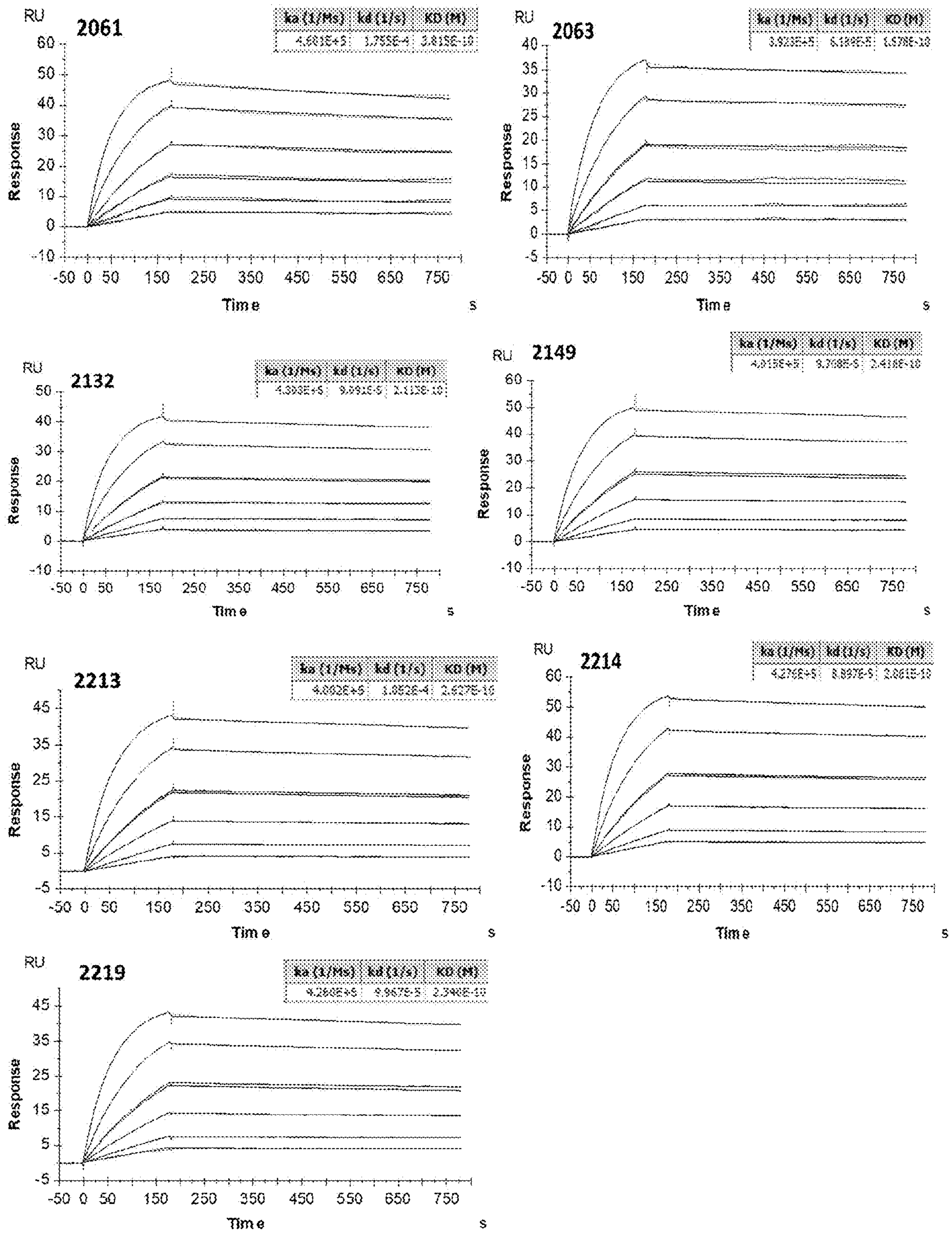
FIG. 5 shows binding curves of the immunoconjugates or the control molecule to human PD1.

Table 4 and FIG. 5 show the affinity and binding curves for the immunoconjugates or control molecule to human PD1 respectively, wherein all the control molecule and the molecules of this study had very strong affinity for human PD1.

TABLE 2

Binding constants of immunoconjugates or control molecule to IL-2Rβγ

| Sample (molecule No.) | Ka(1/Ms) | Kd(1/s) | KD(M) |
|---|---|---|---|
| 3010 | 2.71E+05 | 2.94E−04 | 1.09E−09 |
| 2061 | 9.04E+04 | 1.34E−04 | 1.48E−09 |
| 2063 | 9.14E+04 | 3.88E−03 | 4.25E−08 |
| 2132 | 3.45E+04 | 8.88E−03 | 2.58E−07 |
| 2149 | 2.01E+04 | 1.27E−02 | 6.30E−07 |
| 2213 | 3.25E+04 | 1.51E−02 | 4.66E−07 |
| 2214 | 4.90E+05 | 4.92E−02 | 1.00E−07 |
| 2219 | 3.30E+04 | 1.82E−02 | 5.51E−07 |

TABLE 3

Affinity of immunoconjugates or control molecule for IL-2Rα

| Sample (molecule No.) | KD (M) |
|---|---|
| 3010 | 4.38E−08 |
| 2061 | N.B |
| 2063 | 3.14E−07 |
| 2132 | 3.84E−07 |
| 2149 | 4.45E−07 |
| 2213 | Weak binding |
| 2214 | Weak binding |
| 2219 | 5.56E−07 |

TABLE 4

Affinity of immunoconjugates or control molecule for human PD1

| Sample (molecule No.) | ka (1/Ms) | kd (1/s) | KD (M) |
|---|---|---|---|
| 2061 | 4.601E+5 | 1.755E−4 | 3.815E−10 |
| 2063 | 3.923E+5 | 6.189E−5 | 1.578E−10 |
| 2132 | 4.303E+5 | 9.091E−5 | 2.113E−10 |
| 2149 | 4.015E+5 | 9.708E−5 | 2.418E−10 |
| 2213 | 4.002E+5 | 1.052E−4 | 2.627E−10 |
| 2214 | 4.276E+5 | 8.897E−5 | 2.081E−10 |
| 2219 | 4.260E+5 | 9.967E−5 | 2.340E−10 |

Example 4. In Vitro Activity Assay of Immunoconjugates

I. Activity Assay for PD-1 in CTLL2 (huPD1−) and CTLL2-hPD-1 (huPD1+)

The binding of IL-2 to an IL-2 receptor on the surface of CTLL2 cells will activate the CTLL2 JAK-STAT signaling pathway and trigger reporter gene signals. The overexpression of human PD-1 (hPD-1, uniprot: Q15116) on the surface of the CTLL2 cell line can further enhance the CTLL2 JAK-STAT signaling pathway under an enrichment effect of hPD-1.

Construction of CTLL2-hPD-1 Cell Line:

Construction and Packaging of Lentvirus+hPD-1 Lentivirus:

1. 6×10^6 293T cells were plated in a T75 culture flask with a suitable confluence of 75%-80%.
2. The packaging system was uniformly mixed as listed in the following table and left to stand at room temperature for 15 min.

| Component | Amount of addition |
|---|---|
| Opti-MEM (gibco) | 1 ml |
| pWPT + hPD1 (Genewiz) | 8 ug |
| psPAX2(SynbioTech) | 4 ug |
| pMD2g(SynbioTech) | 2 ug |
| PEI (Polysciences) | 42 ug |

3. The medium in the culture flask was previously discarded, and 6 mL of DMEM (ATCC) fresh medium containing 10% FBS (PEAK) was added.
4. The packaging system prepared in step (2) was added to the replaced medium in step (3), and the culture flask was left to stand in an incubator at 37° C. with 5% $CO_2$ for 4-6 h.
5. After the culture flask was left to stand in the incubator at 37° C. with 5% $CO_2$ for 4-6 h, the medium was replaced with a 2% reduced serum DMEM medium, and viruses were separately collected at 48 h and 72 h.
6. Virus concentration: the collected virus was centrifuged and filtered through a 0.45 μm filter membrane. According to the volume ratio of each component, i.e., virus supernatant:50% PEG8000:5 M NaCl=87:10:3, the mixture was uniformly mixed and concentrated at 4° C. overnight. The mixture was centrifuged at 4° C. and 3000 g for 20 min, the virus was resuspended in 1 mL of CTS medium (Gibco, A3021002), and the mixed solution was lysed at 4° C. and stored at −80° C.

CTLL2 (Promega, CS2028B04) was infected with Lentvirus+hPD-1, and a CTLL2-hPD-1 stably transfected cell line was obtained by pressurized screening and sorting.

Experimental Method:

1. An assay medium was prepared using 1% MEM NEAA (Gibco, 11140-050), 10% FBS (PEAK, PS-FB1) and 89% IMDM (Gibco, 12440-053).
2. CTLL2 or CTLL2-hPD-1 cells were washed 2 times with the assay medium.
3. The density of CTLL2 or CTLL2-hPD-1 cells was adjusted using an assay medium containing 0.4 ng/mL rhIL2 (R&D, 202-IL), and the cells were plated in the middle of a 96-well white cell culture plate (NUNC) with 50000 cells in each well.
4. An equal volume of the assay medium was plated in the marginal wells, and the cells were starved at 37° C. with 5% $CO_2$ for 18-20 h.
5. The diluted test immunoconjugate molecules were separately added to the cell plate, and the plate was incubated at 37° C. with 5% $CO_2$ for 6 h.
6. The culture plate was taken out and equilibrated to room temperature for 15-20 min; an equal volume of Luciferease assay system reagent (Bio-Glo) was added to each well; the plate was incubated at room temperature for 5-15 min and read using a microplate reader (Molecular Devices).

Figure 6:
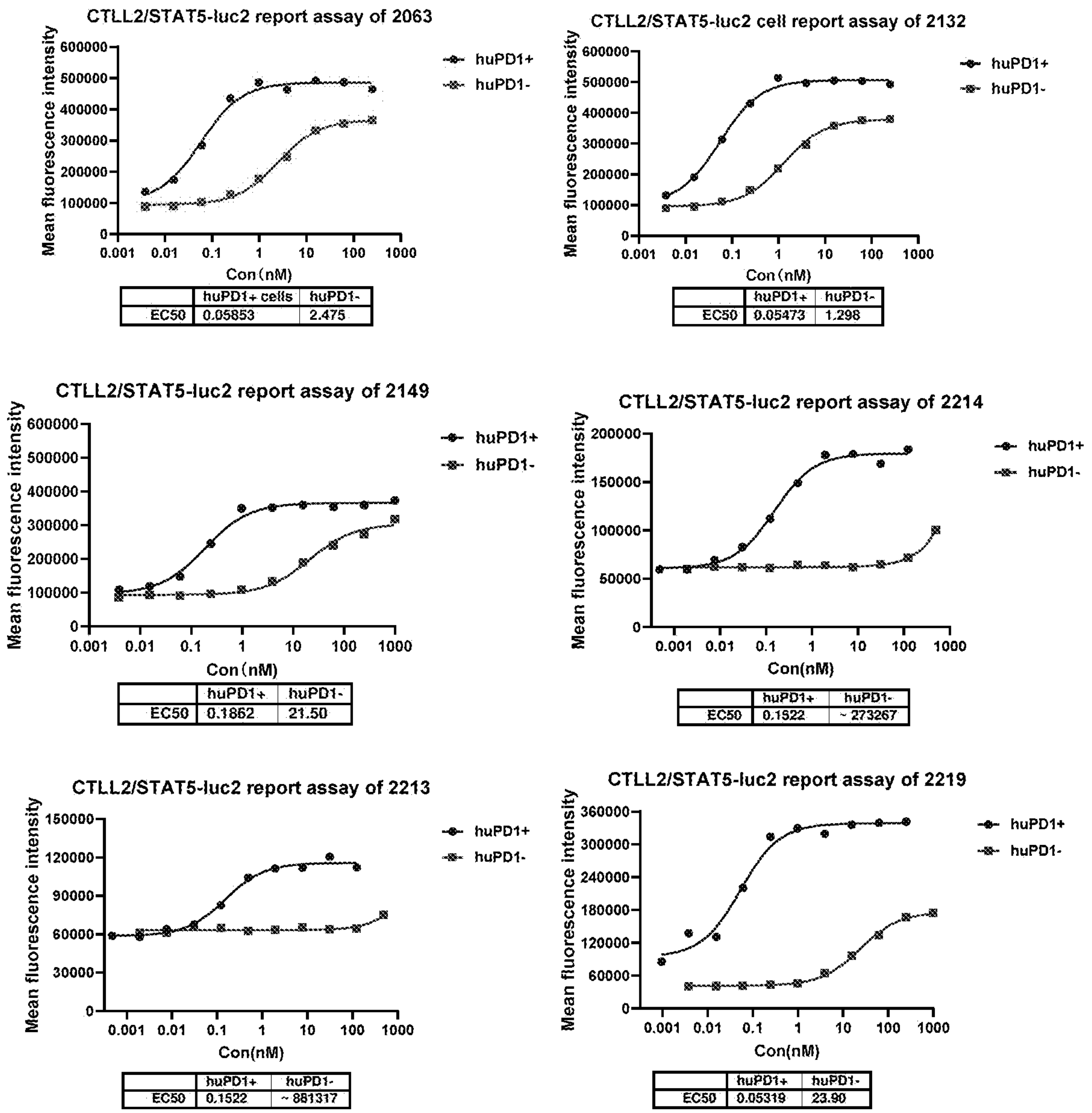
FIG. 6 shows activity assays of the immunoconjugates or the control molecule in CTLL2WT (huPD1−) and CTLL2-hPD-1 (huPDI+).

The results are shown in FIG. 6. The results in FIG. 6 show that the αPD-1/IL-2m immunoconjugates of this study had stronger activity in PD-1-positive CTLL2 cells than that in PD-1-negative CTLL2, wherein 2132 had 24-fold selectivity in activity ($EC_{50}$) between the two cells, 2063 had 42-fold selectivity, 2149 had 115-fold selectivity, 2219 had 500-fold selectivity, and 2213 and 2214 had more than 10000-fold selectivity. The results indicate that the immunoconjugate molecules of the present invention can selectively activate PD-1-positive CTLL2 cells.

II. Detection of pSTAT5 Signals in PBMCs by αPD-1/IL2m Immunoconjugate Molecules The binding of IL-2 to an IL-2 receptor on the surface of a T cell will activate the JAK-STAT signaling pathway in T lymphocytes. The phosphorylation level of STAT5 is an important measure for the activation level of this signaling pathway.

Experimental Method

1. Thawing of PBMCs
   (1) PBMCs (Miao Tong Biological Science & Technology Co., Ltd., Catalog No. PB100C) cryopreserved in liquid nitrogen were thawed by rapidly shaking at 37° C.
   (2) The cells were added slowly to 10 mL of CTS medium (Gibco) which needed to be preheated at 37° C. in advance, and 100 μL of DNase (STRMCELL, Catalog No. 07900) was added.
   (3) The medium was centrifuged at 300 g for 8 min, and the supernatant was removed.
   (4) the residue was resuspended in 10 mL of CTS; the suspension was transferred to a T75 culture flask; and the mixture was stabilized in a 5% incubator at 37° C. overnight.
2. pSTAT5 Test
   (1) PD-1 mAb (Innovent, ADI-11416) was labeled with Alexa Fluor™ 488 Antibody Labeling Kit (Thermo Fisher, A20181), and AF488-anti human PD-1 fluorescent antibodies were prepared, which labeled the suspended PBMCs cultured overnight.
   (2) The labeled suspended PBMCs were plated in a 96-well U-plate at $5\times10^5$ cells/well.
   (3) The test immunoconjugates with different dilution concentrations were separately added to the 96-well plate, and the cells were incubated with the test samples at 37° C. for 30 min.
   (4) The mixtures were centrifuged at 400 g for 5 min, and the supernatants were removed.
   (5) A 4% tissue cell fixation solution (Solarbio, P1110) was added at 200 μL/well, and the plate was centrifuged at room temperature and 400 g for 30 min.
   (6) A perm buffer was added at 200 μL/well, and the plate was left to stand at 4° C. for 30 min and centrifuged at 400 g for 10 min.
   (7) A perm/wash Buffer (BD) was added at 200 μL/well, and the cells were washed twice.
   (8) Antibody stain solutions were prepared. The amount of AF647-pSTAT5 antibody was 3 μL/100 μL perm/wash Buffer/well. The amounts of the remaining stain antibodies were 1 μL/100 μL perm/wash Buffer/well. Incubation was performed at room temperature for 1.5 h, followed by 2 washings with the perm/wash Buffer.

| Name | Manufacturer | Catalog number/model |
|---|---|---|
| BV421 anti-human CD3 | Biolegend | 300434 |
| PE anti-human CD4 | Biolegend | 300508 |
| AF700 anti-human CD8a | Biolegend | 300924 |
| BV785 anti-human CD25 | Biolegend | 356140 |
| Dynabeads Human T-Activator CD3/CD28 | Invitrogen | 11131D |
| AF647-pSTAT5 antibody | BD | 562076 |
| AlexaFluor ™488Antibody Labeling Kit | Thermo Fisher | A20181 |
| Perm/Wash Buffer | BD | 554723 |
| Perm BufferIII | BD | 558050 |
| Human IgG Isotype | abcam | Ab206195 |

(9) Resuspension was performed in 150 μL perm/wash Buffer/well, followed by a flow cytometry assay.

III. Detection of pSTAT5 Signals in Activated PBMCs by Immunoconjugate Molecules The effects of the immunoconjugates on pSTAT5 signals in the activated T lymphocytes were explored and validated under the action of PD-1 after the activation of T lymphocytes.

1. Thawing of PBMCs
   (1) PBMCs cryopreserved in liquid nitrogen were thawed by rapidly shaking at 37° C.
   (2) The cells were added slowly to 10 mL of CTS culture medium (preheated at 37° C. and containing 100 μL of DNase).
   (3) The medium was centrifuged at 300 g for 8 min, and the supernatant was removed.
   (4) the residue was resuspended in 10 mL of CTS; the suspension was transferred to a T75 culture flask; and the mixture was stabilized in a 5% incubator at 37° C. overnight.
2. Activation and Resting of T Lymphocytes
   (1) The suspended PBMCs cultured overnight were counted, and activated and stimulated for 48 h by adding an equal number of CD3/CD28 Beads.
   (2) The beads and culture medium were removed and the activated cells were washed.
   (3) The activated cells were transferred to a T75 culture flask and rested at 37° C./5% for 48 h.
3. pSTAT5 Test
   (1) PD-1 mAb (Innovent, ADI-11416) was labeled with Alexa Fluor™ 488 Antibody Labeling Kit (Thermo Fisher, A20181), and AF488-anti human PD-1 fluorescent antibodies were prepared, which labeled the activated and resting T cells.
   (2) The cells were plated in a 96-well U-plate at $5\times10^5$ cells/well.
   (3) Different diluted test molecules were separately added to the 96-well plate, and the cells were incubated with the test molecules at 37° C. for 30 min.
   (4) The mixtures were centrifuged at 400 g for 5 min, and the supernatants were removed.
   (5) A 4% tissue cell fixation solution was added at 200 μL/well, and the plate was centrifuged at room temperature and 400 g for 30 min.
   (6) A perm buffer was added at 200 μL/well, and the plate was left to stand at 4° C. for 30 min and centrifuged at 400 g for 10 min.
   (7) A perm/wash Buffer was added at 200 μL/well, and the cells were washed twice.
   (8) Antibody stain solutions were prepared. The amount of pSTAT5 antibody (BD) was 3 μL/100 μL perm/wash Buffer/well. The amounts of the remaining stain antibodies were 1 μL/100 μL perm/wash Buffer/well. Incubation was performed at room temperature for 1.5 h, followed by 2 washings with the perm/wash Buffer.

(9) Resuspension was performed in 150 μL perm/wash Buffer/well, followed by a flow cytometry assay.

Figure 7:
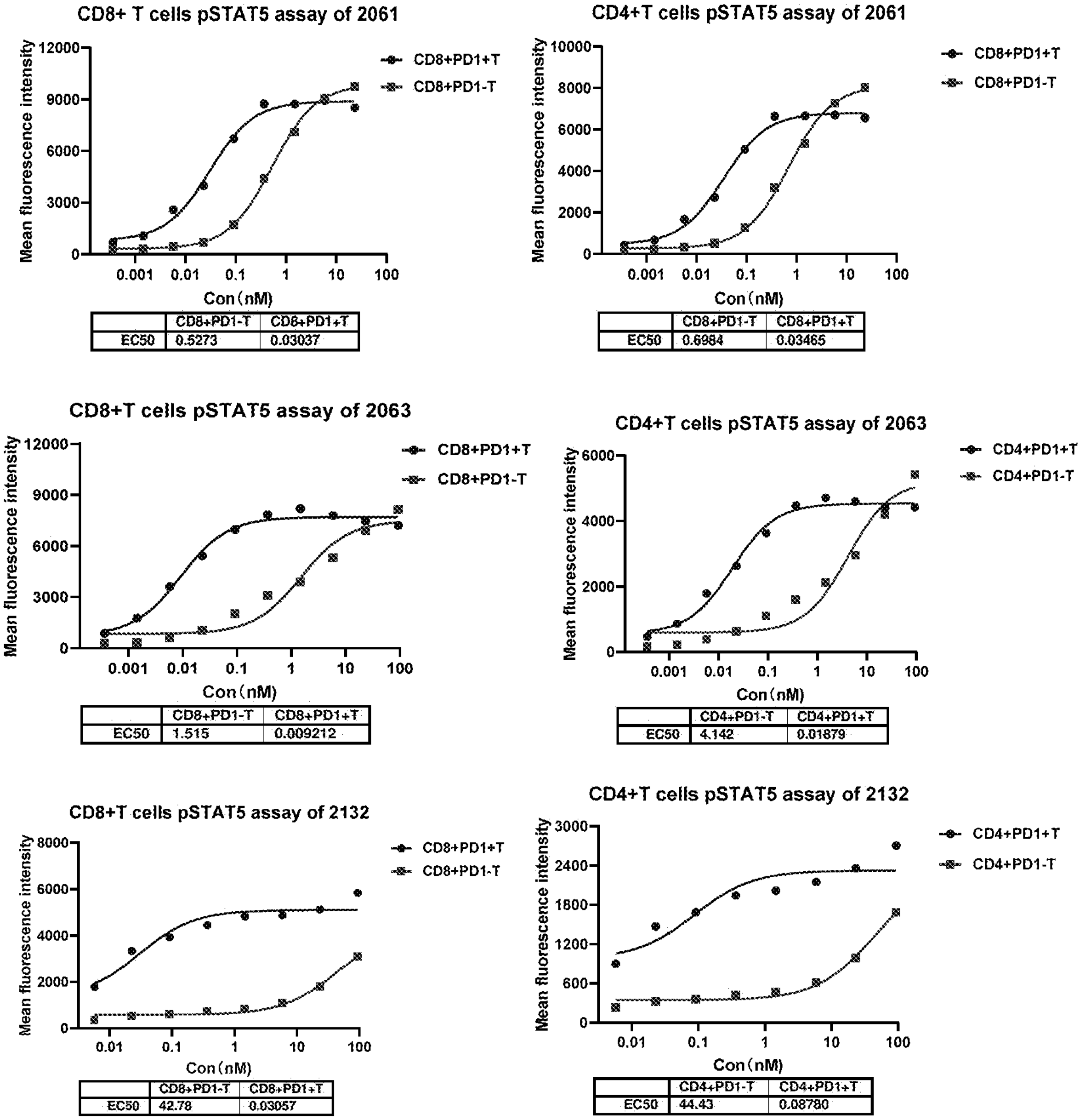
FIG. 7 shows the activities of the immunoconjugates or the control molecule in T cell populations (CD4 or CD8) of PD-1− and PD-1+ separately.
Figure 7:
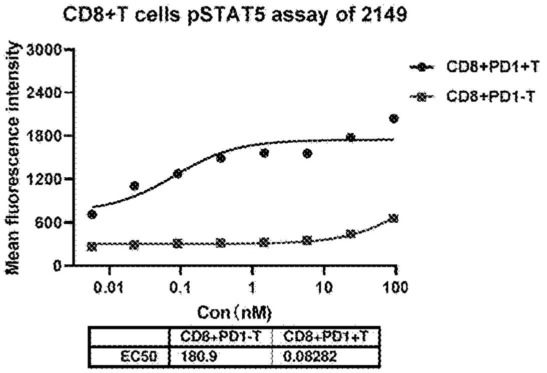
Figure 7:
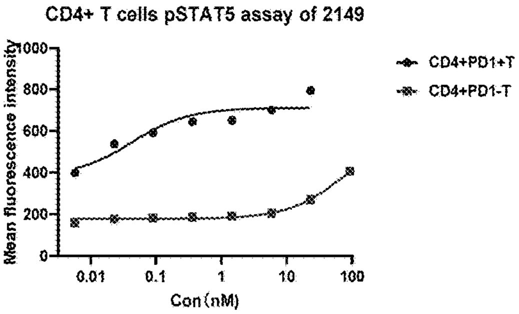
Figure 7:
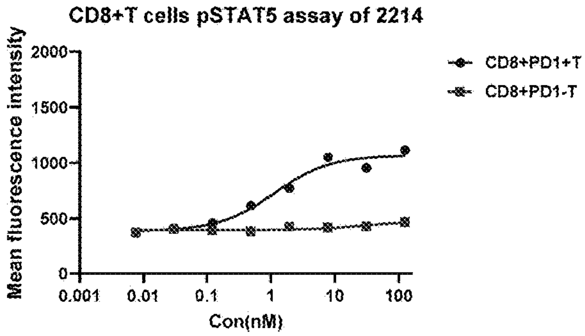
Figure 7:
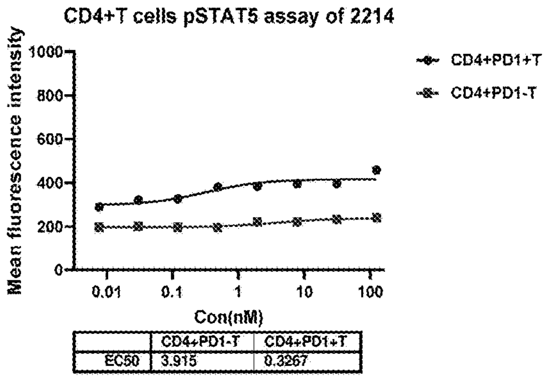
Figure 7:
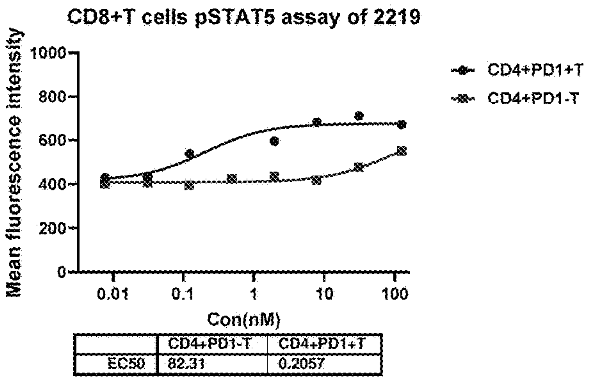
Figure 7:
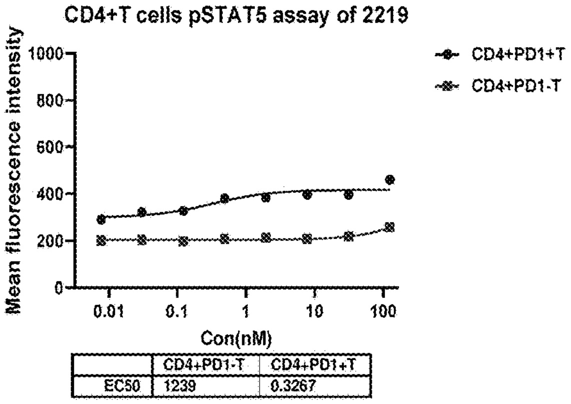

The results in FIG. 7 show that the activities of the molecules of this study were weaker than that of the control molecule 2061 in PD-1-negative (PD-1−) T cells (CD4+PD1−T or CD8+PD1−T); in PD-1-positive (PD-1+) T cells (CD4+PD1+T or CD8+PD1+T), the activity of 2063 was superior to that of the control molecule 2061, which indicates that the selectivity of 2063 for PD-1 is greater than that of 2061, and the activities of other molecules of this study in PD-1+ T cells were also weaker than that of 2061, which indicates that the toxicity of the molecules of this study caused by high-activity IL-2 is less than that of 2061, and the dose which can be tolerated in vivo is also higher than that of 2061.

IV. Activity Assay of Immunoconjugates of the Present Invention Using HEK-Blue™ IL-2 Cell Reporter Assay In HEK293 cells, overexpressed IL2R (CD25, CD122 and CD132), JAK3 and STAT5 genes were introduced, an HEK293+hIL2R/SEAP cell line (huPD-1-cells, HEK-Blue™ IL-2 Cells, Invivogen, hkb-il2) with IL2 signaling pathways was constructed, and HEK293+hIL2R/SEAP cell reporter genes were activated under the action of IL2.

Materials

| Name | Manufacturer/brand | Catalog number/model |
|---|---|---|
| DMEM medium | Gibco | 11965-118 |
| Normocin | Invivogen | ANT-NR-1 |
| Penicillin-Streptomycin | Gibco | 15070-063 |
| Australian fetal bovine serum (FBS) | PeakSerum | PS-FB1 |
| HEK-Blue ™ IL-2 Cells | Invivogen | hkb-il2 |
| QUANTI-Blue | Invivogen | REP-QBS2 |
| F96 Micro Well plate | NUNC | 167008 |
| Fluorescent quantitative microplate reader | Molecular Devices | spectra Max I3x |
| Centrifuge | Thermo | ST40R |

Construction of HEK293+hIL2R+hPD-1/SEAP cell line: Lentvirus+hPD-1 lentivirus was constructed and packaged as above, HEK293+h IL2R/SEAP (Invivogen, hkb-il2) was infected with Lentvirus+PD-1, and an HEK293+hIL2R+hPD-1/SEAP stably transfected cell line (huPD-1+ cells) was obtained by pressurized screening and sorting and used for the following experiments.

Experimental Method

1. Cells were digested, the cell density was adjusted, and the cells were plated in 60 wells in the middle of the plate at 50000 cells/well.
2. The diluted immunoconjugates and the control molecule as shown in the figure were separately added to respective cell wells, and the plate was incubated at 37° C. for 20-24 h.
4. 20 μL of cell culture supernatant was taken, and 180 μL of QUANTI-Blue was added; the mixture was left to stand at room temperature for 15 min, and then OD630 was measured.

Figure 8:
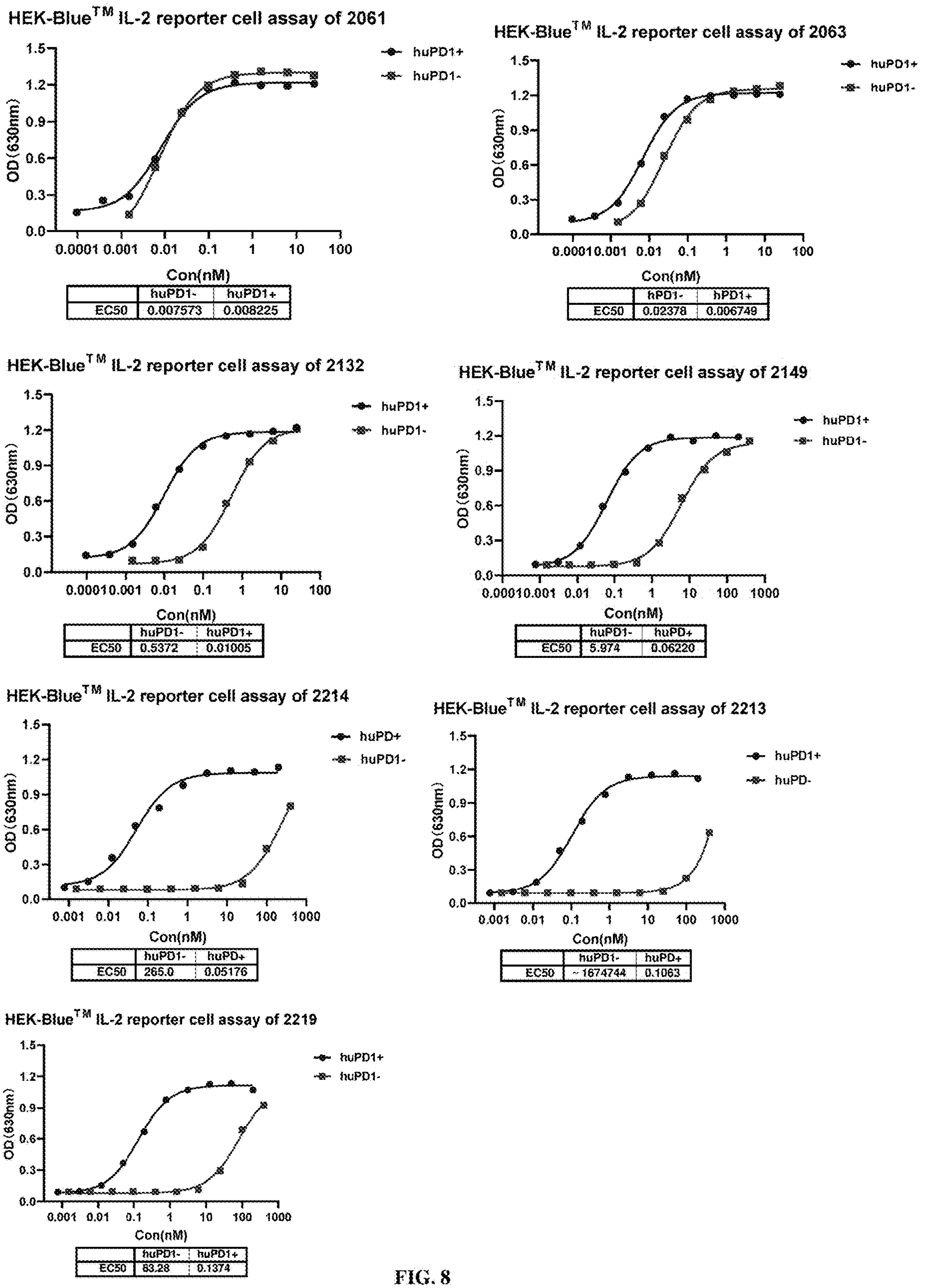
FIG. 8 shows the activities of the immunoconjugates in HEK-Blue™ IL-2 cells (huPD-1− cells) and cells overexpressing PD-1 (HEK293+hIL2R+hPD-1/SEAP stably transfected cell line (huPD-1+ cells)) separately.

HEK-Blue™ IL-2 Cells (huPD-1− cells) were HEK293 cells overexpressing the IL-2 receptor. As can be seen in FIG. 8 and Table 4, the immunoconjugates obtained in this study were at least 3.14 times less active in IL-2 than 2061, with the maximum reduction being 2.21E+08 times.

In the cells overexpressing PD-1 (HEK293+hIL2R+hPD-1/SEAP stably transfected cell line (huPD-1+ cells)), the immunoconjugates could achieve very strong IL-2 activity, and maintain very high selectivity for the two cells, for example, the selectivity of 2063 could reach 3.52 times, the selectivity of 2132 could reach 53.45 times, the selectivity of 2149 could reach 96.04 times, the selectivity of 2219 reached 606.11 times, the selectivity of 2214 reached 5119.78 times, and the selectivity of 2213 reached 1.57E+07 times.

TABLE 4

Selective activity of immunoconjugates of this study in PD-1− cells and PD-1+ cells

| | 2061 | 2063 | 2132 | 2149 | 2213 | 2214 | 2219 |
|---|---|---|---|---|---|---|---|
| Fold# | 1 | 3.52 | 53.45 | 96.04 | 1.57E+7 | 5119.78 | 606.11 |

#Fold = $EC_{50}$ of molecule in PD-1− reporter assay/$EC_{50}$ of molecule in PD-1+ reporter assay

Example 5. Experiment on In Vivo Pharmacodynamics of Immunoconjugates

To demonstrate the efficacy of the αPD-1/IL2m immunoconjugates in vivo, hPD-1 knock-in mice were inoculated with MC38 cells (mouse colon cancer cell line, OBiO Technology (Shanghai) Co., Ltd.) to determine the anti-tumor efficacy of the bifunctional PD-1 antibody and IL-2 mutant molecule immunoconjugates (2063 and 2132) of the present invention. SPF female hPD-1 knock-in mice (purchased from Shanghai Model Organisms Center, Inc.) with certificate No. 20170010005748 were used in the experiment.

The MC38 cells were subcultured conventionally for subsequent in vivo study. The MC38 cells were collected by centrifugation and resuspended in PBS (1×) to form a cell suspension with a cell concentration of $5\times10^6$ cells/mL. On day 0, 0.2 mL of the cell suspension was subcutaneously inoculated into the right abdominal region of the hPD-1 knock-in mice to establish MC38 tumor-bearing mouse models.

Six days after the tumor cell inoculation, the tumor volume in each mouse was measured. The mice were divided into groups of 8. The dosages and routes of administration are shown in Table 5.

TABLE 5

Groups, and dosages and routes of administration in the in vivo experiment

| Group | Dose of administration | Administration frequency | Route of administration |
|---|---|---|---|
| h-IgG* | 20 mg/kg | QW x3 | Intraperitoneal injection |
| 2063 | 10 mg/kg | QW x3 | Intraperitoneal injection |
| 2132 | 10 mg/kg | QW x3 | Intraperitoneal injection |

Figure 9A:
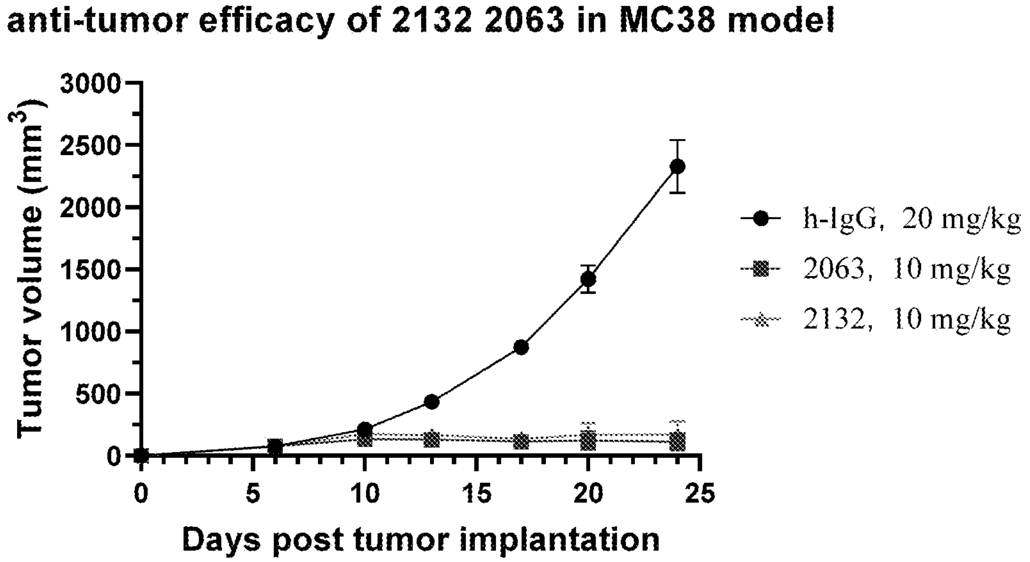
FIG. 9A shows the anti-tumor efficacy of 2132 and 2063 in mice.

*h-IgG was an isotype control antibody, purchased from Equitech-Bio, lot No. 161206-0656.

h-IgG, 2063 and 2132 were used at concentrations of 2 mg/mL, 1 mg/mL and 1 mg/mL, respectively, and administered once every week, for a total of 3 doses (QW×3). Administration was performed on days 6, 13 and 20 after the inoculation of MC38 cells. The tumor volume and body weight of the mice were monitored twice a week for 24 days, as shown in FIG. 9A.

On day 24 after inoculation, the relative tumor growth inhibition (TGI %) was calculated by the following formula: TGI %=100%×(control group tumor volume−treatment group tumor volume)/(control group tumor volume−control group tumor volume before administration). Tumor volume measurement: The maximum length of major axis (L) and maximum length of minor axis (W) of tumors were measured with a vernier caliper, and tumor volume was calculated using the following formula: $V=L\times W^2/2$. The mice were weighted using an electronic balance.

Figure 9B:
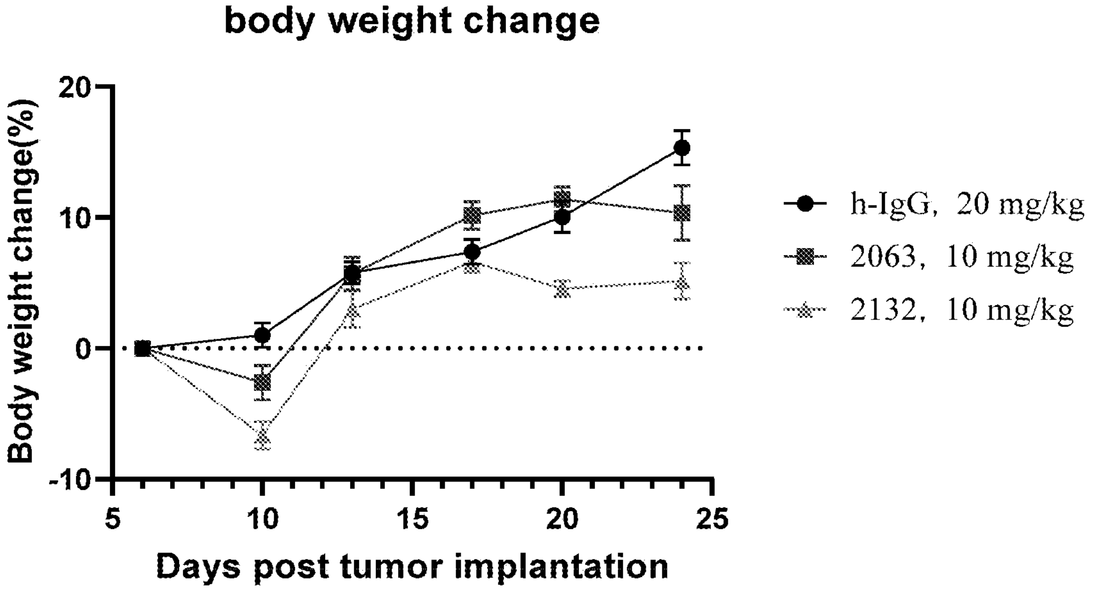
FIG. 9B shows the effect of 2132 and 2063 on mouse body weight.

The tumor growth inhibition results are shown in Table 6: on day 24 after inoculation, 2063 and 2132 had tumor growth inhibition of 98% and 96%, respectively, compared to the 20 mg/kg h-IgG group. Meanwhile, the results of the body weight measurement of mice (FIG. 9B) show that on day 24 after inoculation, there was no significant difference in the body weight of the mice.

TABLE 6

Anti-tumor efficacy statistics

| Group | Tumor volume ($mm^3$) | Tumor growth inhibition (%) |
|---|---|---|
| h-IgG | 2329.61 | N/A |
| 2063 | 112.47 | 98 |
| 2132 | 170.91 | 96 |

To further demonstrate that the efficacy of the αPD-1/IL2m immunoconjugate in vivo was superior to that of the parental anti-PD-1 monoclonal antibody (Sintilimab, also known as IB1308), hPD-1 knock-in mice were inoculated with MC38 cells (mouse colon cancer cell line, OBiO Technology (Shanghai) Co., Ltd.) to determine the anti-tumor efficacy of the immunoconjugate (2063) of the present invention. SPF female hPD-1 knock-in mice (purchased from Shanghai Model Organisms Center, Inc.) with certificate No. 20170010004237 were used in the experiment.

The MC38 cells were subcultured conventionally for subsequent in vivo study. The MC38 cells were collected by centrifugation and resuspended in PBS (1×) to form a cell suspension with a cell concentration of $5\times10^6$ cells/mL. On day 0, 0.2 mL of the cell suspension was subcutaneously inoculated into the right abdominal region of the hPD-1 knock-in mice to establish MC38 tumor-bearing mouse models.

Twelve days after the tumor cell inoculation, the tumor volume in each mouse was measured. The mice were divided into groups of 8. The dosages and routes of administration are shown in Table 7.

TABLE 7

Groups, and dosages and routes of administration in the in vivo experiment

| Group | Dose of administration | Administration frequency | Route of administration |
|---|---|---|---|
| h-IgG* | 10 mg/kg | QW x3 | Intraperitoneal injection |
| 2063 | 10 mg/kg | QW x3 | Intraperitoneal injection |
| IBI308 | 10 mg/kg | QW x3 | Intraperitoneal injection |

Figure 10A:
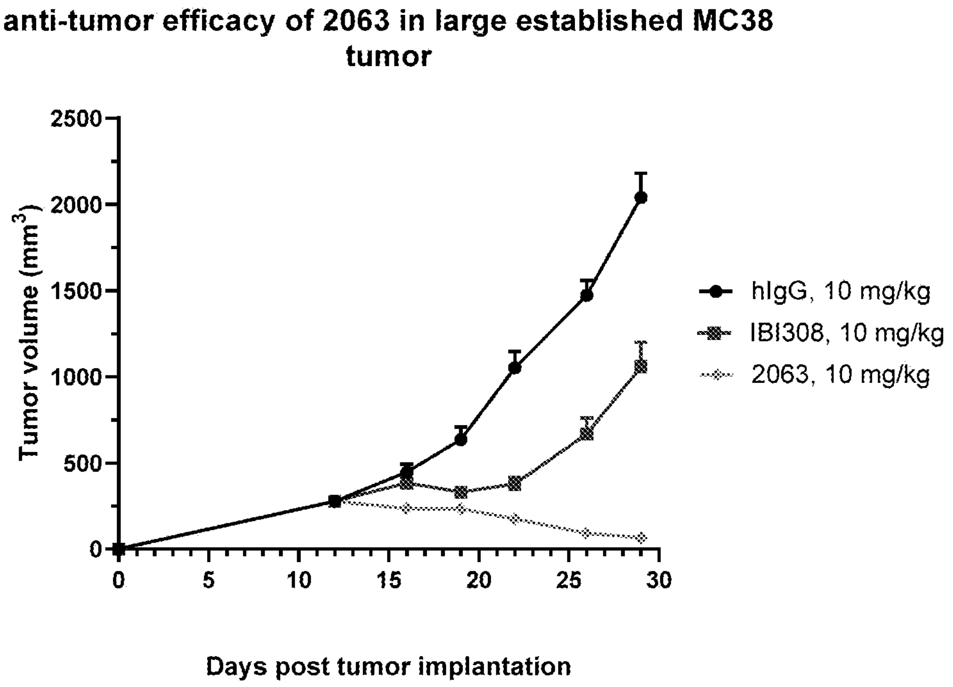
FIG. 10A shows the anti-tumor efficacy of 2063 in mouse MC38 tumor.

*h-IgG was an isotype control antibody, purchased from Equitech-Bio, lot No. 161206-0656.

h-IgG, 2063 and IBI308 were all used at a concentration of 1 mg/mL, and administered once every week, for a total of 3 doses (QW×3). Administration was performed on days 12, 19 and 26 after the inoculation of MC38 cells. The tumor volume and body weight of the mice were monitored twice a week for 29 days, as shown in FIG. 10A. On day 29 after inoculation, the relative tumor growth inhibition (TGI %) was calculated by the following formula: TGI %=100%×(control group tumor volume−treatment group tumor volume)/(control group tumor volume−control group tumor volume before administration). Tumor volume measurement: The maximum length of major axis (L) and maximum length of minor axis (W) of tumors were measured with a vernier caliper, and tumor volume was calculated using the following formula: $V=L\times W^2/2$. The mice were weighted using an electronic balance.

Figure 10B:
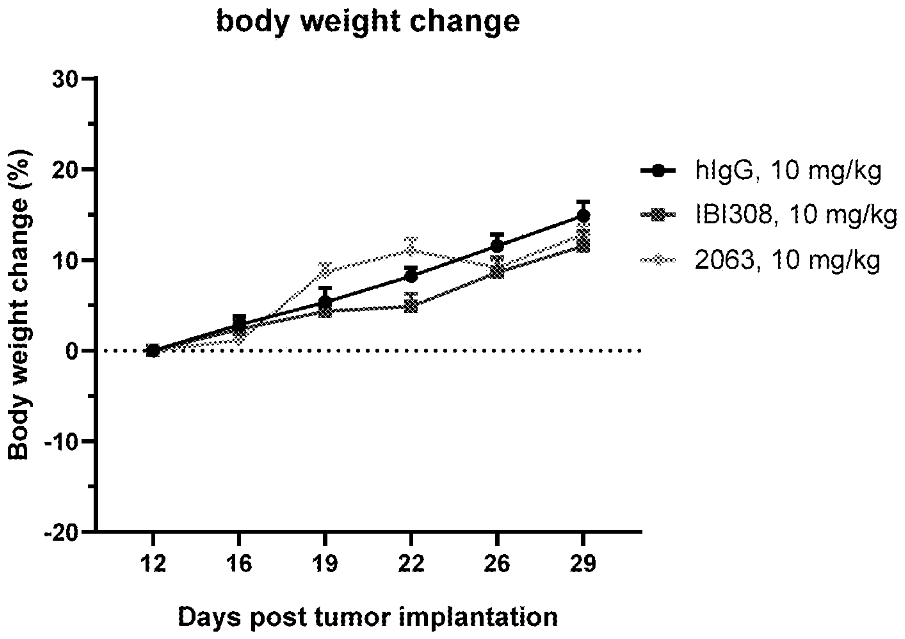
FIG. 10B shows the effect of 2063 on mouse body weight.

The tumor growth inhibition results are shown in Table 8: on day 29 after inoculation, 2063 and IBI308 had tumor growth inhibition of 112% and 56%, respectively, compared to the 20 mg/kg h-IgG group. Meanwhile, the results of the body weight measurement of mice (FIG. 10B) show that on day 29 after inoculation, there was no significant difference in the body weight of the mice.

TABLE 8

Anti-tumor efficacy statistics

| Group | Tumor volume ($mm^3$) | Tumor growth inhibition (%) |
|---|---|---|
| h-IgG | 2041.49 | N/A |
| 2063 | 66.19 | 112 |
| IBI308 | 1057.37 | 55 |

To further demonstrate the efficacy of the αPD-1/IL2m immunoconjugate in vivo, hPD-1 knock-in mice were inoculated with PD-1 antibody-resistant B16F10 cells (mouse melanoma cell line, ATCC, CRL-6475) to determine the anti-tumor efficacy of the αPD-1/IL2m immunoconjugate (2063), the parent anti-PD-1 monoclonal antibody (IBI308) and the combined administration of PD-1 monoclonal antibody and IL2m-Fc fusion protein (2124, IL-2 sequence was identical to that of 2063, and the sequence was shown in the sequence listing) of the present invention. SPF female hPD-1 knock-in mice (purchased from Shanghai Model Organisms Center, Inc.) with certificate No. 20170010004768 were used in the experiment.

The B16F10 cells were subcultured conventionally for subsequent in vivo study. The B16F10 cells were collected by centrifugation and resuspended in PBS (1×) to form a cell suspension with a cell concentration of $2.5\times10^6$ cells/mL. On day 0, 0.2 mL of the cell suspension was subcutaneously inoculated into the right abdominal region of the hPD-1 knock-in mice to establish B16F10 tumor-bearing mouse models.

Seven days after the tumor cell inoculation, the tumor volume in each mouse was measured. The mice were divided into groups of 6. The dosages and routes of administration are shown in Table 9.

TABLE 9

| Groups, and dosages and routes of administration in the in vivo experiment | | | |
|---|---|---|---|
| Group | Dose of administration | Administration frequency | Route of administration |
| h-IgG* | 10 mg/kg | QW x3 | Intraperitoneal injection |
| IBI308 | 10 mg/kg | QW x3 | Intraperitoneal injection |
| IBI308 + 2124 | 10 mg/kg + 6 mg/kg | QW x3 | Intraperitoneal injection |
| 2063 | 10 mg/kg | QW x3 | Intraperitoneal injection |

Figure 11A:
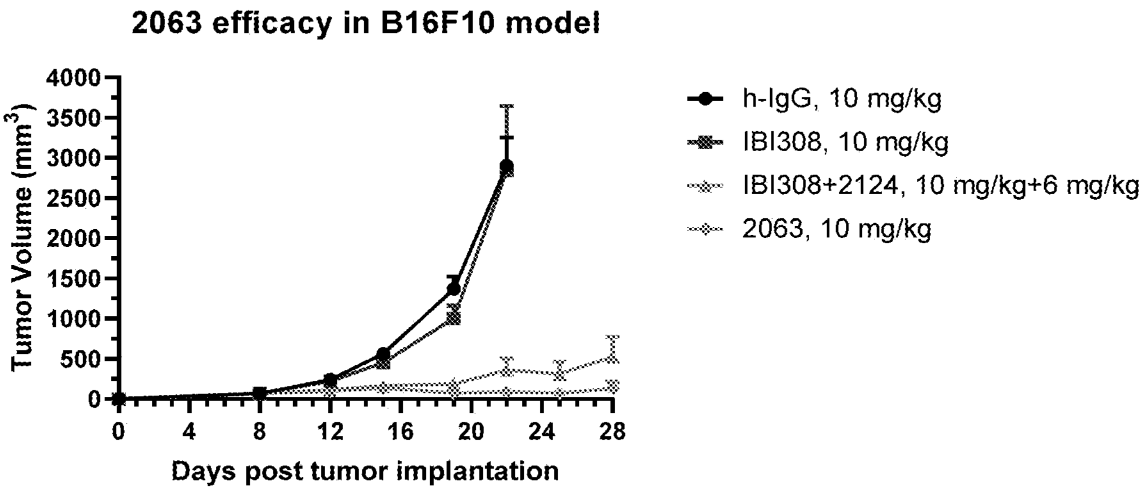
FIG. 11A shows the anti-tumor efficacy of 2063 in mouse B16F10 tumor.
Figure 11B:
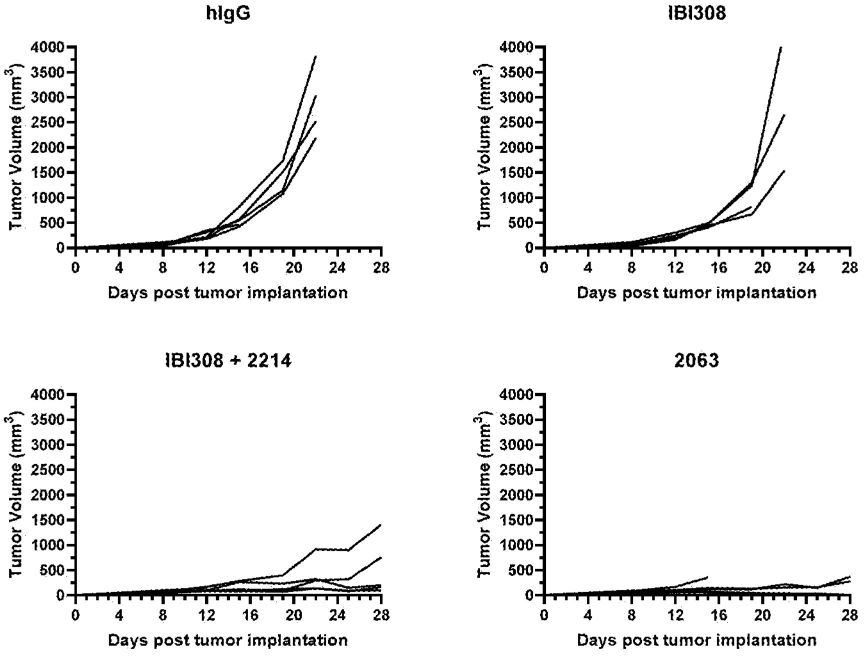
FIG. 11B shows the anti-tumor efficacy of 2063 in the mouse B16F10 tumor, i.e., showing individual tumor values.
Figure 11C:
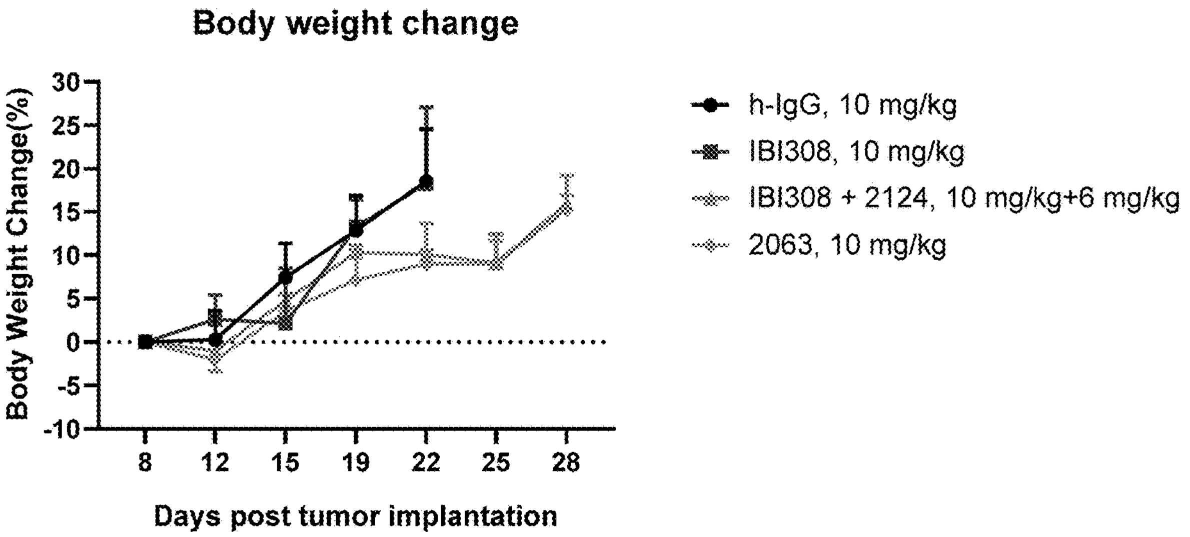
FIG. 11C shows the effect of 2063 on mouse body weight.

*h-IgG was an isotype control antibody, purchased from Equitech-Bio, lot No. 161206-0656.

h-IgG, IBI308, 2124 and 2063 were used at concentrations of 1 mg/mL, 1 mg/mL, 0.6 mg/mL and 1 mg/mL, respectively, and administered once every week, for a total of 3 doses (QW×3). Administration was performed on days 8, 15 and 22 after the inoculation of B16F10 cells. The tumor volume and body weight of the mice were monitored twice a week for 28 days, as shown in FIGS. 11A-11C.

Since the B16F10 cells readily metastasized to induce mouse death, the relative tumor growth inhibition (TGI %) was calculated by the following formula: TGI %=100%×(control group tumor volume−treatment group tumor volume)/(control group tumor volume−control group tumor volume before administration) on day 22 after inoculation. Tumor volume measurement: The maximum length of major axis (L) and maximum length of minor axis (W) of tumors were measured with a vernier caliper, and tumor volume was calculated using the following formula: $V=L\times W^2/2$. The mice were weighted using an electronic balance. Mice with tumor volumes of more than 2000 $mm^3$ were euthanized. If more than half of the deaths occurred in the group, the tumor growth curve for the whole group was not shown at this time point.

The tumor growth inhibition results are shown in Table 10: on day 22 after inoculation, IBI308, IBI308+2214 and 2063 had tumor growth inhibition of 2%, 84% and 99%, respectively, compared to the h-IgG group, and the CR rate of 2063 was significantly superior to that of IBI308 and IBI308 in combination with the non-targeted IL2m-Fc molecule (2124). Meanwhile, the results of the body weight measurement of mice (FIG. 11C) show that during monitoring, there was no significant difference in the body weight of the mice.

TABLE 10

| Anti-tumor efficacy statistics | | | |
|---|---|---|---|
| Group | Tumor volume ($mm^3$) | Tumor growth inhibition (%) @Day 17 | Complete response rate* @Day 28 |
| h-IgG | 2900.61 | N/A | 0/6 |
| IBI308 | 2838.44 | 2 | 0/6 |
| IBI308 + 2214 | 362.03 | 90 | 0/6 |
| 2063 | 90.74 | 99 | 3/6 |

*Complete response rate: the tumor was completely regressed with a tumor volume of 0.

To further demonstrate the efficacy of the αPD-1/IL2m immunoconjugate 2149 of the present invention in vivo, hPD-1 knock-in mice were inoculated with MC38 cells (mouse colon cancer cell line, OBiO Technology (Shanghai) Co., Ltd.) to determine the anti-tumor efficacy of the immunoconjugate (2149) of the present invention. SPF female hPD-1 knock-in mice (purchased from Shanghai Model Organisms Center, Inc.) with certificate No. 20170010006762 were used in the experiment.

The MC38 cells were subcultured conventionally for subsequent in vivo study. The MC38 cells were collected by centrifugation and resuspended in PBS (1×) to form a cell suspension with a cell concentration of $5\times10^6$ cells/mL. On day 0, 0.2 mL of the cell suspension was subcutaneously inoculated into the right abdominal region of the hPD-1 knock-in mice to establish MC38 tumor-bearing mouse models.

Eight days after the tumor cell inoculation, the tumor volume in each mouse was measured. The mice were divided into groups of 8. The dosages and routes of administration are shown in Table 11.

TABLE 11

| Groups, and dosages and routes of administration in the in vivo experiment | | | |
|---|---|---|---|
| Group | Dose of administration | Administration frequency | Route of administration |
| h-IgG* | 40 mg/kg | QW x3 | Intraperitoneal injection |
| 2149, 10 mg/kg | 10 mg/kg | QW x3 | Intraperitoneal injection |
| 2149, 20 mg/kg | 20 mg/kg | QW x3 | Intraperitoneal injection |
| 2149, 40 mg/kg | 40 mg/kg | QW x3 | Intraperitoneal injection |

Figure 12A:
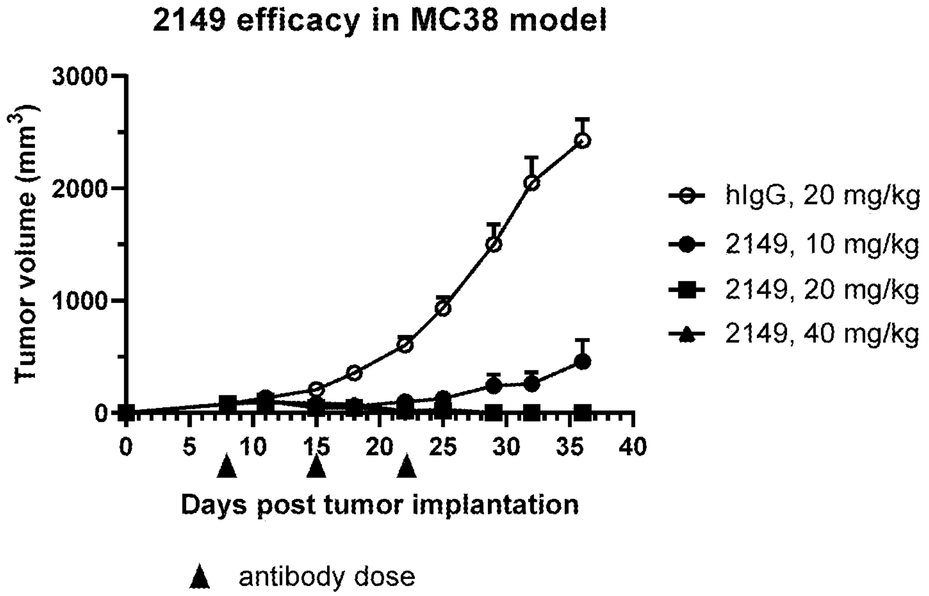
FIG. 12A shows the anti-tumor efficacy of 2149 in the mouse MC38 tumor.
Figure 12B:
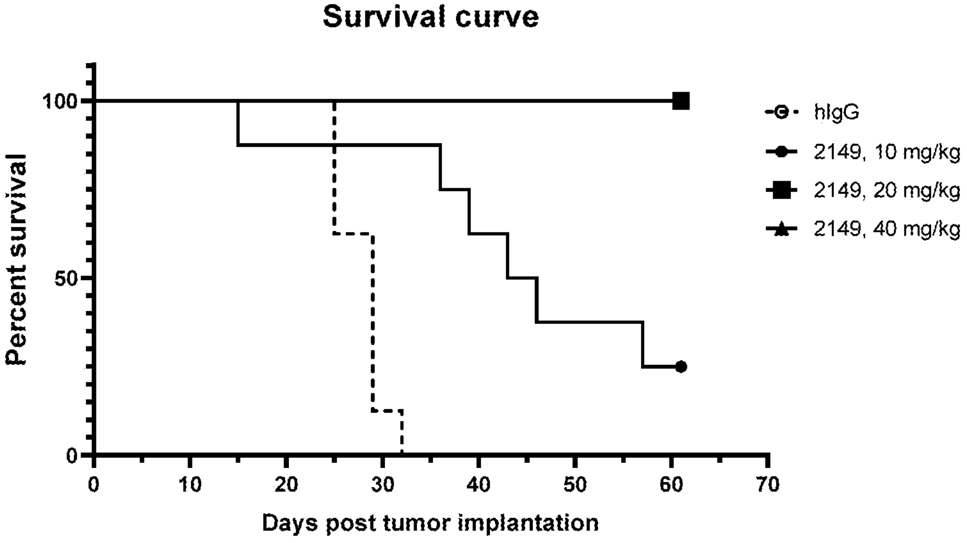
FIG. 12B shows the anti-tumor efficacy of 2149 in the mouse MC38 tumor, i.e., showing a survival curve.

*h-IgG was an isotype control antibody, purchased from Equitech-Bio, lot No. 161206-0656.

h-IgG, 10 mg/kg 2149, 20 mg/kg 2149 and 40 mg/kg 2149 were used at concentrations of 4 mg/mL, 1 mg/mL, 2 mg/mL and 4 mg/mL, respectively, and administered once every week, for a total of 3 doses (QW×3). Administration was performed on days 8, 15 and 22 after the inoculation of MC38 cells. The tumor volume and body weight of the mice were monitored twice a week, as shown in FIGS. 12A-12B. Mice with tumor volumes of more than 2000 $mm^3$ were euthanized, and the mice were monitored throughout the experiment for 61 days. Since the mice with tumor volumes of more than 2000 $mm^3$ in some groups were euthanized, the relative tumor growth inhibition (TGI %) was calculated by the following formula: TGI %=100%×(control group tumor volume−treatment group tumor volume)/(control group tumor volume−control group tumor volume before administration) on day 36 after inoculation. Tumor volume measurement: The maximum length of major axis (L) and maximum length of minor axis (W) of tumors were measured with a vernier caliper, and tumor volume was calculated using the following formula: $V=L\times W^2/2$. The mice were weighted using an electronic balance.

Figure 12C:
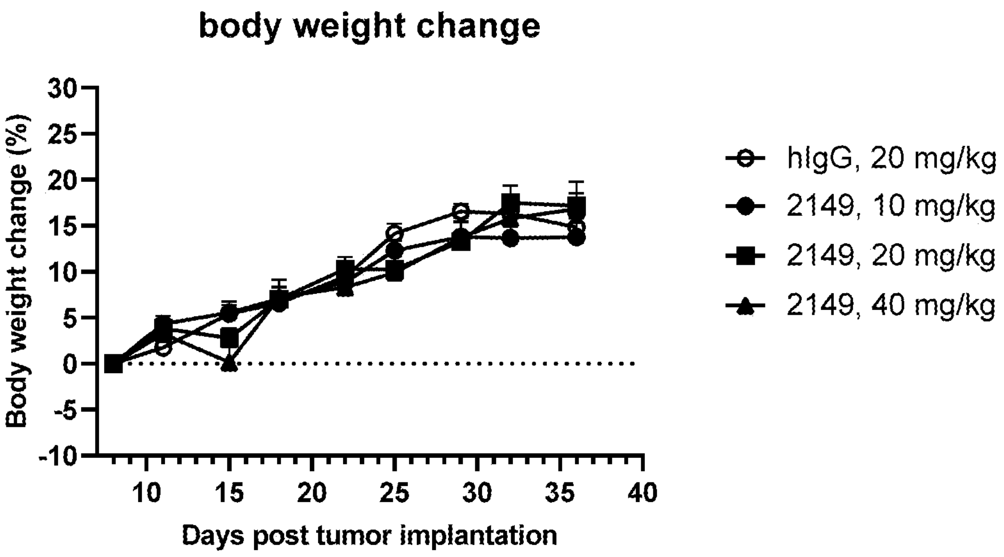
FIG. 12C shows the effect of 2149 on mouse body weight.

The tumor growth curve and survival curve in FIGS. 12A and 12B show that the anti-tumor efficacy of the 2149 molecule at different doses was dose-dependent, and the tumors in mice were completely regressed in the 20 mg/kg and 40 mg/kg groups. Moreover, this advantage was also shown in the survival curve of FIG. 12B, i.e., the tumors in mice were completely regressed in the 20 mg/kg and 40 mg/kg groups, while the tumors in only 2 out of 8 mice were completely regressed in the 10 mg/kg group. The tumor growth inhibition results are shown in Table 12: on day 36 after inoculation, 10 mg/kg 2149, 20 mg/kg 2149 and 40 mg/kg 2149 had tumor growth inhibition of 84%, 103% and 103%, respectively, compared to the h-IgG group. Meanwhile, the results of the body weight measurement of mice (FIG. 12C) show that on day 36 after inoculation, there was no significant difference in the body weight of the mice.

TABLE 12

Anti-tumor efficacy statistics

| Group | Tumor volume ($mm^3$) | Tumor growth inhibition (%) @Day 17 | Complete response rate* @Day 36 |
|---|---|---|---|
| h-IgG | 2426.63 | N/A | 0/8 |
| 2149, 10 mg/kg | 458.62 | 84 | 2/8 |
| 2149, 20 mg/kg | 0 | 103 | 8/8 |
| 2149, 40 mg/kg | 0 | 103 | 8/8 |

*Complete response rate: the tumor was completely regressed with a tumor volume of 0.

To demonstrate the efficacy of the immunoconjugate 2149 in vivo, hPD-1 knock-in mice were inoculated with PD-1 antibody-resistant B16F10 cells (mouse melanoma cell line, ATCC, CRL-6475) to determine the anti-tumor efficacy of the bifunctional PD-1 antibody and IL-2 mutant molecule fusion protein (2149) of the present invention. SPF female hPD-1 knock-in mice (purchased from Shanghai Model Organisms Center, Inc.) with certificate No. 20170010007909 were used in the experiment.

The B16F10 cells were subcultured conventionally for subsequent in vivo study. The B16F10 cells were collected by centrifugation and resuspended in PBS (1×) to form a cell suspension with a cell concentration of $2.5\times10^6$ cells/mL. On day 0, 0.2 mL of the cell suspension was subcutaneously inoculated into the right abdominal region of the hPD-1 knock-in mice to establish B16F10 tumor-bearing mouse models.

Six days after the tumor cell inoculation, the tumor volume in each mouse was measured. The mice were divided into groups of 8. The dosages and routes of administration are shown in Table 13.

TABLE 13

Groups, and dosages and routes of administration in the in vivo experiment

| Group | Dose of administration | Administration frequency | Route of administration |
|---|---|---|---|
| h-IgG* | 40 mg/kg | QW x3 | Intraperitoneal injection |
| IBI308, 20 mg/kg | 20 mg/kg | QW x3 | Intraperitoneal injection |
| IBI308, 40 mg/kg | 40 mg/kg | QW x3 | Intraperitoneal injection |
| 2149, 20 mg/kg | 20 mg/kg | QW x3 | Intraperitoneal injection |
| 2149, 40 mg/kg | 40 mg/kg | QW x3 | Intraperitoneal injection |

Figure 13A:
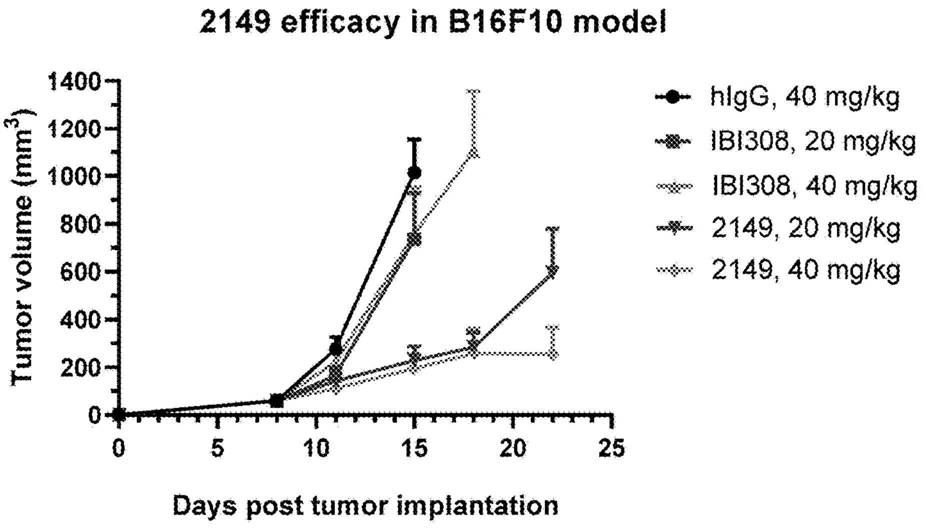
FIG. 13A shows the anti-tumor efficacy of 2149 in the mouse B16F10 tumor.
Figure 13B:
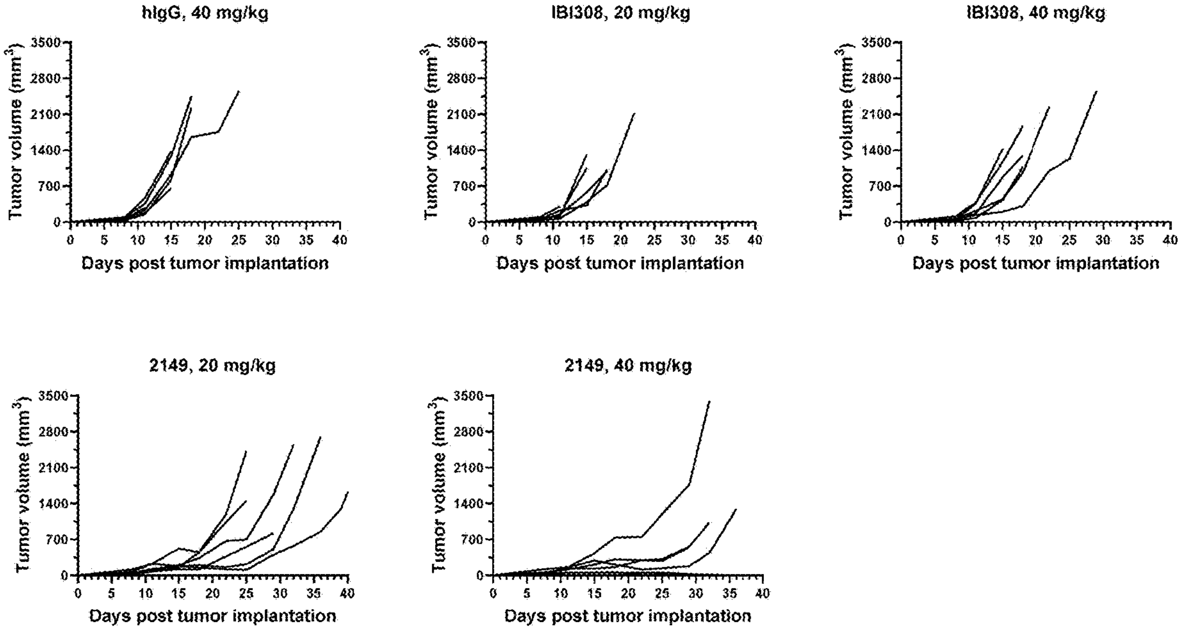
FIG. 13B shows the anti-tumor efficacy of 2149 in the mouse B16F10 tumor, i.e., showing individual tumor values.

*h-IgG was an isotype control antibody, purchased from Equitech-Bio, lot No. 161206-0656.

h-IgG, 20 mg/kg IBI308, 40 mg/kg IBI308, 20 mg/kg 2149 and 40 mg/kg 2149 were used at concentrations of 4 mg/mL, 2 mg/mL, 4 mg/mL, 2 mg/mL and 4 mg/mL, respectively, and administered once every week, for a total of 3 doses (QW×3). Administration was performed on days 8, 15 and 22 after the inoculation of B16F10 cells. The tumor volume and body weight of the mice were monitored twice a week for 22 days, as shown in FIGS. 13A-13B. Since the B16F10 cells readily metastasized to induce mouse death, the relative tumor growth inhibition (TGI %) was calculated by the following formula: TGI %=100%×(control group tumor volume−treatment group tumor volume)/(control group tumor volume−control group tumor volume before administration) on day 15 after inoculation. Tumor volume measurement: The maximum length of major axis (L) and maximum length of minor axis (W) of tumors were measured with a vernier caliper, and tumor volume was calculated using the following formula: $V=L\times W^2/2$. The mice were weighted using an electronic balance. Mice with tumor volumes of more than 2000 $mm^3$ were euthanized.

Figure 13C:
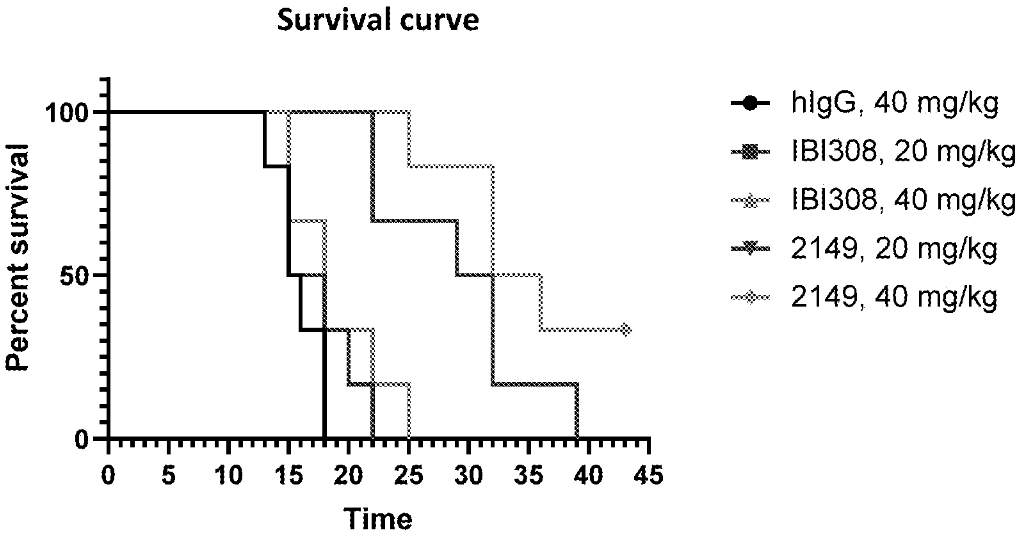
FIG. 13C shows the anti-tumor efficacy of 2149 in the mouse B16F10 tumor, i.e., showing a survival curve.

The tumor growth curves in FIGS. 13A and 13B show that in the PD1 resistance model, IBI308 showed little efficacy, but the 20 mg/kg and 40 mg/kg groups of 2149 exhibited certain anti-tumor effects, and the high-dose group had a better anti-tumor effect than that of the low-dose group, which was simultaneously reflected in the survival curve of the mice; the high-dose group still had complete tumor regression in 2 mice at the experimental end point (FIG. 13C and Table 14).

Figure 13D:
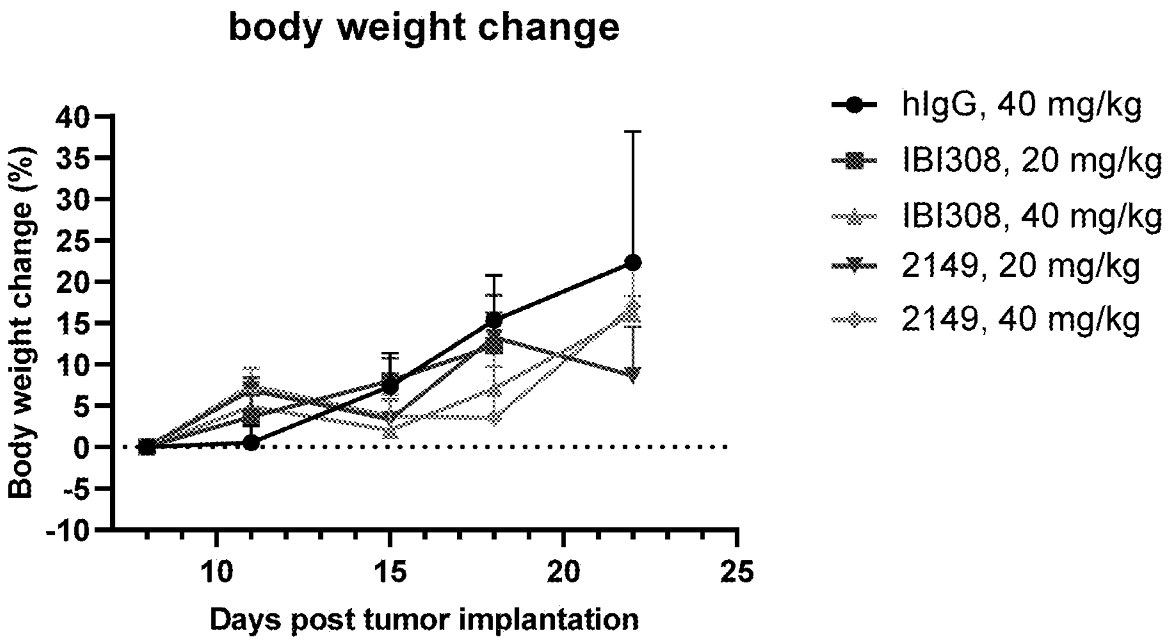
FIG. 13D shows the effect of 2149 on mouse body weight.

The tumor growth inhibition results are shown in Table 12: on day 15 after inoculation, 20 mg/kg IBI308, 40 mg/kg IBI308, 20 mg/kg 2149 and 40 mg/kg 2149 had tumor growth inhibition of 29%, 27%, 82% and 86%, respectively, compared to the 40 mg/kg h-IgG group. Meanwhile, the results of the body weight measurement of mice (FIG. 13D) show that on day 22 after inoculation, there was no significant difference in the body weight of the mice.

TABLE 14

Anti-tumor efficacy statistics

| Group | Tumor volume ($mm^3$) | Tumor growth inhibition (%) @Day 15 | Complete response rate @Day 22 |
|---|---|---|---|
| h-IgG | 1014.92 | N/A | 0/6 |
| IBI308, 20 mg/kg | 735.02 | 29 | 0/6 |
| IBI308, 40 mg/kg | 757.11 | 27 | 0/6 |
| 2149, 20 mg/kg | 227.62 | 82 | 0/6 |
| 2149, 40 mg/kg | 193.90 | 86 | 2/6 |

To demonstrate that the efficacy of the αPD-1/IL2m immunoconjugate 2149 was superior to that of the control drug PD-1-IL2v (molecule No. 2061, sequence derived from US20180326010A1, see also the sequence listing) in vivo, hPD-1 knock-in mice were inoculated with PD-1 antibody-resistant B16F10 cells (mouse melanoma cell line, ATCC, CRL-6475) to determine the anti-tumor efficacy of the bifunctional PD-1 antibody and IL-2 mutant molecule fusion protein (2149) of the present invention. SPF female hPD-1 knock-in mice (purchased from Shanghai Model Organisms Center, Inc.) with certificate No. 20170010008942 were used in the experiment.

The B16F10 cells were subcultured conventionally for subsequent in vivo study. The B16F10 cells were collected by centrifugation and resuspended in PBS (1×) to form a cell suspension with a cell concentration of $2.5\times10^6$ cells/mL. On day 0, 0.2 mL of the cell suspension was subcutaneously inoculated into the right abdominal region of the hPD-1 knock-in mice to establish B16F10 tumor-bearing mouse models.

Eight days after the tumor cell inoculation, the tumor volume in each mouse was measured. The mice were divided into groups of 7. The dosages and routes of administration are shown in Table 15.

TABLE 15

| Group | Dose of administration | Administration frequency | Route of administration |
|---|---|---|---|
| Groups, and dosages and routes of administration in the in vivo experiment | | | |
| h-IgG* | 40 mg/kg | QW x3 | Intraperitoneal injection |
| IBI308 | 40 mg/kg | QW x3 | Intraperitoneal injection |
| 2061, 10 mg/kg | 10 mg/kg | QW x3 | Intraperitoneal injection |
| 2061, 20 mg/kg | 20 mg/kg | QW x3 | Intraperitoneal injection |
| 2061, 40 mg/kg | 40 mg/kg | QW x3 | Intraperitoneal injection |
| 2149, 10 mg/kg | 10 mg/kg | QW x3 | Intraperitoneal injection |
| 2149, 40 mg/kg | 20 mg/kg | QW x3 | Intraperitoneal injection |
| 2149, 40 mg/kg | 40 mg/kg | QW x3 | Intraperitoneal injection |

Figure 14A:
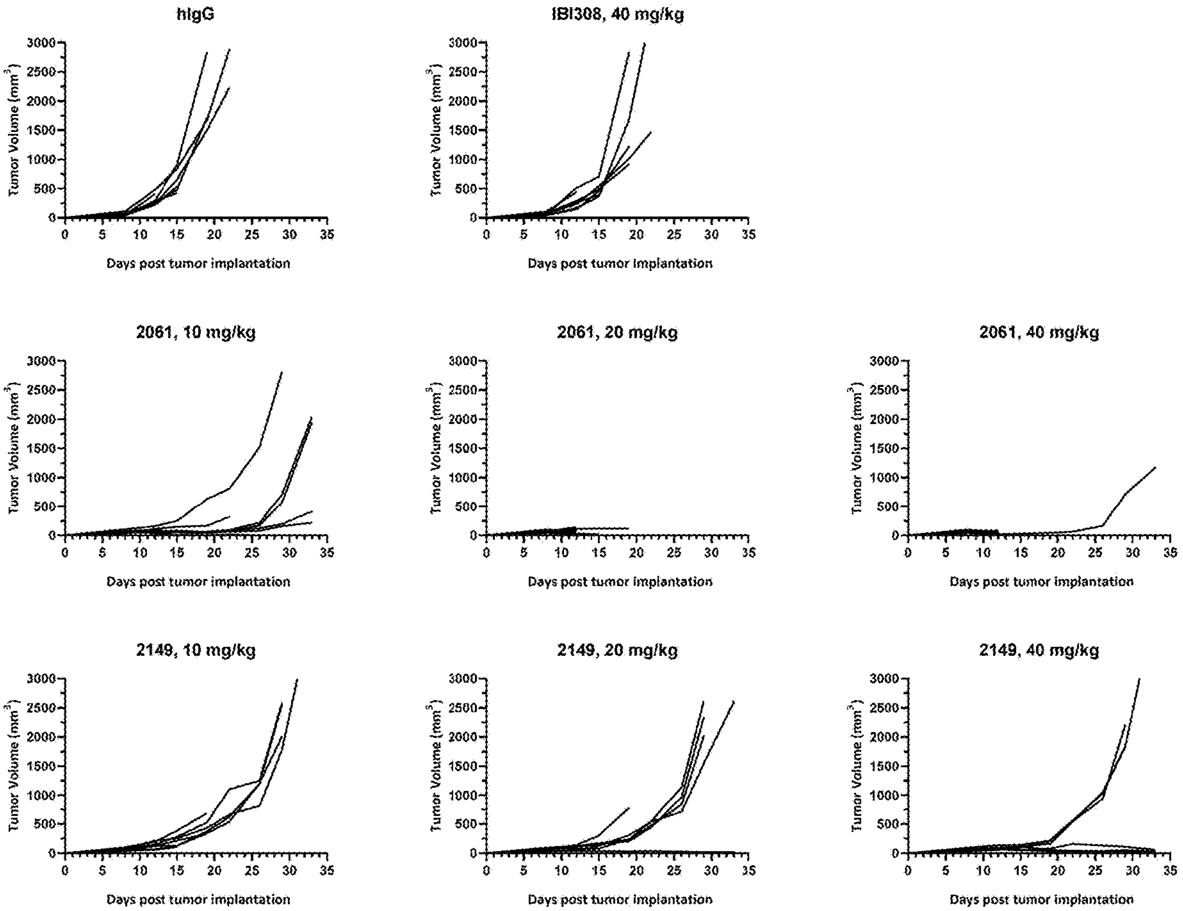
FIG. 14A shows the anti-tumor efficacy of 2061 and 2149 in the mouse B16F10 tumor, i.e., showing individual tumor values.

*h-IgG was an isotype control antibody, purchased from Equitech-Bio, lot No. 161206-0656.

h-IgG, 40 mg/kg IBI308, 10 mg/kg 2061, 20 mg/kg 2061, 40 mg/kg 2061, 10 mg/kg 2149, 20 mg/kg 2149 and 40 mg/kg 2149 were used at concentrations of 4 mg/mL, 2 mg/mL, 4 mg/mL, 2 mg/mL and 4 mg/mL, respectively, and administered once every week, for a total of 3 doses (QW×3). Administration was performed on days 8, 15 and 22 after the inoculation of B16F10 cells. The tumor volume and body weight of the mice were monitored twice a week for 33 days, as shown in FIG. 14A. Since the B16F10 cells readily metastasized to cause mouse death, the relative tumor growth inhibition (TGI %) was calculated by the following formula: TGI %=100%×(control group tumor volume−treatment group tumor volume)/(control group tumor volume−control group tumor volume before administration) on day 19 after inoculation. Tumor volume measurement: the maximum length of major axis (L) and maximum length of minor axis (W) of tumors were measured with a vernier caliper, and tumor volume was calculated using the following formula: $V=L\times W^2/2$. The mice were weighted using an electronic balance. Mice with tumor volumes of more than 2000 $mm^3$ were euthanized. If more than half of the deaths occurred in the group, the tumor growth curve for the whole group was not shown at this time point.

The tumor growth inhibition results are shown in Table 16: on day 19 after inoculation, 40 mg/kg IBI308, 10 mg/kg 2061, 10 mg/kg 2149, 20 mg/kg 2149 and 40 mg/kg 2149 had tumor growth inhibition of 21%, 96%, 79%, 87% and 97%, respectively, compared to the 40 mg/kg h-IgG group. In the 20 mg/kg and 40 mg/kg groups of 2061, TGI was not calculated because the body weight was reduced dramatically and the mice were dead after the first injection.

Figure 14B:
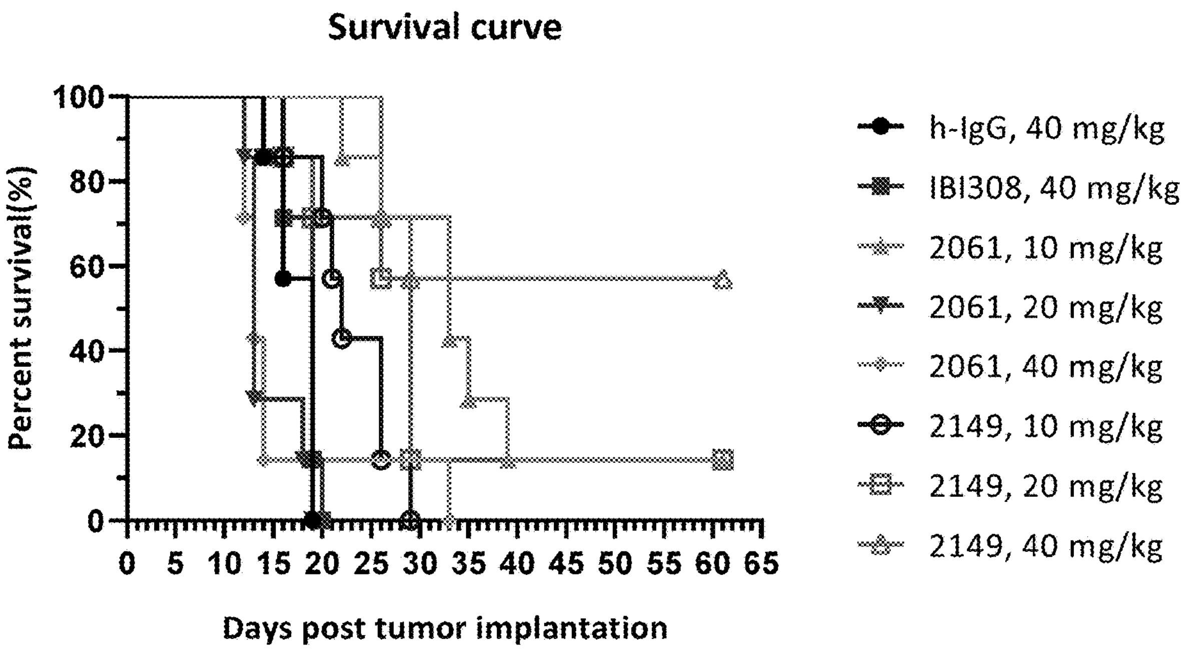
FIG. 14B shows the anti-tumor efficacy of 2061 and 2149 in the mouse B16F10 tumor, i.e., showing a survival curve.
Figure 14C:
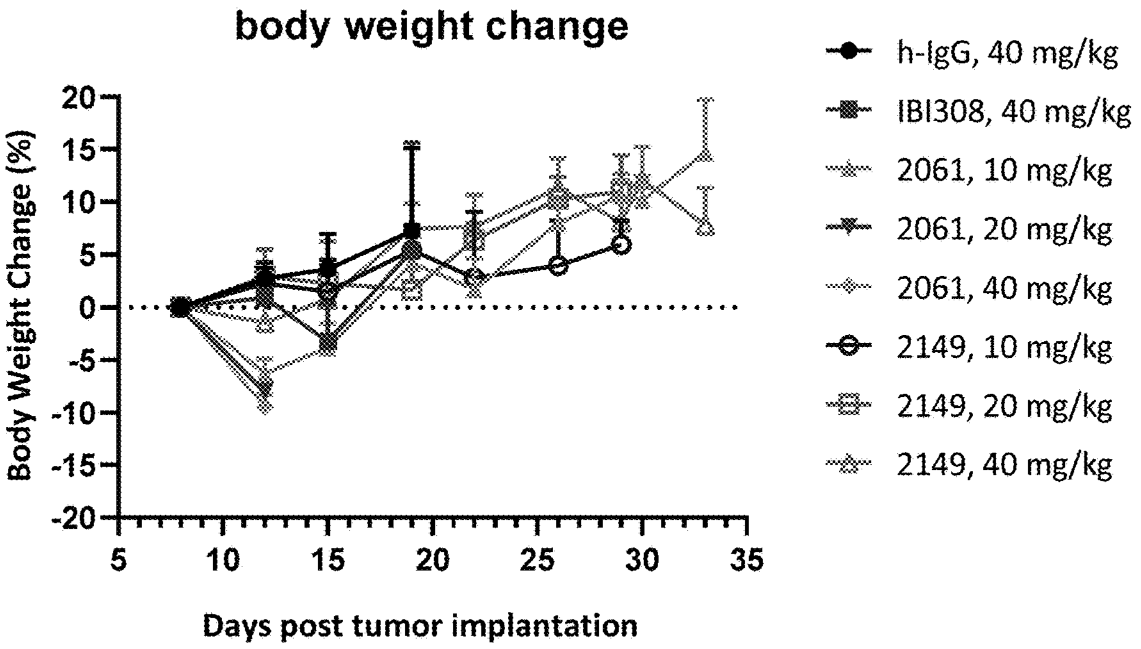
FIG. 14C shows the effect of 2061 and 2149 on mouse body weight.

Moreover, we performed statistical analysis of mouse survival (FIG. 14B), which shows that comparing 2061 and 2149 to the maximum dose/tolerated dose in this experiment, we could see that the mice survived more when administered 2149 at a dose of 40 mg/kg and the 2061 molecule at a dose of 10 mg/kg; in the 2149 group, the tumors were completely regressed in 3 out of 7 mice, and in the 2061 group, the tumor was completely regressed in only one mouse. Meanwhile, the results of the body weight measurement of mice (FIG. 14C) show that on day 29 after inoculation, there was no decrease in the body weight of the mice in each dose group of 2149, while there was a decrease in the body weight of the mice in the 2061 groups; the average body weight of the mice decreased by more than 5% in the low-dose (10 mg/kg) group; mouse deaths occurred in the medium-dose (20 mg/kg) and high-dose (40 mg/kg) group, and there were a total of 7 mice in each group, with 6 deaths. The details are shown in Table 12. 2149 was relatively safe, with no significant body weight decrease observed at the low, medium or high doses. There was only one mouse death each at the low and medium doses, and no deaths at the high dose. Moreover, it had a higher tumor complete response rate than that of 2061 (Table 16). Therefore, 2149 has better efficacy than that of 2061, is safer and has a higher therapeutic window.

TABLE 16

| Group | Tumor volume on day 19 ($mm^3$) | Death of mice on Day 19 | Tumor complete response rate on Day 33 |
|---|---|---|---|
| Anti-tumor efficacy statistics | | | |
| h-IgG | 1934.73 | 3/7 | 0/7 |
| IBI308, 40 mg/kg | 1540.91 | 2/7 | 0/7 |
| 2061, 10 mg/kg | 146.28 | 0/7 | 1/7 |
| 2061, 20 mg/kg | N/A | 6/7 | 0/7 |
| 2061, 40 mg/kg | N/A | 6/7 | 0/7 |
| 2149, 10 mg/kg | 450.77 | 1/7 | 0/7 |
| 2149, 20 mg/kg | 301.05 | 1/7 | 1/7 |
| 2149, 40 mg/kg | 114.50 | 0/7 | 3/7 |

To verify the efficacy of the αPD-1/IL2m immunoconjugate 2214 in vivo, hPD-1 knock-in mice were inoculated with MC38 cells (mouse colon cancer cell line, OBiO Technology (Shanghai) Co., Ltd.) to determine the anti-tumor efficacy of the bifunctional PD-1 antibody and IL-2 mutant molecule fusion protein (2214) of the present invention. SPF female hPD-1 knock-in mice (purchased from Shanghai Model Organisms Center, Inc.) with certificate No. 20170010010829 were used in the experiment. The MC38 cells were subcultured conventionally for subsequent in vivo study. The MC38 cells were collected by centrifugation and resuspended in PBS (1×) to form a cell suspension with a cell concentration of $5\times10^6$ cells/mL. On day 0, 0.2 mL of the cell suspension was subcutaneously inoculated into the right abdominal region of the hPD-1 knock-in mice to establish MC38 tumor-bearing mouse models.

Seven days after the tumor cell inoculation, the tumor volume in each mouse was measured. The mice were divided into groups of 7. The dosages and routes of administration are shown in Table 17.

TABLE 17

| Group | Dose of administration | Administration frequency | Route of administration |
|---|---|---|---|
| Groups, and dosages and routes of administration in the in vivo experiment | | | |
| h-IgG* | 40 mg/kg | QW x3 | Intraperitoneal injection |
| 2214 | 20 mg/kg | QW x3 | Intraperitoneal injection |
| 2214 | 40 mg/kg | QW x3 | Intraperitoneal injection |

*h-IgG was an isotype control antibody, purchased from Equitech-Bio, lot No. 161206-0656.

Figure 15A:
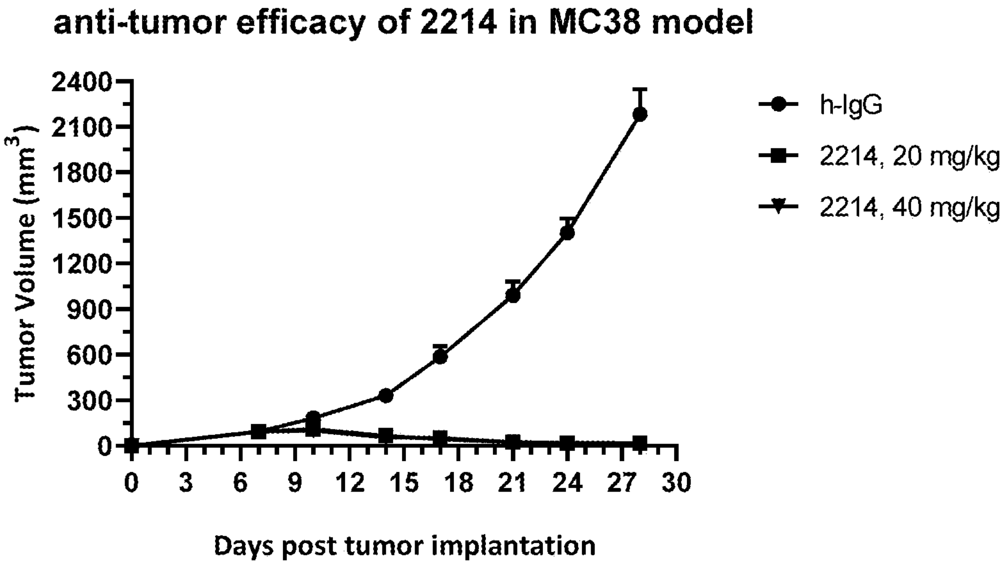
FIG. 15A shows the anti-tumor efficacy of 2214 in mice.
Figure 15B:
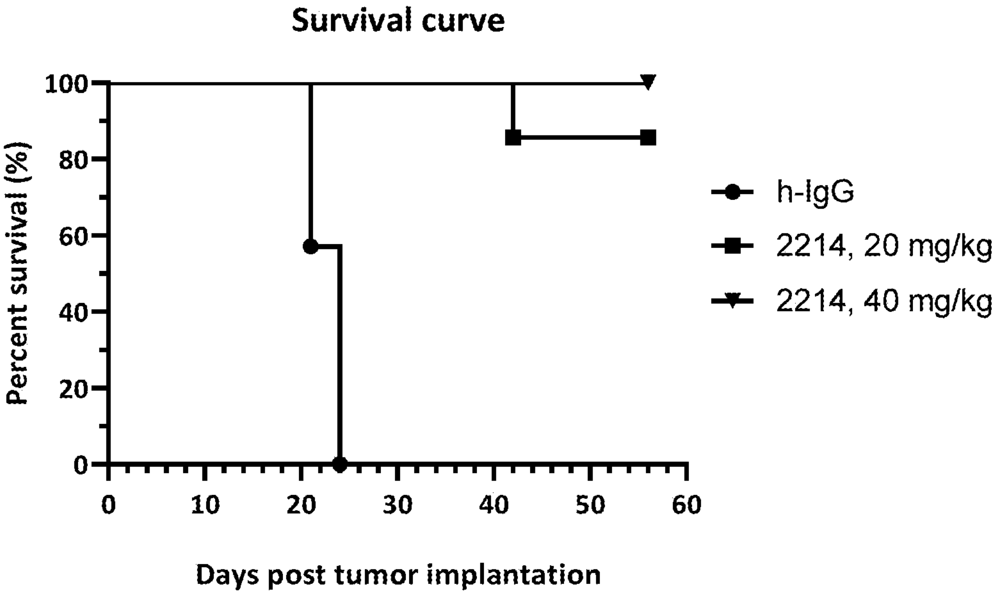
FIG. 15B shows the anti-tumor efficacy of 2214 in mice, i.e., showing a survival curve.

Both h-IgG and 2214 were used at a concentration of 4 mg/mL, and administered once every week, for a total of 3 doses (QW×3). Administration was performed on days 7, 14 and 21 after the inoculation of MC38 cells. The tumor volume and body weight of the mice were monitored twice a week for 56 days, as shown in FIG. 15A. Since the mice in the control group had a tumor volume of more than 2000 $mm^3$, we calculated the relative tumor growth inhibition (TGI %) by the following formula: TGI %=100%×(control group tumor volume−treatment group tumor volume)/(control group tumor volume−control group tumor volume before administration) on day 28 after inoculation. Tumor volume measurement: The maximum length of major axis (L) and maximum length of minor axis (W) of tumors were measured with a vernier caliper, and tumor volume was calculated using the following formula: $V=L\times W^2/2$. The mice were weighted using an electronic balance.

Figure 15C:
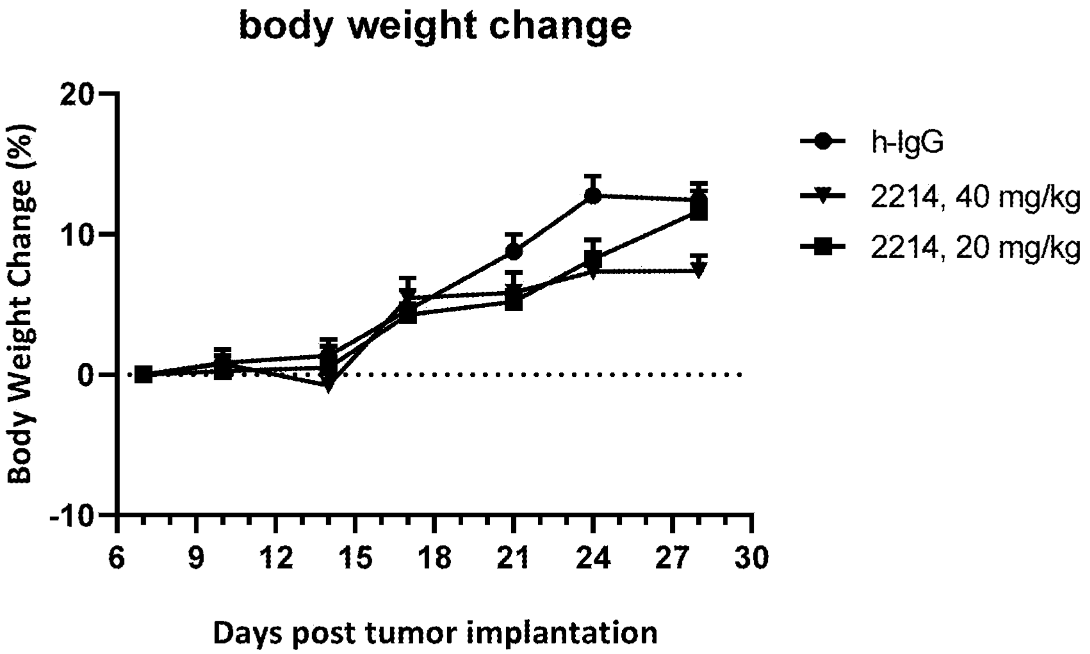
FIG. 15C shows the effect of 2214 on mouse body weight.

The tumor growth inhibition results are shown in Table 18: on day 28 after inoculation, 2214 had tumor growth inhibition of 104%, compared to the 20 mg/kg h-IgG group. Meanwhile, the results of the body weight measurement of mice (FIG. 15C) show that on day 28 after inoculation, there was no significant difference in the body weight of the mice.

TABLE 18

Anti-tumor efficacy statistics

| Group | Tumor volume ($mm^3$) | Tumor growth inhibition (%) @Day 28 | Tumor complete response @Day 56 |
|---|---|---|---|
| h-IgG | 2183.75 | N/A | 0/7 |
| 2214, 20 mg/kg | 17.60 | 104 | 6/7 |
| 2214, 40 mg/kg | 16.73 | 104 | 7/7 |

To demonstrate the efficacy of the αPD-1/IL2m immunoconjugate 2214 in vivo, hPD-1 knock-in mice were inoculated with PD-1 antibody-resistant B16F10 cells (mouse melanoma cell line, ATCC, CRL-6475) to determine the anti-tumor efficacy of the bifunctional PD-1 antibody and IL-2 mutant molecule fusion protein (2214) of the present invention. SPF female hPD-1 knock-in mice (purchased from Shanghai Model Organisms Center, Inc.) with certificate No. 20170010010829 were used in the experiment.

The B16F10 cells were subcultured conventionally for subsequent in vivo study. The B16F10 cells were collected by centrifugation and resuspended in PBS (1×) to form a cell suspension with a cell concentration of $2.5\times10^6$ cells/mL. On day 0, 0.2 mL of the cell suspension was subcutaneously inoculated into the right abdominal region of the hPD-1 knock-in mice to establish B16F10 tumor-bearing mouse models.

Seven days after the tumor cell inoculation, the tumor volume in each mouse was measured. The mice were divided into groups of 7. The dosages and routes of administration are shown in Table 19.

TABLE 19

Groups, and dosages and routes of administration in the in vivo experiment

| Group | Dose of administration | Administration frequency | Route of administration |
|---|---|---|---|
| h-IgG* | 40 mg/kg | QW x3 | Intraperitoneal injection |
| 2214, 20 mg/kg | 20 mg/kg | QW x3 | Intraperitoneal injection |
| 2214, 40 mg/kg | 40 mg/kg | QW x3 | Intraperitoneal injection |

Figure 16A:
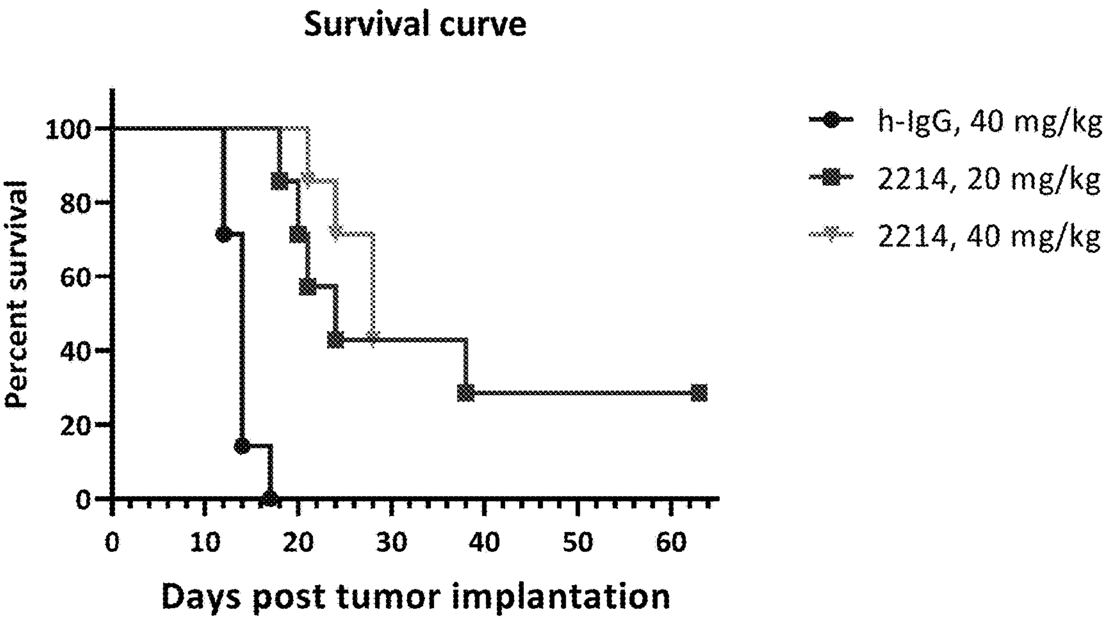
FIG. 16A shows the anti-tumor efficacy of 2214 in the mouse B16F10 tumor, i.e., showing a survival curve.
Figure 16B:
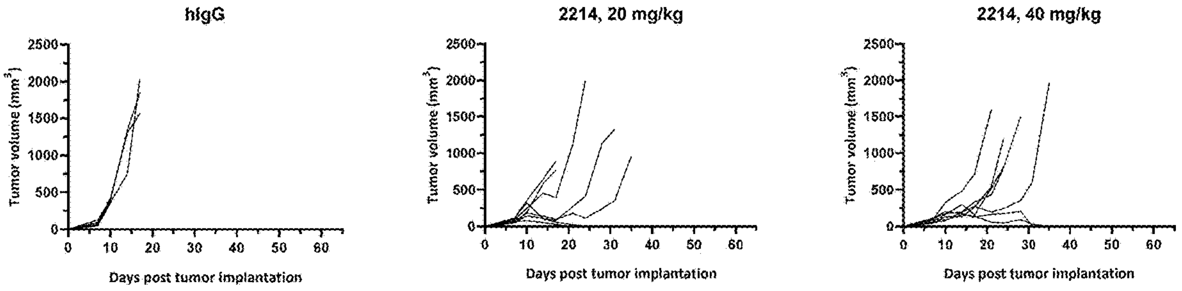
FIG. 16B shows the anti-tumor efficacy of 2214 in the mouse B16F10 tumor, i.e., showing a survival curve.

*h-IgG was an isotype control antibody, purchased from Equitech-Bio, lot No. 161206-0656.

h-IgG, 20 mg/kg 2214 and 40 mg/kg 2214 were used at concentrations of 4 mg/mL, 2 mg/mL and 4 mg/mL, respectively, and administered once every week, for a total of 3 doses (QW×3). Administration was performed on days 7, 14 and 21 after the inoculation of B16F10 cells. The tumor volume and body weight of the mice were monitored twice a week for 63 days, as shown in FIGS. 16A-16B. Tumor volume measurement: The maximum length of major axis (L) and maximum length of minor axis (W) of tumors were measured with a vernier caliper, and tumor volume was calculated using the following formula: $V=L\times W^2/2$. The mice were weighted using an electronic balance. Mice with tumor volumes of more than 2000 $mm^3$ were euthanized.

Figure 16C:
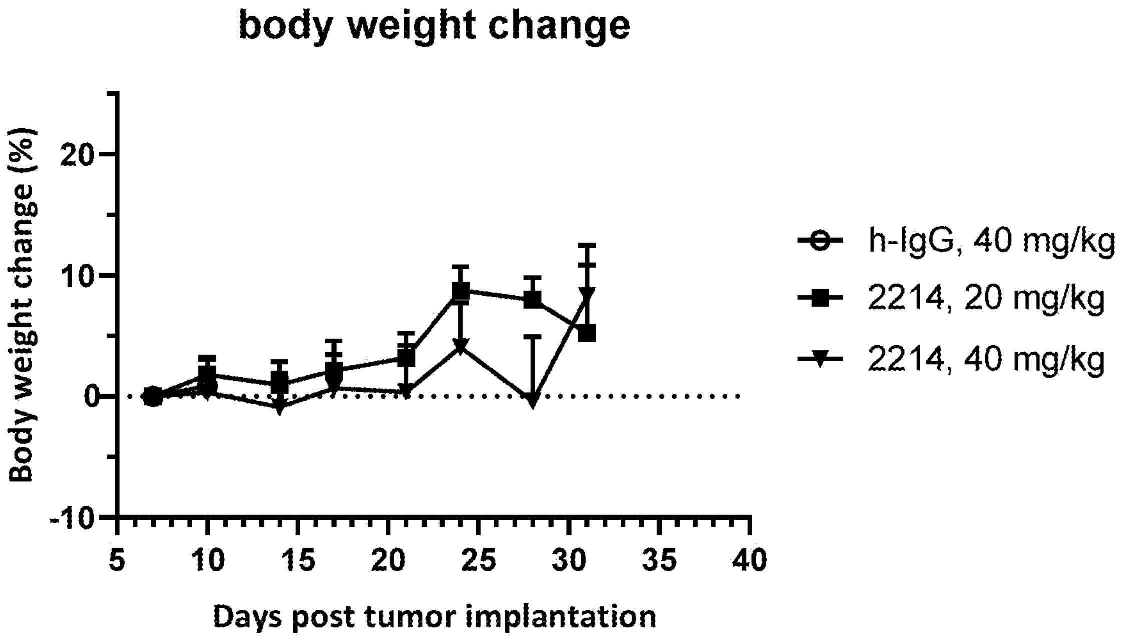
FIG. 16C shows the effect of 2214 on mouse body weight.

The survival curve of the mice in FIG. 16A shows that 2214 at both doses could significantly extend the survival of the mice. Meanwhile, the results of the body weight measurement of mice (FIG. 16C) show that on day 22 after inoculation, there was no significant difference in the body weight of the mice.

| SEQ ID NO | Description | Sequence |
|---|---|---|
| 1 | Full-length native IL-2 | MYRMQLLSCIALSLALVTNSAPTSSSTKKTQLQLEHLLLDLQMI LNGINNYKNPKLTRMLTFKFYMPKKATELKHLQCLEEELKPLE EVLNLAQSKNFHLRPRDLISNINVIVLELKGSETTFMCEYADETA TIVEFLNRWITFCQSIISTLT |
| 2 | Mature IL-2 | APTSSSTKKTQLQLEHLLLDLQMILNGINNYKNPKLTRMLTFKF YMPKKATELKHLQCLEEELKPLEEVLNLAQSKNFHLRPRDLISN INVIVLELKGSETTFMCEYADETATIVEFLNRWITFCQSIISTLT |
| 3 | Wild-type IL-2 (comprising C125S) | APTSSSTKKTQLQLEHLLLDLQMILNGINNYKNPKLTRMLTFKF YMPKKATELKHLQCLEEELKPLEEVLNLAQSKNFHLRPRDLISN INVIVLELKGSETTFMCEYADETATIVEFLNRWITFSQSIISTLT |
| Molecule 2063 | Having T3A + N88D mutations, and a replacement with an IL15 B′C′ loop region | |
| 4 | IL-2 mutant protein | APASSSTKKTQLQLEHLLLDLQMILNGINNYKNPKLTRMLTFKFYMPKKA TELKHLQCLEEELKPLEEVLNLAGDASIHDLISDINVIVLELKGSETTFMCE YADETATIVEFLNRWITFSQSIISTLT |
| 5 | Linker | GGGGSGGGGS |
| 6 | Fc-knob | DKTHTCPPCPAPEAAGGPSVFLFPPKPKDTLMISRTPEVTCVVVDVSHEDP EVKFNWYVDGVEVHNAKTKPREEQYNSTYRVVSVLTVLHQDWLNGKE |

-continued

| SEQ ID NO | Description | Sequence |
|---|---|---|
| | | YKCKVSNKALPAPIEKTISKAKGQPREPQVYTLPPCRDELTKNQVSLWCL VKGFYPSDIAVEWESNGQPENNYKTTPPVLDSDGSFFLYSKLTVDKSRWQ QGNVFSCSVMHEALHNHYTQKSLSLSPGK |
| 7 | IL-2m-linker-Fc-knob | APASSSTKKTQLQLEHLLLDLQMILNGINNYKNPKLTRMLTFKFYMPKKA TELKHLQCLEEELKPLEEVLNLAGDASIHDLISDINVIVLELKGSETTFMCE YADETATIVEFLNRWITFSQSIISTLTGGGGSGGGGSDKTHTCPPCPAPEAA GGPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPIE KTISKAKGQPREPQVYTLPPCRDELTKNQVSLWCLVKGFYPSDIAVEWES NGQPENNYKTTPPVLDSDGSFFLYSKLTVDKSRWQQGNVFSCSVMHEAL HNHYTQKSLSLSPGK |
| 8 | Anti-PD-1 heavy chain variable region | QVQLVQSGAEVKKPGSSVKVSCKASGGTFSSYAISWVRQAPGQGLEWM GLIIPMFDTAGYAQKFQGRVAITVDESTSTAYMELSSLRSEDTAVYYCARA EHSSTGTFDYWGQGTLVTVSS |
| 9 | Anti-PD-1 heavy chain variable region CDR1 | GGTFSSYAIS |
| 10 | Anti-PD-1 heavy chain variable region CDR2 | LIIPMFDTAGYAQKFQG |
| 11 | Anti-PD-1 heavy chain variable region CDR3 | AEHSSTGTFDY |
| 12 | Fc-hole | DKTHTCPPCPAPEAAGGPSVFLFPPKPKDTLMISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVCTLPPSRDELTKNQVSLSCAV KGFYPSDIAVEWESNGQPENNYKTTPPVLDSDGSFFLVSKLTVDKSRWQQ GNVFSCSVMHEALHNHYTQKSLSLSPGK |
| 13 | Anti-PD-1 heavy chain constant region | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEPK SCDKTHTCPPCPAPEAAGGPSVFLFPPKPKDTLMISRTPEVTCVVVDVSHE DPEVKFNWYVDGVEVHNAKTKPREEQYNSTYRVVSVLTVLHQDWLNG KEYKCKVSNKALPAPIEKTISKAKGQPREPQVCTLPPSRDELTKNQVSLSC AVKGFYPSDIAVEWESNGQPENNYKTTPPVLDSDGSFFLVSKLTVDKSRW QQGNVFSCSVMHEALHNHYTQKSLSLSPGK |
| 14 | Anti-PD-1 heavy chain | QVQLVQSGAEVKKPGSSVKVSCKASGGTFSSYAISWVRQAPGQGLEWM GLIIPMFDTAGYAQKFQGRVAITVDESTSTAYMELSSLRSEDTAVYYCARA EHSSTGTFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQT YICNVNHKPSNTKVDKKVEPKSCDKTHTCPPCPAPEAAGGPSVFLFPPKP KDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPR EPQVCTLPPSRDELTKNQVSLSCAVKGFYPSDIAVEWESNGQPENNYKTT PPVLDSDGSFFLVSKLTVDKSRWQQGNVFSCSVMHEALHNHYTQKSLSL SPGK |
| 15 | Anti-PD-1 light chain variable region | DIQMTQSPSSVSASVGDRVTITCRASQGISSWLAWYQQKPGKAPKLLISA ASSLQSGVPSRFSGSGSGTDFTLTISSLQPEDFATYYCQQANHLPFTFGGGT KVEIK |
| 16 | Anti-PD-1 light chain variable region CDR1 | RASQGISSWLA |
| 17 | Anti-PD-1 light chain variable region CDR2 | AASSLQS |

-continued

| SEQ ID NO | Description | Sequence |
|---|---|---|
| 18 | Anti-PD-1 light chain variable region CDR3 | QQANHLPFT |
| 19 | Anti-PD-1 light chain constant region | RTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTK<br>SFNRGEC |
| 20 | Anti-PD-1 light chain | DIQMTQSPSSVSASVGDRVTITCRASQGISSWLAWYQQKPGKAPKLLISA<br>ASSLQSGVPSRFSGSGSGTDFTLTISSLQPEDFATYYCQQANHLPFTFGGGT<br>KVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLS<br>SPVTKSFNRGEC |
| 21 | Heavy chain constant region (without knob-hole) | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEPK<br>SCDKTHTCPPCPAPE**AA**GGPSVFLFPPKPKDTLMISRTPEVTCVVVDVSHE<br>DPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDKSRW<br>QQGNVFSCSVMHEALHNHYTQKSLSLSPGK (having LALA mutations<br>(L234A & L235A) to reduce ADCC effect of IgG1 Fc) |
| 22 | Heavy chain (without hole mutations) | QVQLVQSGAEVKKPGSSVKVSCKASGGTFSSYAISWVRQAPGQGLEWM<br>GLIIPMFDTAGYAQKFQGRVAITVDESTSTAYMELSSLRSEDTAVYYCARA<br>EHSSTGTFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQT<br>YICNVNHKPSNTKVDKKVEPKSCDKTHTCPPCPAPE**AA**GGPSVFLFPPKP<br>KDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTP<br>PVLDSDGSFFLYSKLTVDKSRWQQGNVFSCSVMHEALHNHYTQKSLSLS<br>PGK (having LALA mutations (L234A & L235A) to reduce<br>ADCC effect of IgG1 Fc) |
| Molecule 2132 | | Having T3A + N88R mutations, and a replacement with an IL15 B'C' loop region<br>Heavy and light chains in the anti-PD-1 antibody moiety are the same as those of the molecule 2063 |
| 23 | IL-2 mutant protein | APASSSTKKTQLQLEHLLLDLQMILNGINNYKNPKLTRMLTFKFYMPKKA<br>TELKHLQCLEEELKPLEEVLNLAGDASIHDLISRINVIVLELKGSETTFMCE<br>YADETATIVEFLNRWITFSQSIISTLT |
| 5 | Linker | GGGGSGGGGS |
| 6 | Fc-knob | DKTHTCPPCPAPEAAGGPSVFLFPPKPKDTLMISRTPEVTCVVVDVSHEDP<br>EVKFNWYVDGVEVHNAKTKPREEQYNSTYRVVSVLTVLHQDWLNGKE<br>YKCKVSNKALPAPIEKTISKAKGQPREPQVYTLPPCRDELTKNQVSLWCL<br>VKGFYPSDIAVEWESNGQPENNYKTTPPVLDSDGSFFLYSKLTVDKSRWQ<br>QGNVFSCSVMHEALHNHYTQKSLSLSPGK |
| 24 | IL-2m-linker-Fc-knob | APASSSTKKTQLQLEHLLLDLQMILNGINNYKNPKLTRMLTFKFYMPKKA<br>TELKHLQCLEEELKPLEEVLNLAGDASIHDLISRINVIVLELKGSETTFMCE<br>YADETATIVEFLNRWITFSQSIISTLTGGGGSGGGGSDKTHTCPPCPAPEAA<br>GGPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPAPIE<br>KTISKAKGQPREPQVYTLPPCRDELTKNQVSLWCLVKGFYPSDIAVEWES<br>NGQPENNYKTTPPVLDSDGSFFLYSKLTVDKSRWQQGNVFSCSVMHEAL<br>HNHYTQKSLSLSPGK |
| Molecule 2149 | | Having T3A + N88R + S130R mutations, and a replacement with an IL15 B'C' loop region<br>Heavy and light chains in the anti-PD-1 antibody moiety are the same as those of the molecule 2063 |
| 25 | IL-2 mutant protein | APASSSTKKTQLQLEHLLLDLQMILNGINNYKNPKLTRMLTFKFYMPKKA<br>TELKHLQCLEEELKPLEEVLNLAGDASIHDLISRINVIVLELKGSETTFMCE<br>YADETATIVEFLNRWITFSQSIIRTLT |
| 5 | Linker | GGGGSGGGGS |

-continued

| SEQ ID NO | Description | Sequence |
|---|---|---|
| 6 | Fc-knob | DKTHTCPPCPAPEAAGGPSVFLFPPKPKDTLMISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVYTLPPCRDELTKNQVSLWCL VKGFYPSDIAVEWESNGQPENNYKTTPPVLDSDGSFFLYSKLTVDKSRWQ QGNVFSCSVMHEALHNHYTQKSLSLSPGK |
| 26 | IL-2m-linker-Fc-knob | APASSSTKKTQLQLEHLLLDLQMILNGINNYKNPKLTRMLTFKFYMPKKA TELKHLQCLEEELKPLEEVLNLAGDASIHDLISRINVIVLELKGSETTFMCE YADETATIVEFLNRWITFSQSIIRTLTGGGGSGGGGSDKTHTCPPCPAPEAA GGPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPIE KTISKAKGQPREPQVYTLPPCRDELTKNQVSLWCLVKGFYPSDIAVEWES NGQPENNYKTTPPVLDSDGSFFLYSKLTVDKSRWQQGNVFSCSVMHEAL HNHYTQKSLSLSPGK |
| | | Having T3A + F42A + N88R + S127E mutations, and a truncation of a B′C′ loop region |
| Molecule 2213 | | Heavy and light chains in the anti-PD-1 antibody moiety are the same as those of the molecule 2063 |
| 27 | IL-2 mutant protein | APASSSTKKTQLQLEHLLLDLQMILNGINNYKNPKLTRMLTAKFYMPKKA TELKHLQCLEEELKPLEEVLNLAQSKNFHDLISRINVIVLELKGSETTFMC EYADETATIVEFLNRWITFSQEIISTLT |
| 5 | Linker | GGGGSGGGGS |
| 6 | Fc-knob | DKTHTCPPCPAPEAAGGPSVFLFPPKPKDTLMISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVYTLPPCRDELTKNQVSLWCL VKGFYPSDIAVEWESNGQPENNYKTTPPVLDSDGSFFLYSKLTVDKSRWQ QGNVFSCSVMHEALHNHYTQKSLSLSPGK |
| 28 | IL-2m-linker-Fc-knob | APASSSTKKTQLQLEHLLLDLQMILNGINNYKNPKLTRMLTAKFYMPKKA TELKHLQCLEEELKPLEEVLNLAQSKNFHDLISRINVIVLELKGSETTFMC EYADETATIVEFLNRWITFSQEIISTLTGGGGSGGGGSDKTHTCPPCPAPEA AGGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPI EKTISKAKGQPREPQVYTLPPCRDELTKNQVSLWCLVKGFYPSDIAVEWE SNGQPENNYKTTPPVLDSDGSFFLYSKLTVDKSRWQQGNVFSCSVMHEA LHNHYTQKSLSLSPGK |
| | | Having T3A + F42A + N88R + S127E mutations, and a replacement with an IL15 B′C′ loop region |
| Molecule 2214 | | Heavy and light chains in the anti-PD-1 antibody moiety are the same as those of the molecule 2063 |
| 29 | IL-2 mutant protein | APASSSTKKTQLQLEHLLLDLQMILNGINNYKNPKLTRMLTAKFYMPKKA TELKHLQCLEEELKPLEEVLNLAGDASIHDLISRINVIVLELKGSETTFMCE YADETATIVEFLNRWITFSQEIISTLT |
| 5 | Linker | GGGGSGGGGS |
| 6 | Fc-knob | DKTHTCPPCPAPEAAGGPSVFLFPPKPKDTLMISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVYTLPPCRDELTKNQVSLWCL VKGFYPSDIAVEWESNGQPENNYKTTPPVLDSDGSFFLYSKLTVDKSRWQ QGNVFSCSVMHEALHNHYTQKSLSLSPGK |
| 30 | IL-2m-linker-Fc-knob | APASSSTKKTQLQLEHLLLDLQMILNGINNYKNPKLTRMLTAKFYMPKKA TELKHLQCLEEELKPLEEVLNLAGDASIHDLISRINVIVLELKGSETTFMCE YADETATIVEFLNRWITFSQEIISTLTGGGGSGGGGSDKTHTCPPCPAPEAA GGPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPIE KTISKAKGQPREPQVYTLPPCRDELTKNQVSLWCLVKGFYPSDIAVEWES NGQPENNYKTTPPVLDSDGSFFLYSKLTVDKSRWQQGNVFSCSVMHEAL HNHYTQKSLSLSPGK |
| | | Having T3A + K35E + N88R + S127E mutations, and a truncation of a B′C′ loop region |
| Molecule 2219 | | Heavy and light chains in the anti-PD-1 antibody moiety are the same as those of the molecule 2063 |
| 31 | IL-2 mutant protein | APASSSTKKTQLQLEHLLLDLQMILNGINNYKNPELTRMLTFKFYMPKKA TELKHLQCLEEELKPLEEVLNLAQSKNFHDLISRINVIVLELKGSETTFMC EYADETATIVEFLNRWITFSQEIISTLT |

-continued

Figure 1B:
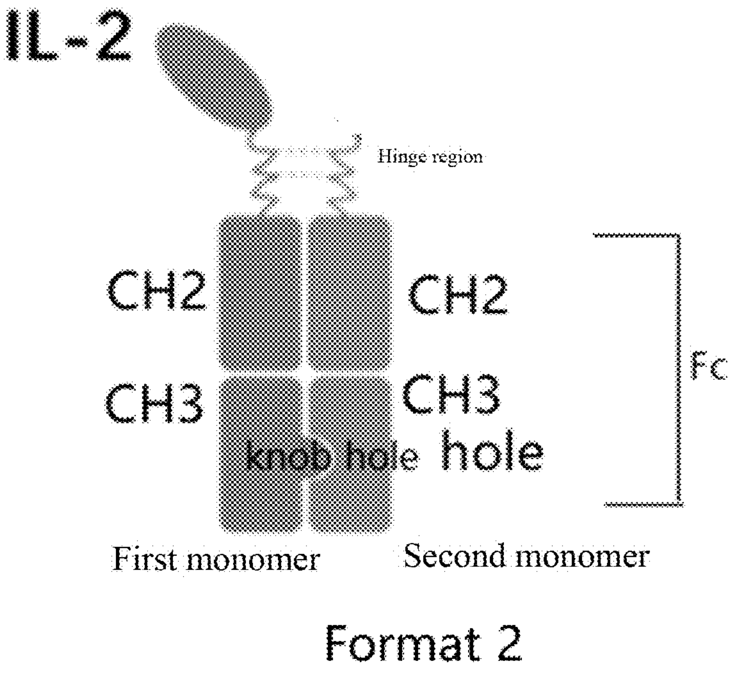
FIG. 1B shows the molecular structure of an IL-2-Fc fusion protein of molecules 2124 and 3010.

| SEQ ID NO | Description | Sequence |
|---|---|---|
| 5 | Linker | GGGGSGGGGS |
| 6 | Fc-knob | DKTHTCPPCPAPEAAGGPSVFLFPPKPKDTLMISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVYTLPPCRDELTKNQVSLWCL VKGFYPSDIAVEWESNGQPENNYKTTPPVLDSDGSFFLYSKLTVDKSRWQ QGNVFSCSVMHEALHNHYTQKSLSLSPGK |
| 32 | IL-2m-linker-Fc-knob | APASSSTKKTQLQLEHLLLDLQMILNGINNYKNPELTRMLTFKFYMPKKA TELKHLQCLEEELKPLEEVLNLAQSKNFHDLISRINVIVLELKGSETTFMC EYADETATIVEFLNRWITFSQEIISTLTGGGGSGGGGSDKTHTCPPCPAPEA AGGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPI EKTISKAKGQPREPQVYTLPPCRDELTKNQVSLWCLVKGFYPSDIAVEWE SNGQPENNYKTTPPVLDSDGSFFLYSKLTVDKSRWQQGNVFSCSVMHEA LHNHYTQKSLSLSPGK |
| | | FIG. 1B Format 2 |
| Molecule 2124 | | First monomer: IL-2 protein-linker-Fc (Knob) Second monomer: hinge region-Fc (hole) |
| 4 | IL-2 protein | APASSSTKKTQLQLEHLLLDLQMILNGINNYKNPKLTRMLTFKFYMPKKA TELKHLQCLEEELKPLEEVLNLAGDASIHDLISDINVIVLELKGSETTFMCE YADETATIVEFLNRWITFSQSIISTLT |
| 5 | Linker | GGGGSGGGGS |
| 6 | Fc-Knob | DKTHTCPPCPAPEAAGGPSVFLFPPKPKDTLMISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVYTLPPCRDELTKNQVSLWCL VKGFYPSDIAVEWESNGQPENNYKTTPPVLDSDGSFFLYSKLTVDKSRWQ QGNVFSCSVMHEALHNHYTQKSLSLSPGK |
| 7 | IL-2m-linker-Fc-knob | APASSSTKKTQLQLEHLLLDLQMILNGINNYKNPKLTRMLTFKFYMPKKA TELKHLQCLEEELKPLEEVLNLAGDASIHDLISDINVIVLELKGSETTFMCE YADETATIVEFLNRWITFSQSIISTLTGGGGSGGGGSDKTHTCPPCPAPEAA GGPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPIE KTISKAKGQPREPQVYTLPPCRDELTKNQVSLWCLVKGFYPSDIAVEWES NGQPENNYKTTPPVLDSDGSFFLYSKLTVDKSRWQQGNVFSCSVMHEAL HNHYTQKSLSLSPGK |
| 35 | Hinge region | EPKAS |
| 12 | Fc-hole | DKTHTCPPCPAPEAAGGPSVFLFPPKPKDTLMISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVCTLPPSRDELTKNQVSLSCAV KGFYPSDIAVEWESNGQPENNYKTTPPVLDSDGSFFLVSKLTVDKSRWQQ GNVFSCSVMHEALHNHYTQKSLSLSPGK |
| 36 | Hinge region-Fc-hole | EPKASDKTHTCPPCPAPEAAGGPSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVCTLPPSRDELTKNQVSL SCAVKGFYPSDIAVEWESNGQPENNYKTTPPVLDSDGSFFLVSKLTVDKSR WQQGNVFSCSVMHEALHNHYTQKSLSLSPGK |
| | | FIG. 1B Format 2 |
| Molecule 3010 | | First monomer: IL-2 protein-linker-Fc (Knob) Second monomer: Hinge-Fc (hole) |
| 3 | IL-2 protein | APTSSSTKKTQLQLEHLLLDLQMILNGINNYKNPKLTRMLTFKFYMPKKA TELKHLQCLEEELKPLEEVLNLAQSKNFHLRPRDLISNINVIVLELKGSETT FMCEYADETATIVEFLNRWITFSQSIISTLT |
| 5 | Linker | GGGGSGGGGS |
| 6 | Fc-Knob | DKTHTCPPCPAPEAAGGPSVFLFPPKPKDTLMISRTPEVTCVVVDVSHEDP EVKFNWYVDGVEVHNAKTKPREEQYNSTYRVVSVLTVLHQDWLNGKE YKCKVSNKALPAPIEKTISKAKGQPREPQVYTLPPCRDELTKNQVSLWCL VKGFYPSDIAVEWESNGQPENNYKTTPPVLDSDGSFFLYSKLTVDKSRWQ QGNVFSCSVMHEALHNHYTQKSLSLSPGK |

-continued

| SEQ ID NO | Description | Sequence |
|---|---|---|
| 37 | IL-2 protein-linker-Fc-knob | APTSSSTKKTQLQLEHLLLDLQMILNGINNYKNPKLTRMLTFKFYMPKKA<br>TELKHLQCLEEELKPLEEVLNLAQSKNFHLRPRDLISNINVIVLELKGSETT<br>FMCEYADETATIVEFLNRWITFSQSIISTLTGGGGSGGGGSDKTHTCPPCPA<br>PEAAGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALP<br>APIEKTISKAKGQPREPQVYTLPPCRDELTKNQVSLWCLVKGFYPSDIAVE<br>WESNGQPENNYKTTPPVLDSDGSFFLYSKLTVDKSRWQQGNVFSCSVMH<br>EALHNHYTQKSLSLSPGK |
| 35 | Hinge region | EPKAS |
| 12 | Fc-hole | DKTHTCPPCPAPEAAGGPSVFLFPPKPKDTLMISRTPEVTCVVVDVSHEDP<br>EVKFNWYVDGVEVHNAKTKPREEQYNSTYRVVSVLTVLHQDWLNGKE<br>YKCKVSNKALPAPIEKTISKAKGQPREPQVCTLPPSRDELTKNQVSLSCAV<br>KGFYPSDIAVEWESNGQPENNYKTTPPVLDSDGSFFLVSKLTVDKSRWQQ<br>GNVFSCSVMHEALHNHYTQKSLSLSPGK |
| 36 | Hing-Fc-hole | EPKASDKTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQDWL<br>NGKEYKCKVSNKALPAPIEKTISKAKGQPREPQVCTLPPSRDELTKNQVSL<br>SCAVKGFYPSDIAVEWESNGQPENNYKTTPPVLDSDGSFFLVSKLTVDKSR<br>WQQGNVFSCSVMHEALHNHYTQKSLSLSPGK |
| Other sequences | | |
| 37 | IL-2Rβ-Fc-Knob | AVNGTSQFTCFYNSRANISCVWSQDGALQDTSCQVHAWPDRRRWNQTC<br>ELLPVSQASWACNLILGAPDSQKLTTVDIVTLRVLCREGVRWRVMAIQDF<br>KPFENLRLMAPISLQVVHVETHRCNISWEISQASHYFERHLEFEARTLSPG<br>HTWEEAPLLTLKQKQEWICLETLTPDTQYEFQVRVKPLQGEFTTWSPWSQ<br>PLAFRTKPAALGKDTGLNDIFEAQKIEWHEDKTHTCPPCPAPEAAGGPSV<br>FLFPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTISKA<br>KGQPREPQVYTLPPCRDELTKNQVSLWCLVKGFYPSDIAVEWESNGQPEN<br>NYKTTPPVLDSDGSFFLYSKLTVDKSRWQQGNVFSCSVMHEALHNHYTQ<br>KSLSLSPGK |
| 38 | IL-2Rγ-Fc-Hole | LNTTILTPNGNEDTTADFFLTTMPTDSLSVSTLPLPEVQCFVFNVEYMNCT<br>WNSSSEPQPTNLTLHYWYKNSDNDKVQKCSHYLFSEEITSGCQLQKKEIH<br>LYQTFVVQLQDPREPRRQATQMLKLQNLVIPWAPENLTLHKLSESQLELN<br>WNNRFLNHCLEHLVQYRTDWDHSWTEQSVDYRHKFSLPSVDGQKRYTF<br>RVRSRFNPLCGSAQHWSEWSHPIHWGSNTSKENGLNDIFEAQKIEWHEH<br>HHHHHHDKTHTCPPCPAPEAAGGPSVFLFPPKPKDTLMISRTPEVTCVVV<br>DVSHEDPEVKFNWYVDGVEVHNAKTKPREEQYNSTYRVVSVLTVLHQD<br>WLNGKEYKCKVSNKALPAPIEKTISKAKGQPREPQVCTLPPSRDELTKNQ<br>VSLSCAVKGFYPSDIAVEWESNGQPENNYKTTPPVLDSDGSFFLVSKLTVD<br>KSRWQQGNVFSCSVMHEALHNRYTQKSLSLSPGK |
| 39 | IL-15 B′C′ loop region | AGDASIH |
| 40 | IL-2 B′C′ loop region | AQSKNFHLRPR |
| 41 | Truncated IL-2 B′C′ loop region | AQSKNFH<br>Deletion of the last 4 amino acids (LRPR) |
| 42 | Fc (without Knob-hole mutation, with LALA mutations) | DKTHTCPPCPAPE**AA**GGPSVFLFPPKPKDTLMISRTPEVTCVVVDVSHEDP<br>EVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQ<br>GNVFSCSVMHEALHNHYTQKSLSLSPGK |
| 43 | Fc (without Knob-hole mutation, without LALA mutations) | DKTHTCPPCPAPE**LL**GGPSVFLFPPKPKDTLMISRTPEVTCVVVDVSHEDP<br>EVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQ<br>GNVFSCSVMHEALHNHYTQKSLSLSPGK |
| Molecule | | |
| 2061 | Control molecule of this study, derived from US20180326010A1 | |
| 33 | Heavy chain knob | EVQLLESGGGLVQPGGSLRLSCAASGFSFSSYTMSWVRQAPGKGLEWVA<br>TISGGGRDIYYPDSVKGRFTISRDNSKNTLYLQMNSLRAEDTAVYYCVLLT<br>GRVYFALDSWGQGTLVTVSSASTKGPSVFPLAPSSKSTSGGTAALGCLVK<br>DYFPEPVTVSWNSGALTSGVHTFPAVLQSSGLYSLSSVVTVPSSSLGTQTY |

-continued

| SEQ ID NO | Description | Sequence |
|---|---|---|
| | | ICNVNHKPSNTKVDKKVEPKSCDKTHTCPPCPAPEAAGGPSVFLFPPKPK DTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPCRDELTKNQVSLWCLVKGFYPSDIAVEWESNGQPENNYKTTPP VLDSDGSFFLYSKLTVDKSRWQQGNVFSCSVMHEALHNHYTQKSLSLSP GGGGGSGGGGSGGGGSAPASSSTKKTQLQLEHLLLDLQMILNGINNYKN PKLTRMLTAKFAMPKKATELKHLQCLEEELKPLEEVLNGAQSKNFHLRPR DLISNINVIVLELKGSETTFMCEYADETATIVEFLNRWITFAQSIISTLT |
| 45 | Heavy chain hole | EVQLLESGGGLVQPGGSLRLSCAASGFSFSSYTMSWVRQAPGKGLEWVA TISGGGRDIYYPDSVKGRFTISRDNSKNTLYLQMNSLRAEDTAVYYCVLLT GRVYFALDSWGQGTLVTVSSASTKGPSVFPLAPSSKSTSGGTAALGCLVK DYFPEPVTVSWNSGALTSGVHTFPAVLQSSGLYSLSSVVTVPSSSLGTQTY ICNVNHKPSNTKVDKKVEPKSCDKTHTCPPCPAPEAAGGPSVFLFPPKPK DTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVCTLPPSRDELTKNQVSLSCAVKGFYPSDIAVEWESNGQPENNYKTTPP VLDSDGSFFLVSKLTVDKSRWQQGNVFSCSVMHEALHNHYTQKSLSLSP GK |
| 34 | Light chain LC | DIVMTQSPDSLAVSLGERATINCKASESVDTSDNSFIHWYQQKPGQSPKLL IYRSSTLESGVPDRFSGSGSGTDFTLTISSLQAEDVAVYYCQQNYDVPWTF GQGTKVEIKRTVAAPSVFIFPPSDEQLKSGTASVVCLLNNFYPREAKVQW KVDNALQSGNSQESVTEQDSKDSTYSLSSTLTLSKADYEKHKVYACEVT HQGLSSPVTKSFNRGEC |

The invention claimed is:

1. An immunoconjugate, comprising (i) an anti-PD-1 antibody or antigen-binding fragment thereof and (ii) an IL-2 mutant protein, wherein the anti-PD-1 antibody or the antigen-binding fragment thereof comprises a heavy chain comprising a heavy chain variable region, wherein the heavy chain variable region comprises HCDR1, HCDR2 and HCDR3 set forth in amino acid sequences of SEQ ID NOs: 9, 10 and 11, respectively, and a light chain comprising a light chain variable region, wherein the light chain variable region comprises LCDR1, LCDR2 and LCDR3 set forth in amino acid sequences of SEQ ID NOs: 16, 17 and 18, respectively; and the IL-2 mutant protein comprises the amino acid sequence set forth in SEQ ID NO: 23 or the amino acid sequence set forth in SEQ ID NO: 25.

2. The immunoconjugate of claim 1, wherein the IL-2 mutant protein comprises the amino acid sequence set forth in SEQ ID NO: 23.

3. The immunoconjugate of claim 1, wherein the IL-2 mutant protein comprises the amino acid sequence set forth in SEQ ID NO: 25.

4. The immunoconjugate of claim 1, wherein the IL-2 mutant protein is fused directly or via a linker to an Fc fragment.

5. The immunoconjugate of claim 4, wherein the IL-2 mutant protein is fused to the Fc fragment via a linker comprising the amino acid sequence of GGGGSGGGGS (SEQ ID NO: 5).

6. The immunoconjugate of claim 4, wherein the IL-2 mutant protein comprises an N-terminus and a C-terminus, the Fc fragment comprises an N-terminus and a C-terminus, and wherein the C-terminus of the IL-2 mutant protein is fused directly or via a linker to the N-terminus of the Fc fragment.

7. The immunoconjugate of claim 4, wherein the Fc fragment to which the IL-2 mutant protein is fused is bound to the Fc fragment of the anti-PD-1 antibody.

8. The immunoconjugate of claim 4, wherein the Fc fragment to which the IL-2 mutant protein is fused comprises one or more mutations forming a Knob.

9. The immunoconjugate of claim 8, where the Knob is comprised of one or more mutations selected from T366W, S354C, and combinations thereof.

10. The immunoconjugate of claim 8, wherein the Fc fragment of the anti-PD-1 antibody comprises one or more mutations forming a Hole.

11. The immunoconjugate of claim 10, where in the Hole is comprised of one or more mutations selected from Y349C, T366S, L368A, Y407V, and combinations thereof.

12. The immunoconjugate of claim 4, wherein the Fc fragment to which the IL-2 mutant protein is fused comprises an amino acid sequence as set forth in SEQ ID NO: 42.

13. The immunoconjugate of claim 4, wherein the Fc fragment to which the IL-2 mutant protein is fused comprises the amino acid sequence as set forth in SEQ ID NO: 6.

14. The immunoconjugate of claim 10, wherein the Fc fragment of the anti-PD-1 antibody comprises the amino acid sequence as set forth in SEQ ID NO: 12.

15. The immunoconjugate of claim 1, wherein the anti-PD-1 antibody or antigen-binding fragment thereof comprises a heavy chain variable region comprising the amino acid sequence set forth in SEQ ID NO: 8, and a light chain variable region comprising the amino acid sequence set forth in SEQ ID NO: 15.

16. A pharmaceutical composition comprising an immunoconjugate, wherein the immunoconjugate comprises (i) a first monomer comprising an anti-PD-1 antibody and an Fc fragment, and (ii) a second monomer comprising an IL-2 mutant protein fused directly or via a linker to an Fc fragment, wherein the anti-PD-1 antibody or antigen-binding fragment thereof comprises a heavy chain comprising a heavy chain variable region, wherein the heavy chain variable region comprises HCDR1, HCDR2 and HCDR3 set forth in amino acid sequences of SEQ ID NOs: 9, 10 and 11, respectively, and a light chain comprising a light chain variable region, wherein the light chain variable region comprises LCDR1, LCDR2 and LCDR3 set forth in amino acid sequences of SEQ ID NOs: 16, 17 and 18, respectively; and the IL-2 mutant protein comprises the amino acid sequence set forth in SEQ ID NO: 25; wherein (a) the Fc fragment of the first monomer comprises a Knob and the Fc fragment of the second monomer comprises a Hole, or (b) the Fc fragment of the first monomer comprises a Hole and the Fc fragment of the second monomer comprises a Knob.

17. The pharmaceutical composition of claim 16, wherein the Fc fragment of (a) or (b) comprising the Knob comprises the amino acid sequence set forth in SEQ ID NO: 6.

18. The pharmaceutical composition of claim 16, wherein the Fc fragment of (a) or (b) comprising the Hole comprises the amino acid sequence set forth in SEQ ID NO: 12.

19. The pharmaceutical composition of claim 16, wherein the anti-PD-1 antibody or antigen-binding fragment thereof comprises a heavy chain variable region comprising the amino acid sequence forth in SEQ ID NO: 8, and a light chain variable region comprising the amino acid sequence set forth in SEQ ID NO: 15.

20. The pharmaceutical composition of claim 16, wherein the IL-2 mutant protein is fused to the Fc fragment via a linker comprising the amino acid sequence set forth in SEQ ID NO: 5.

21. The pharmaceutical composition of claim 16, wherein the IL-2 mutant protein comprises an N-terminus and a C-terminus, the Fc fragment comprises an N-terminus and a C-terminus, and wherein the C-terminus of the IL-2 mutant protein is fused directly or via a linker to the N-terminus of the Fc fragment.

22. A pharmaceutical composition comprising an immunoconjugate, wherein the immunoconjugate comprises (i) a first monomer comprising
  (a) an anti-PD-1 antibody comprising
    a heavy chain comprising the amino acid sequence set forth in SEQ ID NO: 14, and
    a light chain comprising the amino acid sequence set forth in SEQ ID NO: 20; and
(ii) a second monomer comprising
  (a) an IL-2 mutant protein, a linker, and an Fc fragment, wherein the second monomer comprises the amino acid sequence set forth in SEQ ID NO: 26.

23. A method of treating cancer in a subject, the method comprising administering to the subject the pharmaceutical composition of claim 22.

24. The method of claim 23, wherein the cancer is a PD-1 resistant cancer.

* * * * *

SEQUENCE LISTING

```
Sequence total quantity: 45
SEQ ID NO: 1            moltype = AA  length = 153
FEATURE                 Location/Qualifiers
source                  1..153
                        mol_type = protein
                        organism = synthetic construct
SEQUENCE: 1
MYRMQLLSCI ALSLALVTNS APTSSSTKKT QLQLEHLLLD LQMILNGINN YKNPKLTRML  60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                               153

SEQ ID NO: 2            moltype = AA  length = 133
FEATURE                 Location/Qualifiers
source                  1..133
                        mol_type = protein
                        organism = synthetic construct
SEQUENCE: 2
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 3            moltype = AA  length = 133
FEATURE                 Location/Qualifiers
source                  1..133
                        mol_type = protein
                        organism = synthetic construct
SEQUENCE: 3
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFSQSIIS TLT                                                     133

SEQ ID NO: 4            moltype = AA  length = 129
FEATURE                 Location/Qualifiers
source                  1..129
                        mol_type = protein
                        organism = synthetic construct
SEQUENCE: 4
APASSSTKKT QLQLEHLLLD LQMILNGINN YKNPKLTRML TFKFYMPKKA TELKHLQCLE  60
EELKPLEEVL NLAGDASIHD LISDINVIVL ELKGSETTFM CEYADETATI VEFLNRWITF  120
SQSIISTLT                                                          129

SEQ ID NO: 5            moltype = AA  length = 10
FEATURE                 Location/Qualifiers
source                  1..10
```

```
                       mol_type = protein
                       organism = synthetic construct
SEQUENCE: 5
GGGGSGGGGS                                                         10

SEQ ID NO: 6           moltype = AA  length = 227
FEATURE                Location/Qualifiers
source                 1..227
                       mol_type = protein
                       organism = synthetic construct
SEQUENCE: 6
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 7           moltype = AA  length = 366
FEATURE                Location/Qualifiers
source                 1..366
                       mol_type = protein
                       organism = synthetic construct
SEQUENCE: 7
APASSSTKKT QLQLEHLLLD LQMILNGINN YKNPKLTRML TFKFYMPKKA TELKHLQCLE  60
EELKPLEEVL NLAGDASIHD LISDINVIVL ELKGSETTFM CEYADETATI VEFLNRWITF  120
SQSIISTLTG GGGSGGGGSD KTHTCPPCPA PEAAGGPSVF LFPPKPKDTL MISRTPEVTC  180
VVVDVSHEDP EVKFNWYVDG VEVHNAKTKP REEQYNSTYR VVSVLTVLHQ DWLNGKEYKC  240
KVSNKALPAP IEKTISKAKG QPREPQVYTL PPCRDELTKN QVSLWCLVKG FYPSDIAVEW  300
ESNGQPENNY KTTPPVLDSD GSFFLYSKLT VDKSRWQQGN VFSCSVMHEA LHNHYTQKSL  360
SLSPGK                                                             366

SEQ ID NO: 8           moltype = AA  length = 120
FEATURE                Location/Qualifiers
source                 1..120
                       mol_type = protein
                       organism = synthetic construct
SEQUENCE: 8
QVQLVQSGAE VKKPGSSVKV SCKASGGTFS SYAISWVRQA PGQGLEWMGL IIPMFDTAGY  60
AQKFQGRVAI TVDESTSTAY MELSSLRSED TAVYYCARAE HSSTGTFDYW GQGTLVTVSS  120

SEQ ID NO: 9           moltype = AA  length = 10
FEATURE                Location/Qualifiers
source                 1..10
                       mol_type = protein
                       organism = synthetic construct
SEQUENCE: 9
GGTFSSYAIS                                                         10

SEQ ID NO: 10          moltype = AA  length = 17
FEATURE                Location/Qualifiers
source                 1..17
                       mol_type = protein
                       organism = synthetic construct
SEQUENCE: 10
LIIPMFDTAG YAQKFQG                                                 17

SEQ ID NO: 11          moltype = AA  length = 11
FEATURE                Location/Qualifiers
source                 1..11
                       mol_type = protein
                       organism = synthetic construct
SEQUENCE: 11
AEHSSTGTFD Y                                                       11

SEQ ID NO: 12          moltype = AA  length = 227
FEATURE                Location/Qualifiers
source                 1..227
                       mol_type = protein
                       organism = synthetic construct
SEQUENCE: 12
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 13          moltype = AA  length = 330
FEATURE                Location/Qualifiers
source                 1..330
                       mol_type = protein
                       organism = synthetic construct
```

```
SEQUENCE: 13
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VCTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 14           moltype = AA  length = 450
FEATURE                 Location/Qualifiers
source                  1..450
                        mol_type = protein
                        organism = synthetic construct
SEQUENCE: 14
QVQLVQSGAE VKKPGSSVKV SCKASGGTFS SYAISWVRQA PGQGLEWMGL IIPMFDTAGY  60
AQKFQGRVAI TVDESTSTAY MELSSLRSED TAVYYCARAE HSSTGTFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNHYT QKSLSLSPGK                                   450

SEQ ID NO: 15           moltype = AA  length = 107
FEATURE                 Location/Qualifiers
source                  1..107
                        mol_type = protein
                        organism = synthetic construct
SEQUENCE: 15
DIQMTQSPSS VSASVGDRVT ITCRASQGIS SWLAWYQQKP GKAPKLLISA ASSLQSGVPS  60
RFSGSGSGTD FTLTISSLQP EDFATYYCQQ ANHLPFTFGG GTKVEIK                107

SEQ ID NO: 16           moltype = AA  length = 11
FEATURE                 Location/Qualifiers
source                  1..11
                        mol_type = protein
                        organism = synthetic construct
SEQUENCE: 16
RASQGISSWL A                                                       11

SEQ ID NO: 17           moltype = AA  length = 7
FEATURE                 Location/Qualifiers
source                  1..7
                        mol_type = protein
                        organism = synthetic construct
SEQUENCE: 17
AASSLQS                                                            7

SEQ ID NO: 18           moltype = AA  length = 9
FEATURE                 Location/Qualifiers
source                  1..9
                        mol_type = protein
                        organism = synthetic construct
SEQUENCE: 18
QQANHLPFT                                                          9

SEQ ID NO: 19           moltype = AA  length = 107
FEATURE                 Location/Qualifiers
source                  1..107
                        mol_type = protein
                        organism = synthetic construct
SEQUENCE: 19
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 20           moltype = AA  length = 214
FEATURE                 Location/Qualifiers
source                  1..214
                        mol_type = protein
                        organism = synthetic construct
SEQUENCE: 20
DIQMTQSPSS VSASVGDRVT ITCRASQGIS SWLAWYQQKP GKAPKLLISA ASSLQSGVPS  60
RFSGSGSGTD FTLTISSLQP EDFATYYCQQ ANHLPFTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 21           moltype = AA  length = 347
FEATURE                 Location/Qualifiers
source                  1..347
```

```
                        mol_type = protein
                        organism = synthetic construct
SEQUENCE: 21
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK LALALALAIG GFCADCC                347

SEQ ID NO: 22           moltype = AA  length = 467
FEATURE                 Location/Qualifiers
source                  1..467
                        mol_type = protein
                        organism = synthetic construct
SEQUENCE: 22
QVQLVQSGAE VKKPGSSVKV SCKASGGTFS SYAISWVRQA PGQGLEWMGL IIPMFDTAGY  60
AQKFQGRVAI TVDESTSTAY MELSSLRSED TAVYYCARAE HSSTGTFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK LALALALAIG GFCADCC                467

SEQ ID NO: 23           moltype = AA  length = 129
FEATURE                 Location/Qualifiers
source                  1..129
                        mol_type = protein
                        organism = synthetic construct
SEQUENCE: 23
APASSSTKKT QLQLEHLLLD LQMILNGINN YKNPKLTRML TFKFYMPKKA TELKHLQCLE  60
EELKPLEEVL NLAGDASIHD LISRINVIVL ELKGSETTFM CEYADETATI VEFLNRWITF  120
SQSIISTLT                                                          129

SEQ ID NO: 24           moltype = AA  length = 366
FEATURE                 Location/Qualifiers
source                  1..366
                        mol_type = protein
                        organism = synthetic construct
SEQUENCE: 24
APASSSTKKT QLQLEHLLLD LQMILNGINN YKNPKLTRML TFKFYMPKKA TELKHLQCLE  60
EELKPLEEVL NLAGDASIHD LISRINVIVL ELKGSETTFM CEYADETATI VEFLNRWITF  120
SQSIISTLTG GGGSGGGGSD KTHTCPPCPA PEAAGGPSVF LFPPKPKDTL MISRTPEVTC  180
VVVDVSHEDP EVKFNWYVDG VEVHNAKTKP REEQYNSTYR VVSVLTVLHQ DWLNGKEYKC  240
KVSNKALPAP IEKTISKAKG QPREPQVYTL PPCRDELTKN QVSLWCLVKG FYPSDIAVEW  300
ESNGQPENNY KTTPPVLDSD GSFFLYSKLT VDKSRWQQGN VFSCSVMHEA LHNHYTQKSL  360
SLSPGK                                                             366

SEQ ID NO: 25           moltype = AA  length = 129
FEATURE                 Location/Qualifiers
source                  1..129
                        mol_type = protein
                        organism = synthetic construct
SEQUENCE: 25
APASSSTKKT QLQLEHLLLD LQMILNGINN YKNPKLTRML TFKFYMPKKA TELKHLQCLE  60
EELKPLEEVL NLAGDASIHD LISRINVIVL ELKGSETTFM CEYADETATI VEFLNRWITF  120
SQSIIRTLT                                                          129

SEQ ID NO: 26           moltype = AA  length = 366
FEATURE                 Location/Qualifiers
source                  1..366
                        mol_type = protein
                        organism = synthetic construct
SEQUENCE: 26
APASSSTKKT QLQLEHLLLD LQMILNGINN YKNPKLTRML TFKFYMPKKA TELKHLQCLE  60
EELKPLEEVL NLAGDASIHD LISRINVIVL ELKGSETTFM CEYADETATI VEFLNRWITF  120
SQSIIRTLTG GGGSGGGGSD KTHTCPPCPA PEAAGGPSVF LFPPKPKDTL MISRTPEVTC  180
VVVDVSHEDP EVKFNWYVDG VEVHNAKTKP REEQYNSTYR VVSVLTVLHQ DWLNGKEYKC  240
KVSNKALPAP IEKTISKAKG QPREPQVYTL PPCRDELTKN QVSLWCLVKG FYPSDIAVEW  300
ESNGQPENNY KTTPPVLDSD GSFFLYSKLT VDKSRWQQGN VFSCSVMHEA LHNHYTQKSL  360
SLSPGK                                                             366

SEQ ID NO: 27           moltype = AA  length = 129
FEATURE                 Location/Qualifiers
source                  1..129
                        mol_type = protein
                        organism = synthetic construct
SEQUENCE: 27
```

```
APASSSTKKT QLQLEHLLLD LQMILNGINN YKNPKLTRML TAKFYMPKKA TELKHLQCLE  60
EELKPLEEVL NLAQSKNFHD LISRINVIVL ELKGSETTFM CEYADETATI VEFLNRWITF  120
SQEIISTLT                                                          129

SEQ ID NO: 28          moltype = AA  length = 366
FEATURE                Location/Qualifiers
source                 1..366
                       mol_type = protein
                       organism = synthetic construct
SEQUENCE: 28
APASSSTKKT QLQLEHLLLD LQMILNGINN YKNPKLTRML TAKFYMPKKA TELKHLQCLE  60
EELKPLEEVL NLAQSKNFHD LISRINVIVL ELKGSETTFM CEYADETATI VEFLNRWITF  120
SQEIISTLTG GGGSGGGGSD KTHTCPPCPA PEAAGGPSVF LFPPKPKDTL MISRTPEVTC  180
VVVDVSHEDP EVKFNWYVDG VEVHNAKTKP REEQYNSTYR VVSVLTVLHQ DWLNGKEYKC  240
KVSNKALPAP IEKTISKAKG QPREPQVYTL PPCRDELTKN QVSLWCLVKG FYPSDIAVEW  300
ESNGQPENNY KTTPPVLDSD GSFFLYSKLT VDKSRWQQGN VFSCSVMHEA LHNHYTQKSL  360
SLSPGK                                                             366

SEQ ID NO: 29          moltype = AA  length = 129
FEATURE                Location/Qualifiers
source                 1..129
                       mol_type = protein
                       organism = synthetic construct
SEQUENCE: 29
APASSSTKKT QLQLEHLLLD LQMILNGINN YKNPKLTRML TAKFYMPKKA TELKHLQCLE  60
EELKPLEEVL NLAGDASIHD LISRINVIVL ELKGSETTFM CEYADETATI VEFLNRWITF  120
SQEIISTLT                                                          129

SEQ ID NO: 30          moltype = AA  length = 366
FEATURE                Location/Qualifiers
source                 1..366
                       mol_type = protein
                       organism = synthetic construct
SEQUENCE: 30
APASSSTKKT QLQLEHLLLD LQMILNGINN YKNPKLTRML TAKFYMPKKA TELKHLQCLE  60
EELKPLEEVL NLAGDASIHD LISRINVIVL ELKGSETTFM CEYADETATI VEFLNRWITF  120
SQEIISTLTG GGGSGGGGSD KTHTCPPCPA PEAAGGPSVF LFPPKPKDTL MISRTPEVTC  180
VVVDVSHEDP EVKFNWYVDG VEVHNAKTKP REEQYNSTYR VVSVLTVLHQ DWLNGKEYKC  240
KVSNKALPAP IEKTISKAKG QPREPQVYTL PPCRDELTKN QVSLWCLVKG FYPSDIAVEW  300
ESNGQPENNY KTTPPVLDSD GSFFLYSKLT VDKSRWQQGN VFSCSVMHEA LHNHYTQKSL  360
SLSPGK                                                             366

SEQ ID NO: 31          moltype = AA  length = 129
FEATURE                Location/Qualifiers
source                 1..129
                       mol_type = protein
                       organism = synthetic construct
SEQUENCE: 31
APASSSTKKT QLQLEHLLLD LQMILNGINN YKNPELTRML TFKFYMPKKA TELKHLQCLE  60
EELKPLEEVL NLAQSKNFHD LISRINVIVL ELKGSETTFM CEYADETATI VEFLNRWITF  120
SQEIISTLT                                                          129

SEQ ID NO: 32          moltype = AA  length = 366
FEATURE                Location/Qualifiers
source                 1..366
                       mol_type = protein
                       organism = synthetic construct
SEQUENCE: 32
APASSSTKKT QLQLEHLLLD LQMILNGINN YKNPELTRML TFKFYMPKKA TELKHLQCLE  60
EELKPLEEVL NLAQSKNFHD LISRINVIVL ELKGSETTFM CEYADETATI VEFLNRWITF  120
SQEIISTLTG GGGSGGGGSD KTHTCPPCPA PEAAGGPSVF LFPPKPKDTL MISRTPEVTC  180
VVVDVSHEDP EVKFNWYVDG VEVHNAKTKP REEQYNSTYR VVSVLTVLHQ DWLNGKEYKC  240
KVSNKALPAP IEKTISKAKG QPREPQVYTL PPCRDELTKN QVSLWCLVKG FYPSDIAVEW  300
ESNGQPENNY KTTPPVLDSD GSFFLYSKLT VDKSRWQQGN VFSCSVMHEA LHNHYTQKSL  360
SLSPGK                                                             366

SEQ ID NO: 33          moltype = AA  length = 597
FEATURE                Location/Qualifiers
source                 1..597
                       mol_type = protein
                       organism = synthetic construct
SEQUENCE: 33
EVQLLESGGG LVQPGGSLRL SCAASGFSFS SYTMSWVRQA PGKGLEWVAT ISGGGRDIYY  60
PDSVKGRFTI SRDNSKNTLY LQMNSLRAED TAVYYCVLLT GRVYFALDSW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPCRDE  360
LTKNQVSLWC LVKGFYPSDI AVEWESNGQP ENNYKTTPPV LDSDGSFFLY SKLTVDKSRW  420
```

```
QQGNVFSCSV MHEALHNHYT QKSLSLSPGG GGGSGGGGSG GGGSAPASSS TKKTQLQLEH  480
LLLDLQMILN GINNYKNPKL TRMLTAKFAM PKKATELKHL QCLEEELKPL EEVLNGAQSK  540
NFHLRPRDLI SNINVIVLEL KGSETTFMCE YADETATIVE FLNRWITFAQ SIISTLT     597

SEQ ID NO: 34          moltype = AA  length = 218
FEATURE                Location/Qualifiers
source                 1..218
                       mol_type = protein
                       organism = synthetic construct
SEQUENCE: 34
DIVMTQSPDS LAVSLGERAT INCKASESVD TSDNSFIHWY QQKPGQSPKL LIYRSSTLES  60
GVPDRFSGSG SGTDFTLTIS SLQAEDVAVY YCQQNYDVPW TFGQGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 35          moltype = AA  length = 5
FEATURE                Location/Qualifiers
source                 1..5
                       mol_type = protein
                       organism = synthetic construct
SEQUENCE: 35
EPKAS                                                              5

SEQ ID NO: 36          moltype = AA  length = 232
FEATURE                Location/Qualifiers
source                 1..232
                       mol_type = protein
                       organism = synthetic construct
SEQUENCE: 36
EPKASDKTHT CPPCPAPEAA GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVCTLPPSR DELTKNQVSL SCAVKGFYPS DIAVEWESNG QPENNYKTTP  180
PVLDSDGSFF LVSKLTVDKS RWQQGNVFSC SVMHEALHNH YTQKSLSLSP GK          232

SEQ ID NO: 37          moltype = AA  length = 370
FEATURE                Location/Qualifiers
source                 1..370
                       mol_type = protein
                       organism = synthetic construct
SEQUENCE: 37
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFSQSIIS TLTGGGGSGG GGSDKTHTCP PCPAPEAAGG PSVFLFPPKP KDTLMISRTP  180
EVTCVVVDVS HEDPEVKFNW YVDGVEVHNA KTKPREEQYN STYRVVSVLT VLHQDWLNGK  240
EYKCKVSNKA LPAPIEKTIS KAKGQPREPQ VYTLPPCRDE LTKNQVSLWC LVKGFYPSDI  300
AVEWESNGQP ENNYKTTPPV LDSDGSFFLY SKLTVDKSRW QQGNVFSCSV MHEALHNHYT  360
QKSLSLSPGK                                                         370

SEQ ID NO: 38          moltype = AA  length = 456
FEATURE                Location/Qualifiers
source                 1..456
                       mol_type = protein
                       organism = synthetic construct
SEQUENCE: 38
AVNGTSQFTC FYNSRANISC VWSQDGALQD TSCQVHAWPD RRRWNQTCEL LPVSQASWAC  60
NLILGAPDSQ KLTTVDIVTL RVLCREGVRW RVMAIQDFKP FENLRLMAPI SLQVVHVETH  120
RCNISWEISQ ASHYFERHLE FEARTLSPGH TWEEAPLLTL KQKQEWICLE TLTPDTQYEF  180
QVRVKPLQGE FTTWSPWSQP LAFRTKPAAL GKDTGLNDIF EAQKIEWHED KTHTCPPCPA  240
PEAAGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPCRDELTKN QVSLWCLVKG FYPSDIAVEW ESNGQPENNY KTTPPVLDSD GSFFLYSKLT  420
VDKSRWQQGN VFSCSVMHEA LHNHYTQKSL SLSPGK                            456

SEQ ID NO: 39          moltype = AA  length = 481
FEATURE                Location/Qualifiers
source                 1..481
                       mol_type = protein
                       organism = synthetic construct
SEQUENCE: 39
LNTTILTPNG NEDTTADFFL TTMPTDSLSV STLPLPEVQC FVFNVEYMNC TWNSSSEPQP  60
TNLTLHYWYK NSDNDKVQKC SHYLFSEEIT SGCQLQKKEI HLYQTFVVQL QDPREPRRQA  120
TQMLKLQNLV IPWAPENLTL HKLSESQLEL NWNNRFLNHC LEHLVQYRTD WDHSWTEQSV  180
DYRHKFSLPS VDGQKRYTFR VRSRFNPLCG SAQHWSEWSH PIHWGSNTSK ENGLNDIFEA  240
QKIEWHEHHH HHHDKTHTHC PPCPAPEAAG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPAPIEKTI SKAKGQPREP QVCTLPPSRD ELTKNQVSLS CAVKGFYPSD IAVEWESNGQ  420
PENNYKTTPP VLDSDGSFFL VSKLTVDKSR WQQGNVFSCS VMHEALHNRY TQKSLSLSPG  480
K                                                                  481
```

```
SEQ ID NO: 40          moltype = AA  length = 7
FEATURE                Location/Qualifiers
source                 1..7
                       mol_type = protein
                       organism = synthetic construct
SEQUENCE: 40
AGDASIH                                                    7

SEQ ID NO: 41          moltype = AA  length = 11
FEATURE                Location/Qualifiers
source                 1..11
                       mol_type = protein
                       organism = synthetic construct
SEQUENCE: 41
AQSKNFHLRP R                                               11

SEQ ID NO: 42          moltype = AA  length = 7
FEATURE                Location/Qualifiers
source                 1..7
                       mol_type = protein
                       organism = synthetic construct
SEQUENCE: 42
AQSKNFH                                                    7

SEQ ID NO: 43          moltype = AA  length = 227
FEATURE                Location/Qualifiers
source                 1..227
                       mol_type = protein
                       organism = synthetic construct
SEQUENCE: 43
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 44          moltype = AA  length = 227
FEATURE                Location/Qualifiers
source                 1..227
                       mol_type = protein
                       organism = synthetic construct
SEQUENCE: 44
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 45          moltype = AA  length = 450
FEATURE                Location/Qualifiers
source                 1..450
                       mol_type = protein
                       organism = synthetic construct
SEQUENCE: 45
EVQLLESGGG LVQPGGSLRL SCAASGFSFS SYTMSWVRQA PGKGLEWVAT ISGGGRDIYY  60
PDSVKGRFTI SRDNSKNTLY LQMNSLRAED TAVYYCVLLT GRVYFALDSW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNHYT QKSLSLSPGK                                  450
```